(12) United States Patent
Zhang

(10) Patent No.: US 9,963,485 B2
(45) Date of Patent: May 8, 2018

(54) CYCLOHEPTAPEPTIDE AGENTS FOR TREATMENT OF CANCER AND OBESITY DISEASES

(71) Applicant: Hong Kong Baptist University, Kowloon (HK)

(72) Inventor: Hongjie Zhang, Kowloon (HK)

(73) Assignee: Hong Kong Baptist University, Hong Kong (HK)

( * ) Notice: Subject to any disclaimer, the term of this patent is extended or adjusted under 35 U.S.C. 154(b) by 0 days. days.

(21) Appl. No.: 15/293,516

(22) Filed: Oct. 14, 2016

(65) Prior Publication Data

US 2017/0096454 A1    Apr. 6, 2017

Related U.S. Application Data

(63) Continuation-in-part of application No. 13/804,276, filed on Mar. 14, 2013, now Pat. No. 9,499,586.

(60) Provisional application No. 61/795,443, filed on Oct. 16, 2012.

(51) Int. Cl.
| | |
|---|---|
| *A61K 38/00* | (2006.01) |
| *C07K 7/64* | (2006.01) |
| *C07C 229/04* | (2006.01) |
| *C07K 11/02* | (2006.01) |

(52) U.S. Cl.
CPC ............. *C07K 7/64* (2013.01); *C07C 229/04* (2013.01); *C07K 11/02* (2013.01); *A61K 38/00* (2013.01); *C07C 2601/02* (2017.05)

(58) Field of Classification Search
None
See application file for complete search history.

(56) References Cited

FOREIGN PATENT DOCUMENTS

| CN | 104640873 A | 5/2015 |
|---|---|---|
| WO | 9947489 A1 | 9/1999 |
| WO | 0075102 A1 | 12/2000 |

OTHER PUBLICATIONS http://www.mayoclinic.org/diseases-conditions/obesity/basics/prevention/con-20014834; last accessed Sep. 29, 2017.*
Medline Plus, http://www.nlm.nih.gov/medlineplus/obesity.html ; last accessed Sep. 29, 2017.*
National Institute of Cancer—What is Cancer? understanding and related topics, accessed Sep. 29, 2017 at URL: https://www.cancer.gov/about-cancer/understanding/what-is-cancer.*
A to Z Cancer https://www.cancer.gov/types; last accessed Sep. 29, 2017.*
C. J. White and A. K. Yudin, "Contemporary Strategies for Peptide Macrocyclization", Nature Chemistry, vol. 3, Jul. 2011, pp. 509-524; DOI: 10.1038/NCHEM.1062.
M. G. Hollingshead, M. C. Alley, R. F. Camalier, B. J. Abbott, J. G. Mayo, L. Malspeis, and M. R. Grever, "In Vivo Cultivation of Tumor Cells in Hollow Fibers", Life Sciences, vol. 57, No. 2, 1995, pp. 131-141.
Q. Mi, D. Lantvit, E. Reyes-Lim, H. Chai, W. Zhao, I-S Lee, S. Peraza-Sanchez, O. Ngassapa, L. B. S. Kardono, S. Riswan, M. G. Hollingshead, J. G. Mayo, N. R. Farnsworht, G. A. Cordell, A. D. Kinghorn, and J. M. Pezzuto, "Evaluation of the Potential Cancer Chemotherapeutic Efficacy of Natural Product Isolates Employing in Vivo Hollow Fiber Tests", J. Nat. Prod., 2002, vol. 65, pp. 842-850; DOI: 10.1021/np010322w.
W-F Li, J. Wang, J-J Zhang, X. Song, C-F Ku, J. Zou, J-X Li, L-J Rong, L-T Pan, and H-J Zhang, "Henrin A: A New Anti-HIV Ent-Kaurane Diterpene from Pteris Henryi", Int. J. Mol. Sci. 2015, vol. 16, pp. 27978-27987; DOI: 10.3390/ijms161126071.
U.S. Department of Health and Human Services, Food and Drug Administration, Center for Drug Evaluation and Research, Guidance for Industry, Estimating the Maximum Safe Starting Dose in Initial Clinical Trials for Therapeutics in Adult Healthy Volunteers, Pharmacology and Toxicology, Jul. 2005, Rockville, MD, U.S.A.
International Search Report of PCT/CN2017/106025 dated Jan. 16, 2018.
Lackner G. et al., Endofungal bacteria as producers of mycotoxins, Trends in Microbiology, Jan. 10, 2009, No. 12, vol. 17, p. 570-576.

* cited by examiner

*Primary Examiner* — Jeanette M Lieb
(74) *Attorney, Agent, or Firm* — Idea Intellectual Limited; Margaret A. Burke; Sam T. Yip

(57) ABSTRACT

New anticancer and anti-obesity agents based on cyclic peptide compounds are isolated from the stem barks of *Maytenus variabilis* (Loes.) C. Y. Cheng (Celastraceae). The invention also includes its preparation and application method for treating cancer and obesity diseases.

17 Claims, 53 Drawing Sheets

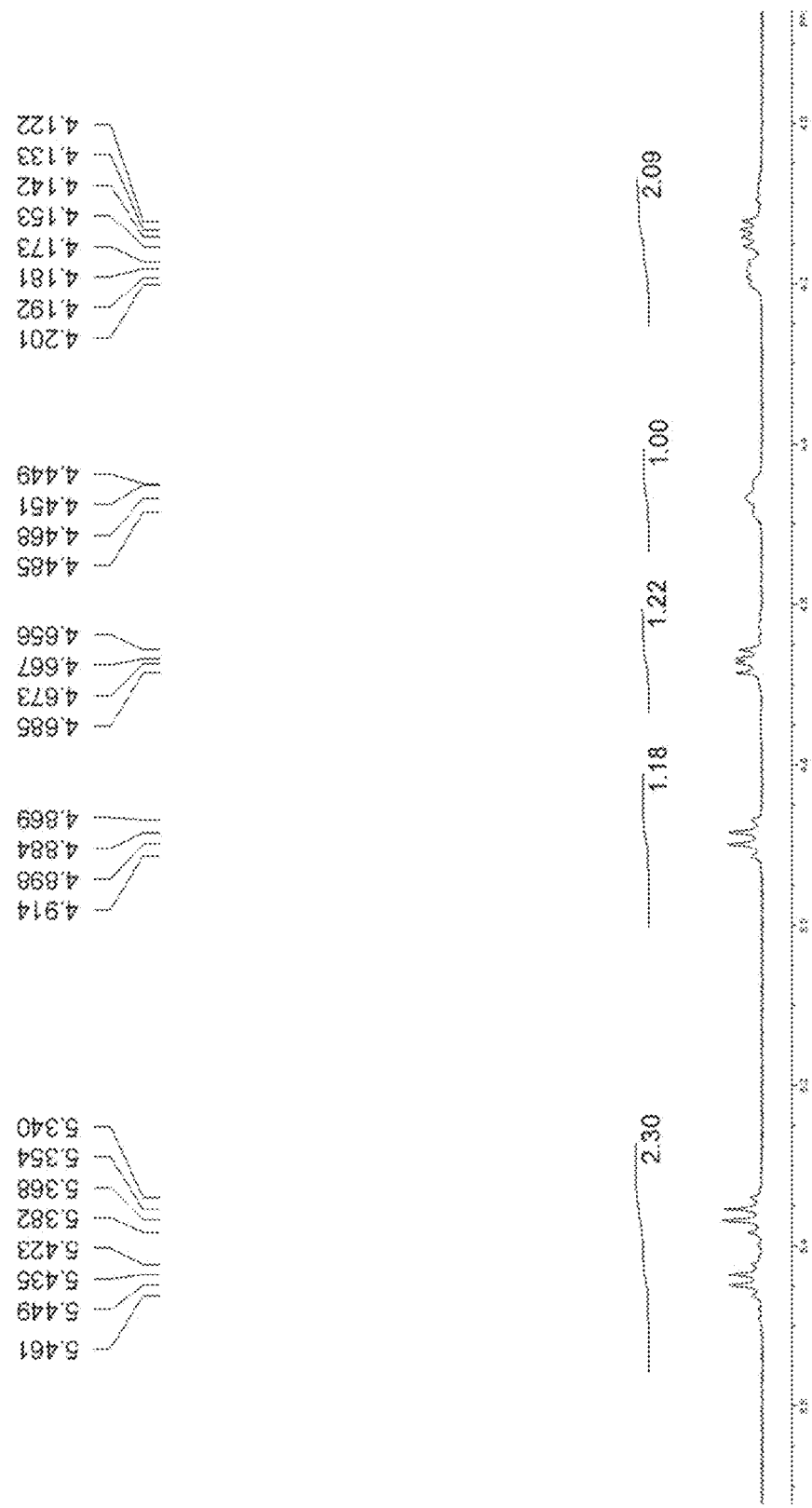

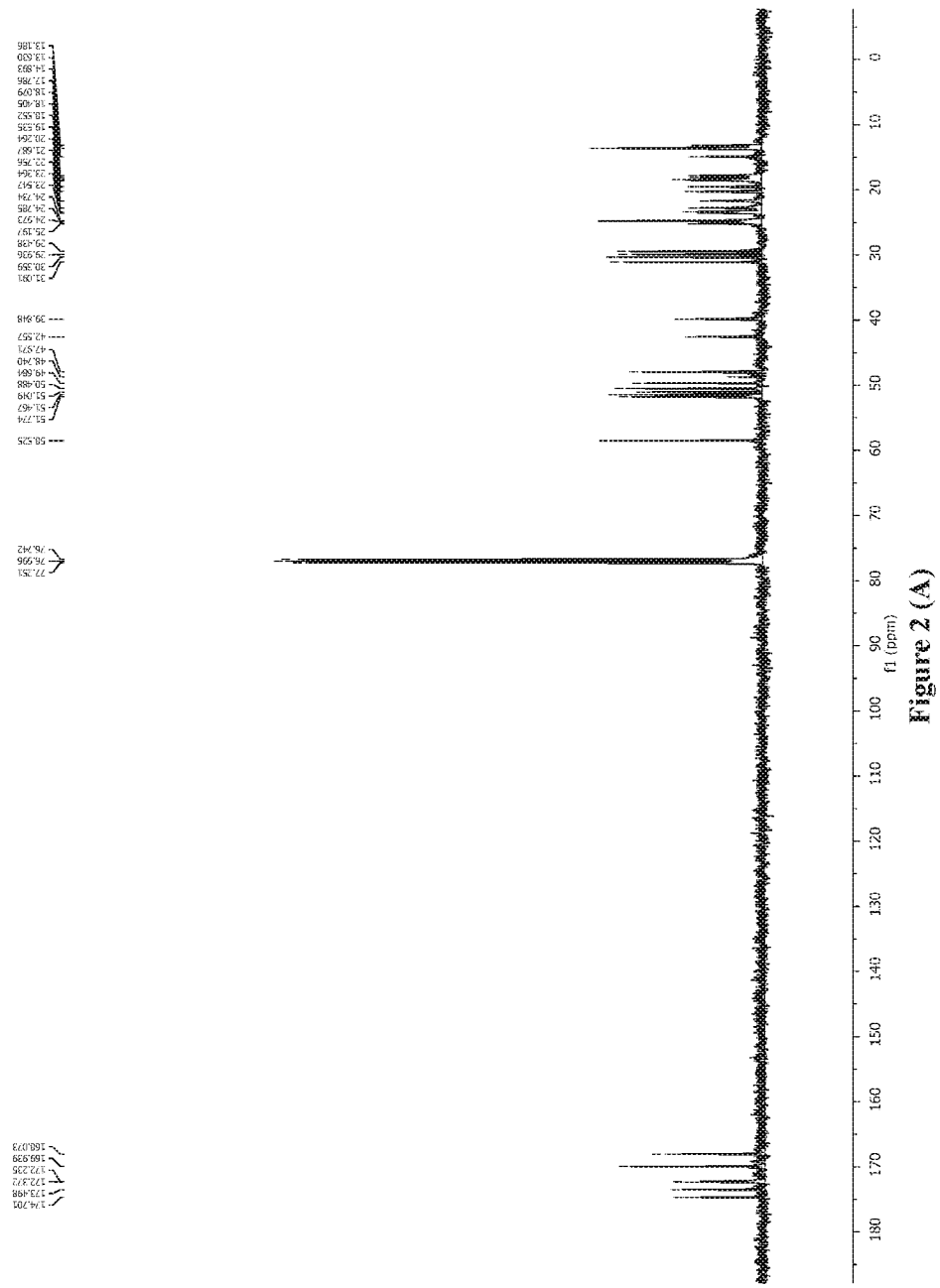

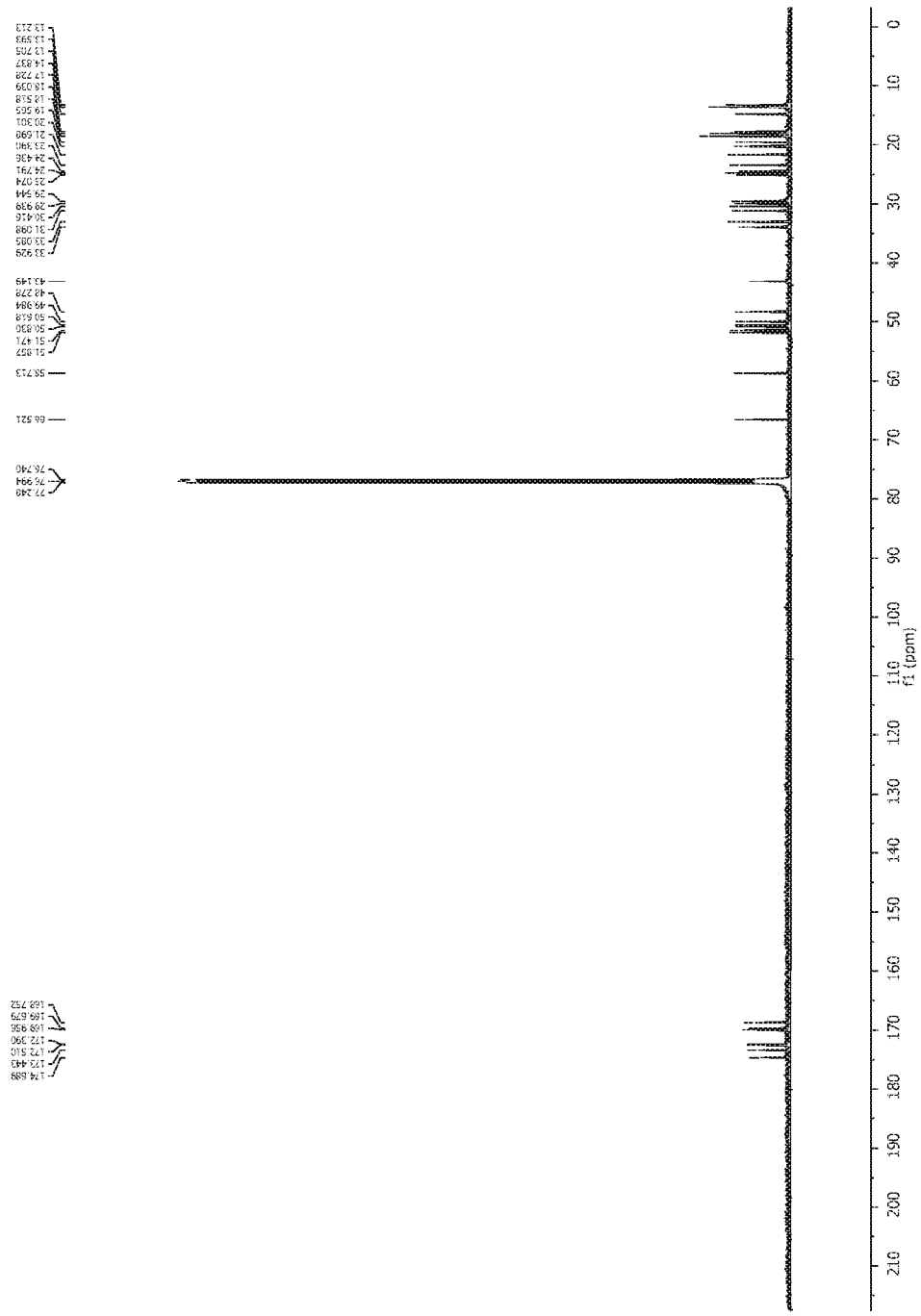

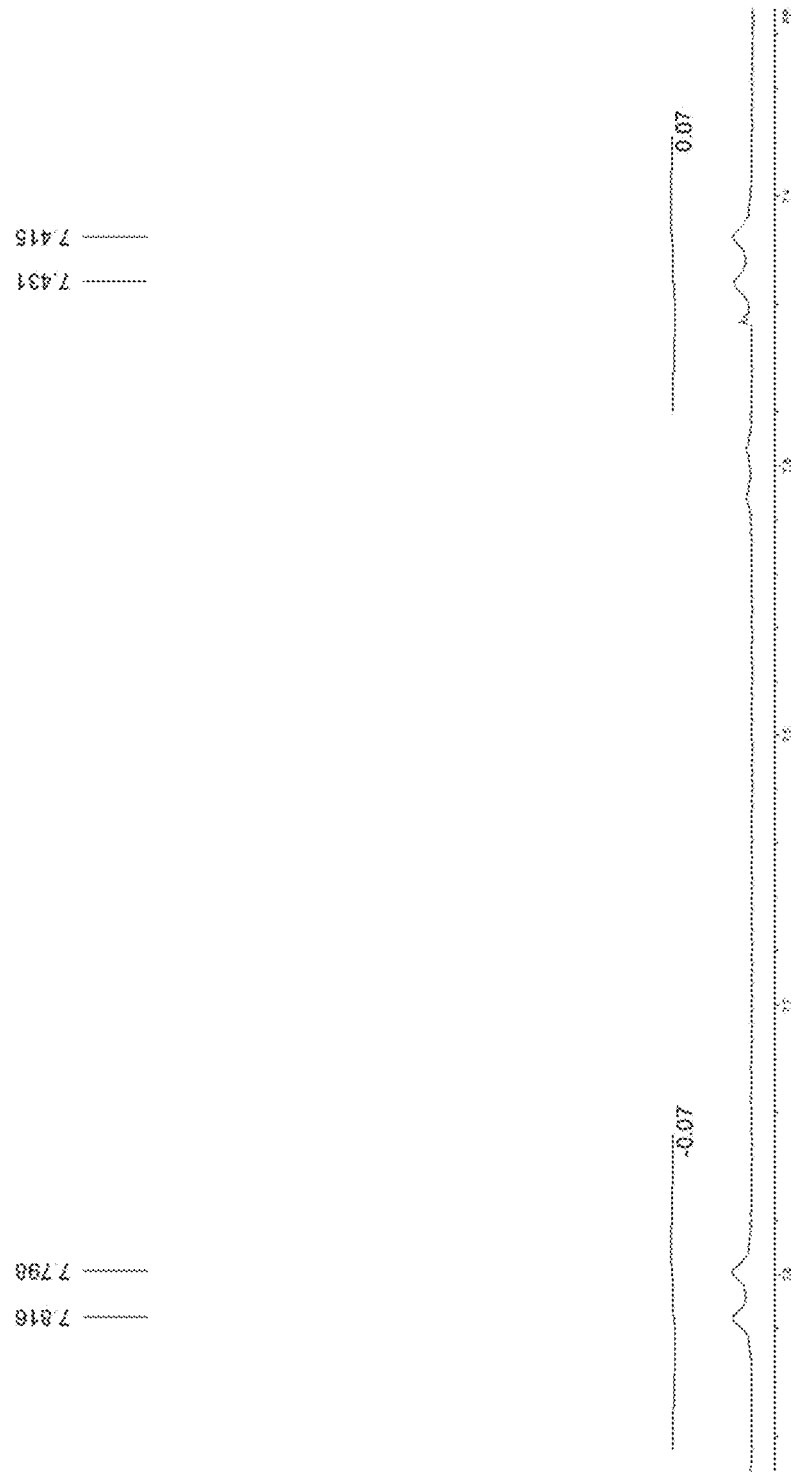

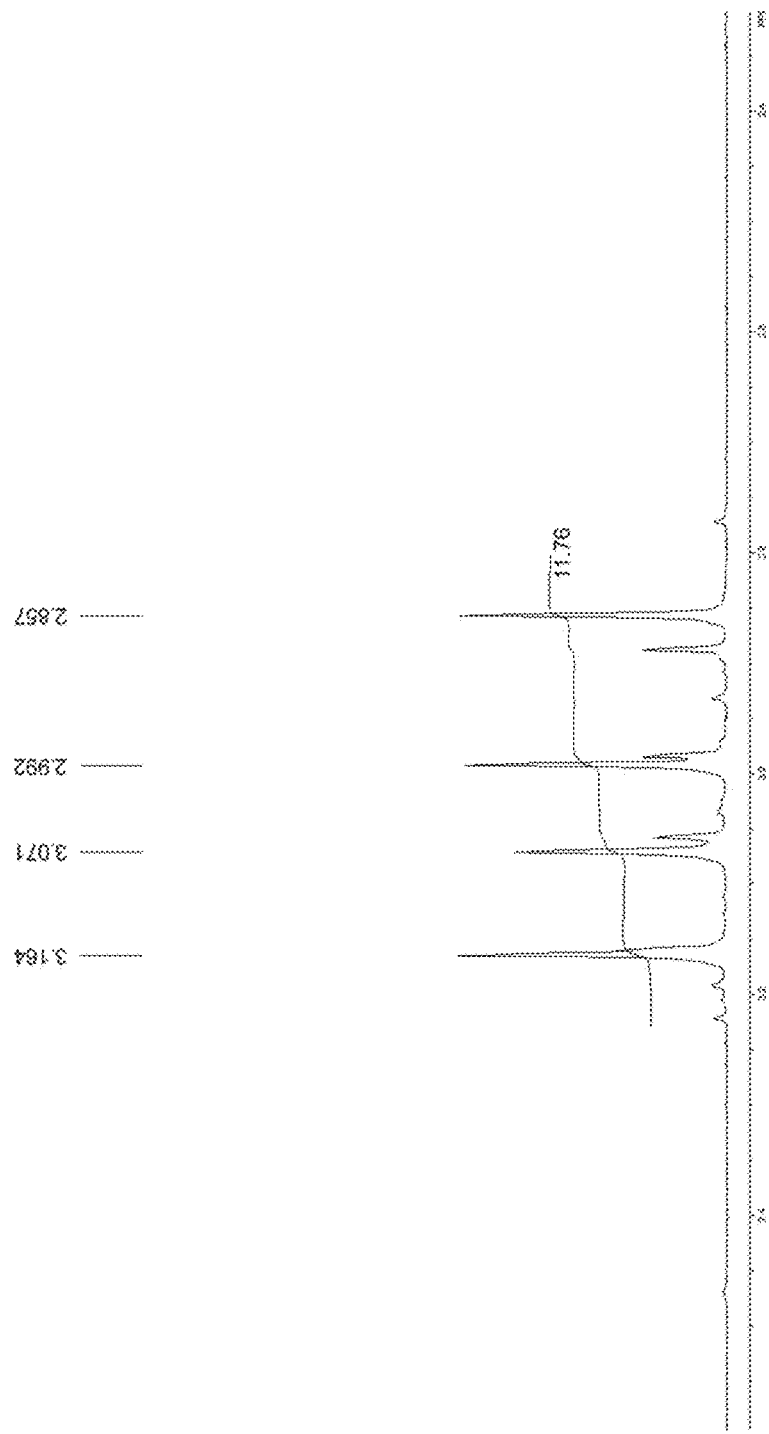

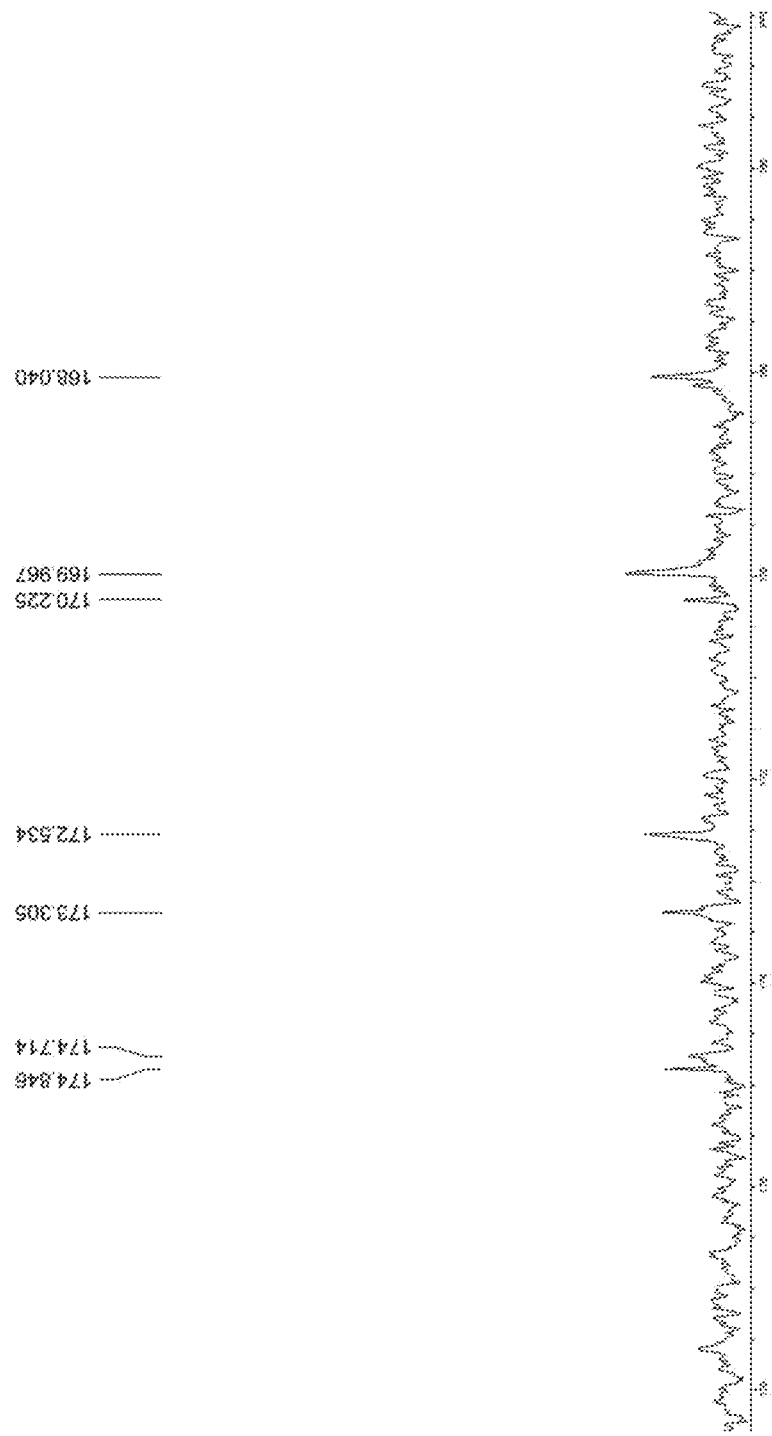

CYCLOHEPTAPEPTIDE AGENTS FOR TREATMENT OF CANCER AND OBESITY DISEASES

CROSS-REFERENCE TO RELATED APPLICATIONS

The present application is a continuation-in-part of U.S. Non-Provisional patent application Ser. No. 13/804,276, filed on Mar. 14, 2013, which claims the benefit of U.S. Provisional Patent Application Ser. No. 61/795,443, filed on 16 Oct. 2012. The disclosures of both U.S. Non-Provisional patent application Ser. No. 13/804,276 and U.S. Provisional Patent Application Ser. No. 61/795,443 are hereby incorporated by reference in their entirety.

TECHNICAL FIELD

This invention is in the field of pharmaceuticals and chemical industries. In particular, this invention relates to new anticancer and anti-obesity agents based on the cyclic peptide compounds. The invention also includes its preparation and application method for treating cancer and obesity diseases.

BACKGROUND OF INVENTION

The present invention relates to anticancer and anti-obesity agents based on cyclic peptide compounds. More particularly, the agents are derivatives of cycloheptapeptides. It is a goal of the present invention to provide cyclopeptide compounds having anticancer and anti-obesity activity.

More than 10 million people are diagnosed with cancer every year in the world. Cancer has become a leading cause of death. According to the compiled statistics by WHO, cancer claimed the lives of more than 8.2 million people worldwide in 2012 (WHO: http://www.who.int/mediacentre/factsheets/fs297/en/index.html; retrieved on 18 Sep. 2016). Although numerous cancer chemotherapeutics are available today, they often have very narrow therapeutic indices and very severe side effects. In addition, cancers can and often do develop resistance to many of these drugs. The fact that there currently are no drugs available that are capable of curing cancer diseases, the discovery and development of new anticancer drugs are very much needed and the undertaking of such studies is imperative.

Obesity, the metabolic disease, has become increasingly concerned in modern society. It affects nearly a third population of adults in the developed countries, and more than 1.9 billion adults were overweight in 2014 according to WHO report (http://www.who.int/mediacentre/factsheets/fs311/en/, retrieved on 18 Sep. 2016). Many health problems such as cardiovascular diseases, type 2 diabetes, cancer and osteoarthritis are associated with obesity. Obesity is largely preventable, and in fact, it is considered to be a leading preventable cause of death in the world. However, the number of people with obesity in the world is more than doubled since 1980. Obesity, the once considered a wealthy country problem is now on the rise in low- and middle-income countries. Therefore, in many cases, treatment may become inevitable option. There are only a few anti-obesity drugs (orlistat, lorcaserin hydrochloride and Qsymia™) approved by the FDA for long term use. The drugs have side effects associated with high blood pressure, rapid heart eat, palpitations, drug addiction, hallucination, constipation and insomnia. To develop new anti-obesity drugs is thus needed.

Cyclopeptides (cyclic peptide) are peptide compounds whose amino and carboxyl termini are linked together by a peptide bond to form a circular chain. Cyclodepsipeptides have at least one lactone linkage in place of one of the amides. A cycloheptapeptide is the cyclopeptide compound containing seven amino acid residues.

A large number of cyclopeptides have been synthesized due to their variety of biological activities including anticancer activity (White C J, Yudin A K. Contemporary strategies for peptide macrocylization. Nature Chemistry 2011; 3: 509-524. Chatterjee J, Gilon C, Hoffman A, Kessler H. N-methylation of peptides: a new perspective in medicinal chemistry. Accounts of Chemical Research 2008; 41: 1331-1342). However, cyclopeptides containing rare amino acids are seldom reported either from synthetic study or from nature. The inventor has discovered novel cyclopeptides that contain a unique amino acid residue in the structure.

Citation or identification of any reference in this section or any other section of this application shall not be construed as an admission that such reference is available as prior art for the present application.

SUMMARY OF INVENTION

The present invention relates to cycloheptapeptides. The present invention is based, at least in part, on the discovery that cyclopeptide compounds such as compound MV-A is effective in the treatment of cancer such as colon cancer, breast cancer, prostate cancer, lung cancer, melanoma, leukemia, brain cancer, renal cancer, ovarian cancer, and oral epidermoid cancer as well as obesity diseases.

Accordingly, a first aspect of the invention is a cycloheptapeptide compound or a pharmaceutically acceptable salt or prodrug thereof, for use in the treatment, prevention or delay of progression of a cancer or an obesity in a patient. The cycloheptapeptide may be a cyclohepta-depsipeptide compound.

A second aspect of the invention is a pharmaceutical formulation comprising a cycloheptapeptide compound, or a pharmaceutically acceptable salt or prodrug thereof, for use in the treatment, prevention or delay of progression of a cancer or an obesity in a patient. The cycloheptapeptide may be a cyclohepta-depsipeptide compound.

A third aspect of the invention concerns the use of a combination of one or more cycloheptapeptide(s) based on the formula (I) or the formula (II) with one or more other clinically used anticancer or anti-obesity agent(s), for use in the treatment, prevention or delay of progression of a cancer or an obesity in a patient.

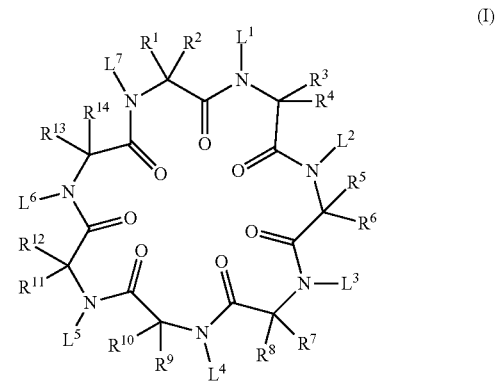

(I)

-continued

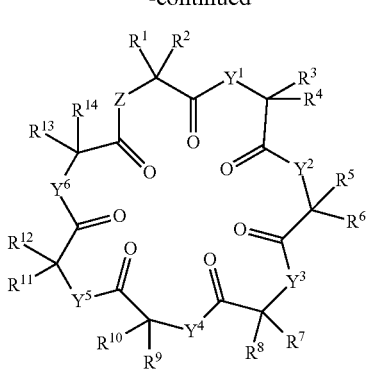
(II)

A fourth aspect of the invention concerns the use of an extract or a fraction made from plant material or extraction material fermented from a microorganism containing one or more cycloheptapeptide(s) based on the formula (I) or the formula (II) for use in the treatment, prevention or delay of progression of a cancer or an obesity in a patient.

A fifth aspect of the present invention, there is provided a method for use in the treatment, prevention or delay of progression of cancer or obesity in a subject in needs thereof by administering an effective dosage of a composition comprising a compound according to formula (II):

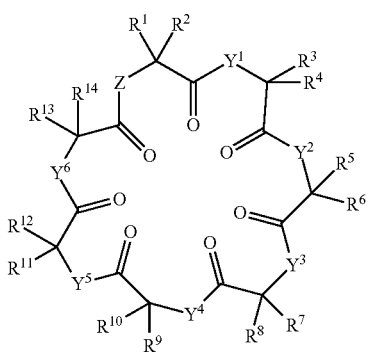
(II)

In a first embodiment of the fifth aspect of the present invention, there is provided a method and a composition, wherein said composition comprising a compound having formula (I):

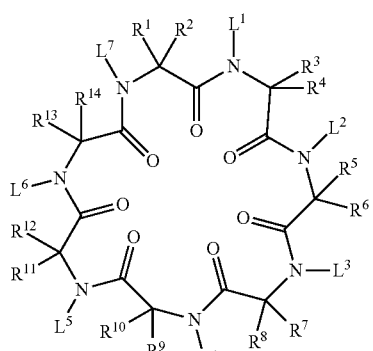
(I)

In a second embodiment of the fifth aspect of the present invention, there is provided a compound, wherein said compound is an optically pure stereoisomer; an enantiomer; a racemate; a diastereomer; or a tautomer.

In a third embodiment of the fifth aspect of the present invention, there is provided a compound is selected from compound MV-A, compound MV-B, compound MV-C or compound MV-D:

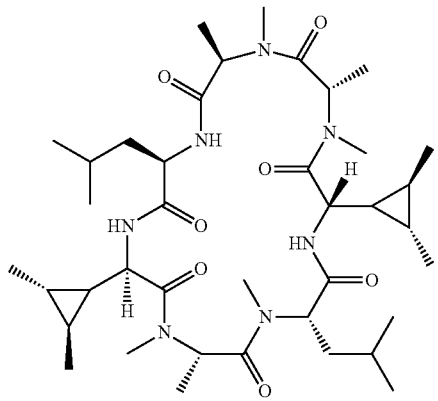
MV-A

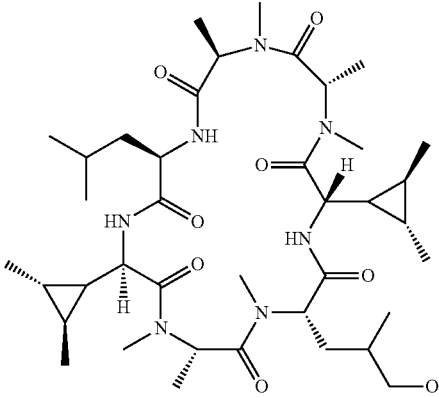
MV-B

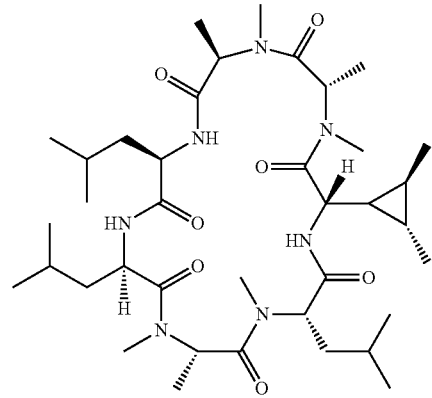
MV-C

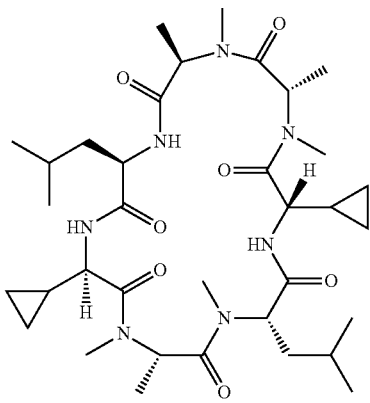

MV-D

In a fourth embodiment of the fifth aspect of the present invention, there is provided a method, wherein said subject is a human.

In a fifth embodiment of the fifth aspect of the present invention, there is provided a method, wherein said cancer comprising colon cancer, breast cancer, prostate cancer, lung cancer, melanoma, leukemia, brain cancer, renal cancer, ovarian cancer, and oral epidermoid cancer.

In a sixth embodiment of the fifth aspect of the present invention, the effective dosage is at least 0.0041 mg/kg per patient body weight, preferably about 0.0081 mg/kg per patient body weight, or preferably about 0.0162 mg/kg per patient body weight, or preferably about 0.0324 mg/kg per patient body weight, or preferably about 0.0649 mg/kg per patient body weight, or preferably about 0.0405 mg/kg per patient body weight, or preferably about 0.0811 mg/kg per patient body weight or preferably about 0.162 mg/kg per patient body weight.

A sixth aspect of the present invention concerns an amide or amine that contains at least one substructure that is formed from the amino acid having the formula (III).

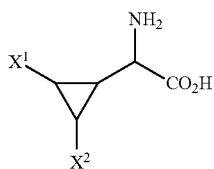

(III)

Compounds of the invention may exist in different forms, such as free acids, free bases, enantiomers, racemates, diastereomers, esters and other prodrugs, salts and tautomers, and the disclosure includes all variant forms of these compounds.

The extent of protection includes counterfeit or fraudulent products which contain or purport to contain a compound of the invention irrespective of whether they do in fact contain such a compound and irrespective of whether any such compound is contained in a therapeutically effective amount.

Included in the scope of protection are packages, which include a description or instructions which indicate that the package contains a species or pharmaceutical formulation of the invention and a product which is or comprises, or purports to be or comprise, such a formulation or species. Such packages may be, but are not necessarily, counterfeit or fraudulent.

Features, integers, characteristics, compounds, chemical moieties or groups described in conjunction with a particular aspect, embodiment or example of the invention are to be understood to be applicable to any other aspect, embodiment or example described herein unless incompatible therewith.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which.

DETAILED DESCRIPTION OF INVENTION

Figure 1:
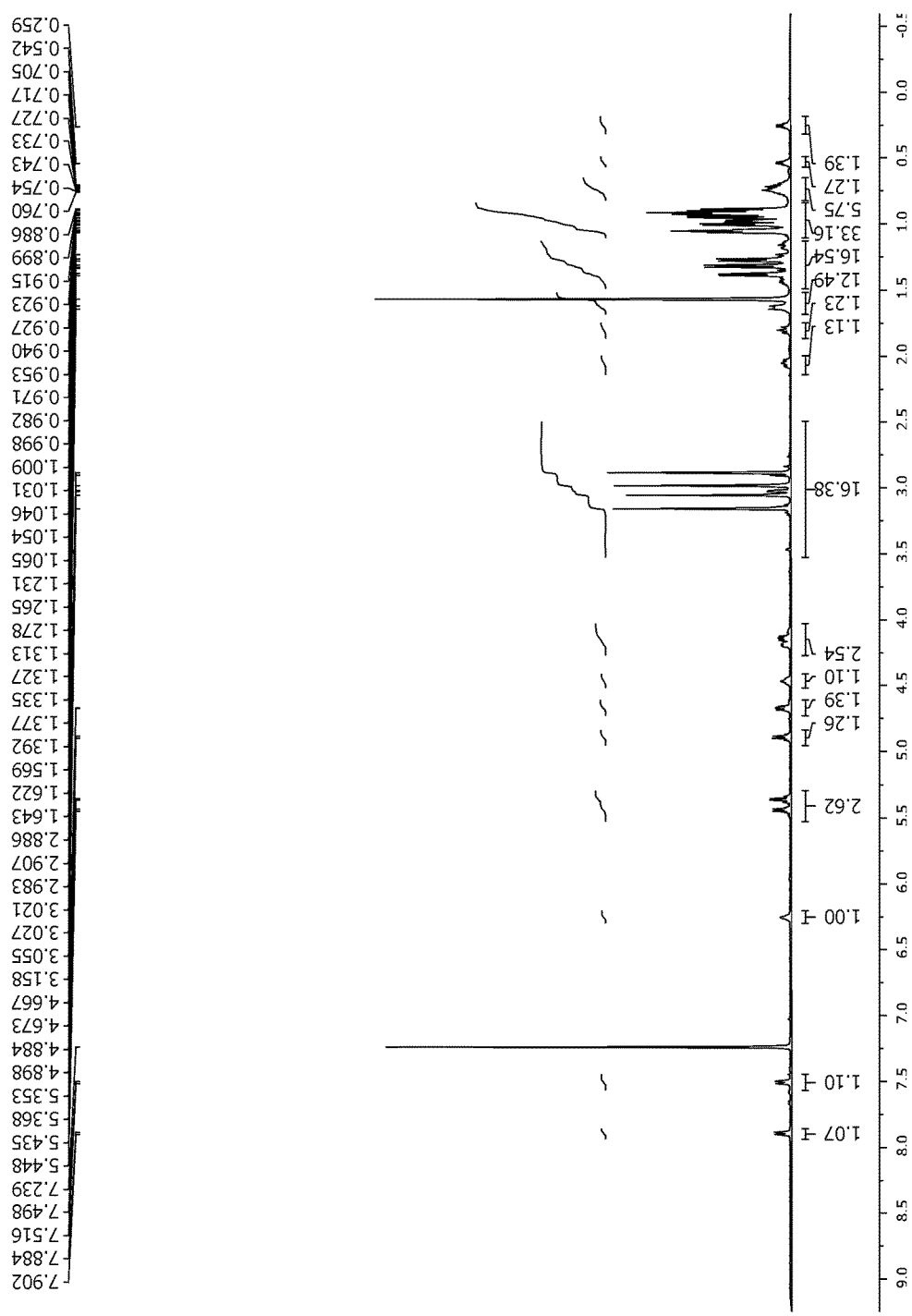
FIG. 1(A) shows $^1$H NMR data of 1 ($CDCl_3$).
FIG. 1(B) shows $^1$H NMR data of 1 ($CDCl_3$).
FIG. 1(C) shows $^1$H NMR data of 1 ($CDCl_3$).
FIG. 1(D) shows $^1$H NMR data of 1 ($CDCl_3$).
FIG. 1(E) shows $^1$H NMR data of 1 ($CDCl_3$).
FIG. 1(F) shows $^1$H NMR data of 1 ($CDCl_3$).
FIG. 1(G) shows $^1$H NMR data of 1 ($CDCl_3$).
FIG. 1(H) shows $^1$H NMR data of 1 ($CDCl_3$).
Figure 1B:
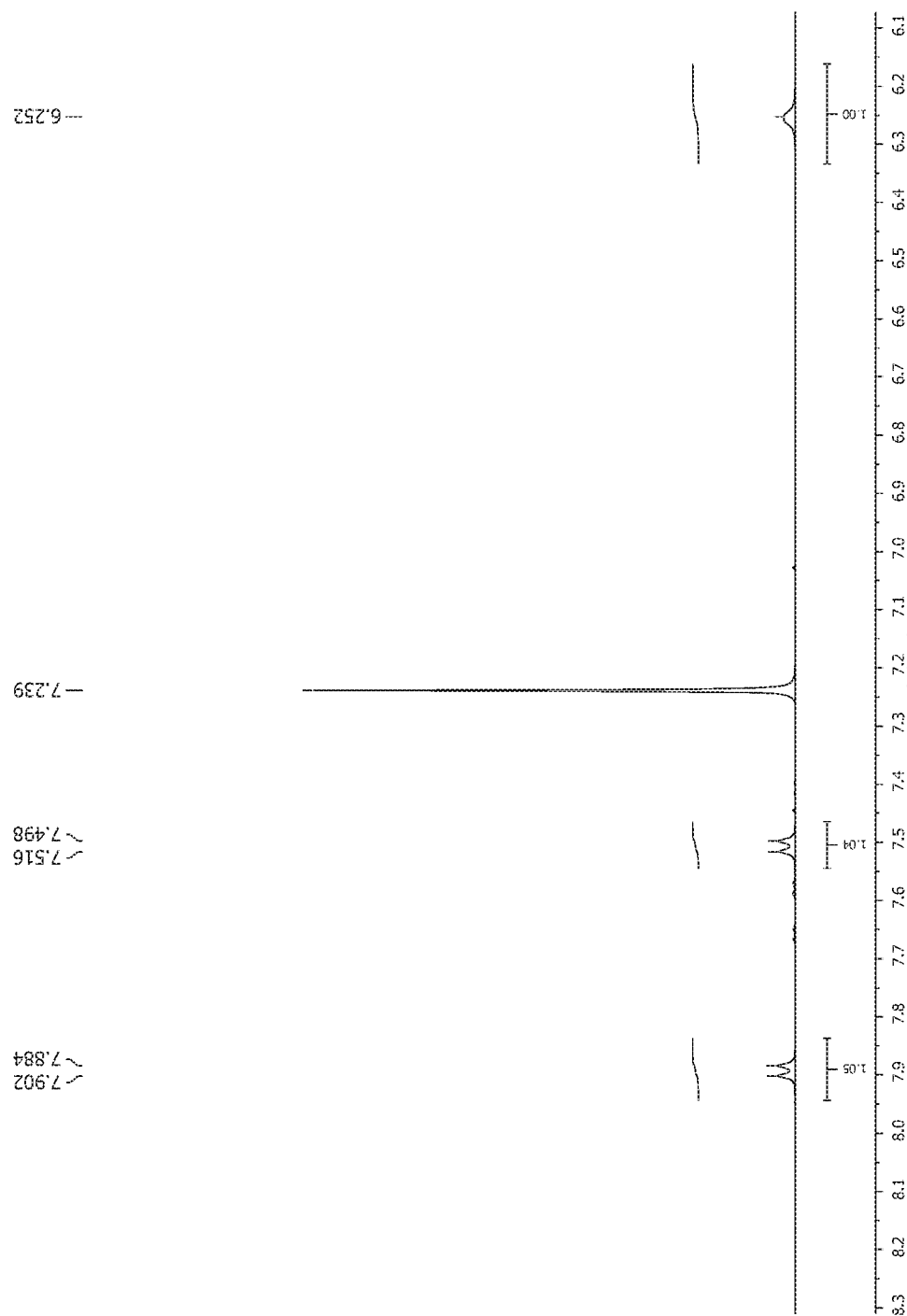
Figure 1:
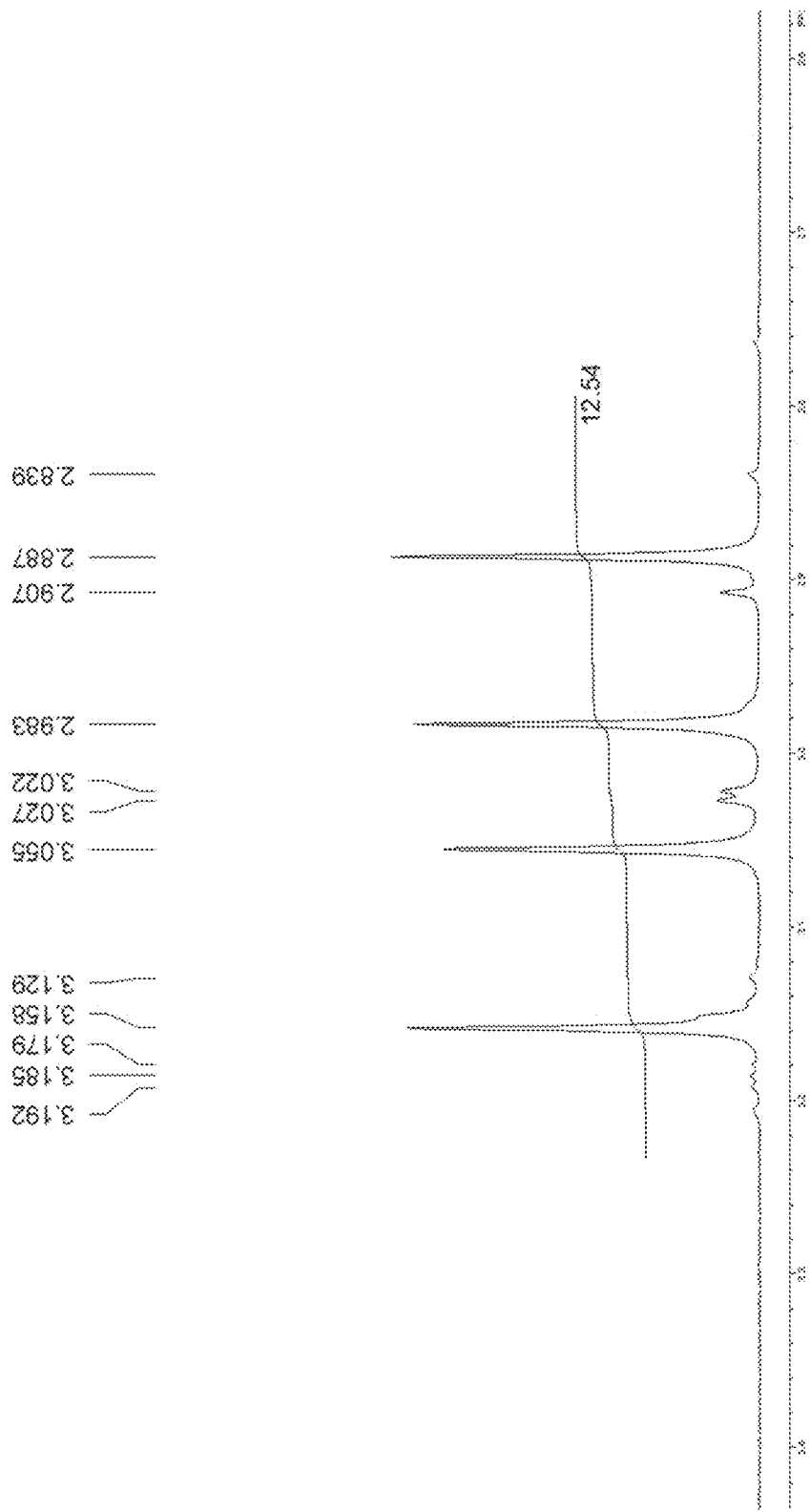
Figure 1:
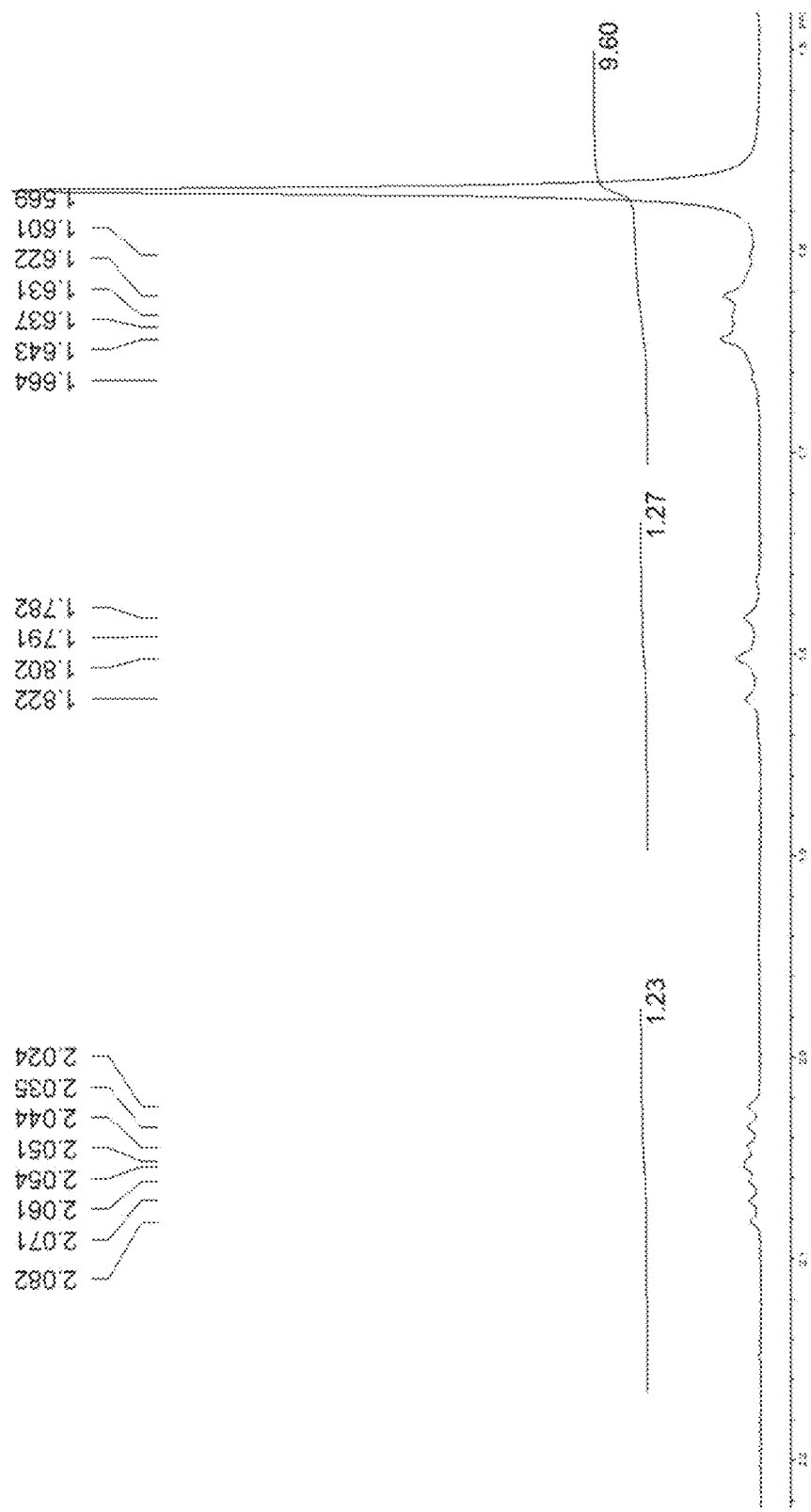
Figure 1:
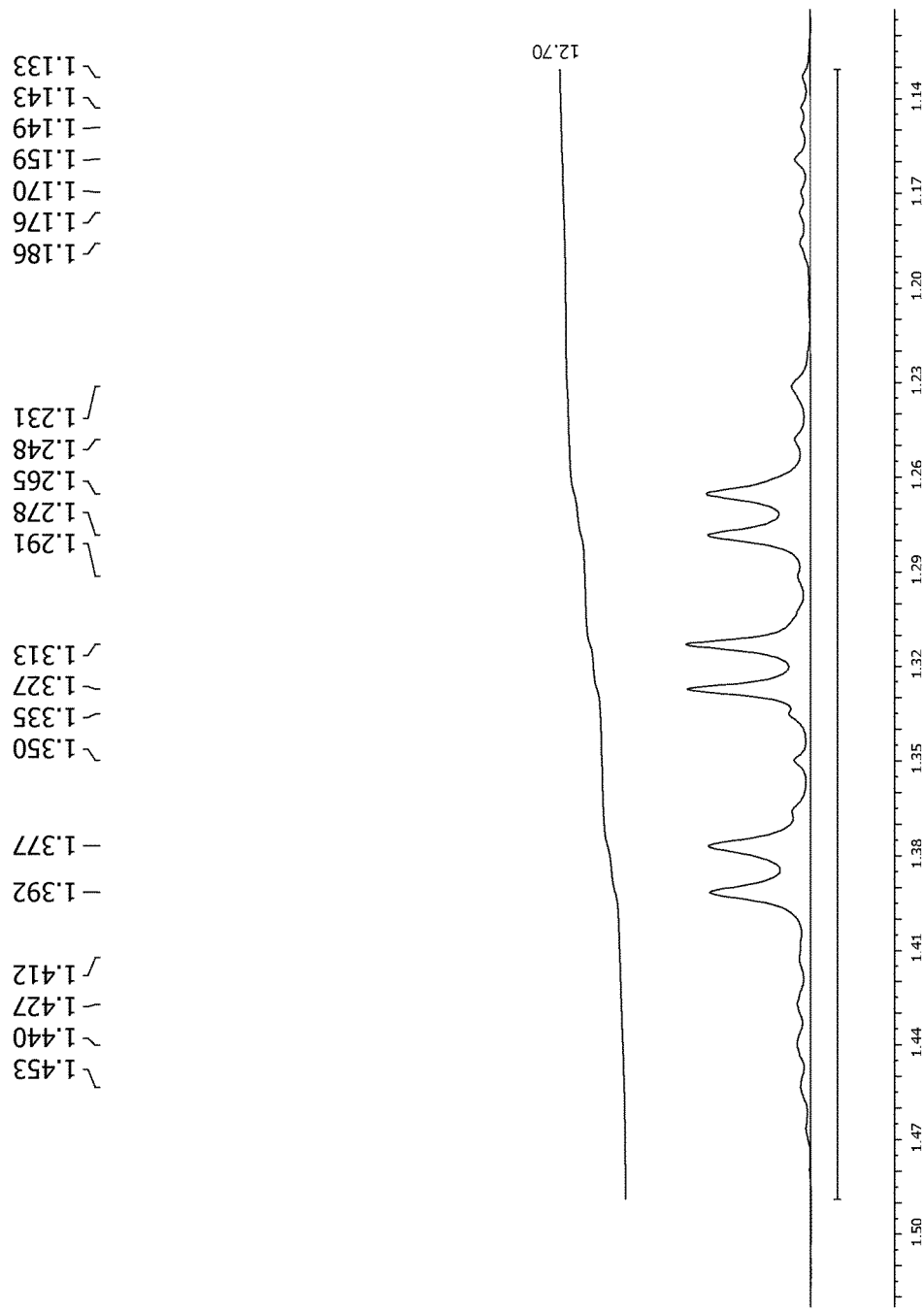
Figure 1:
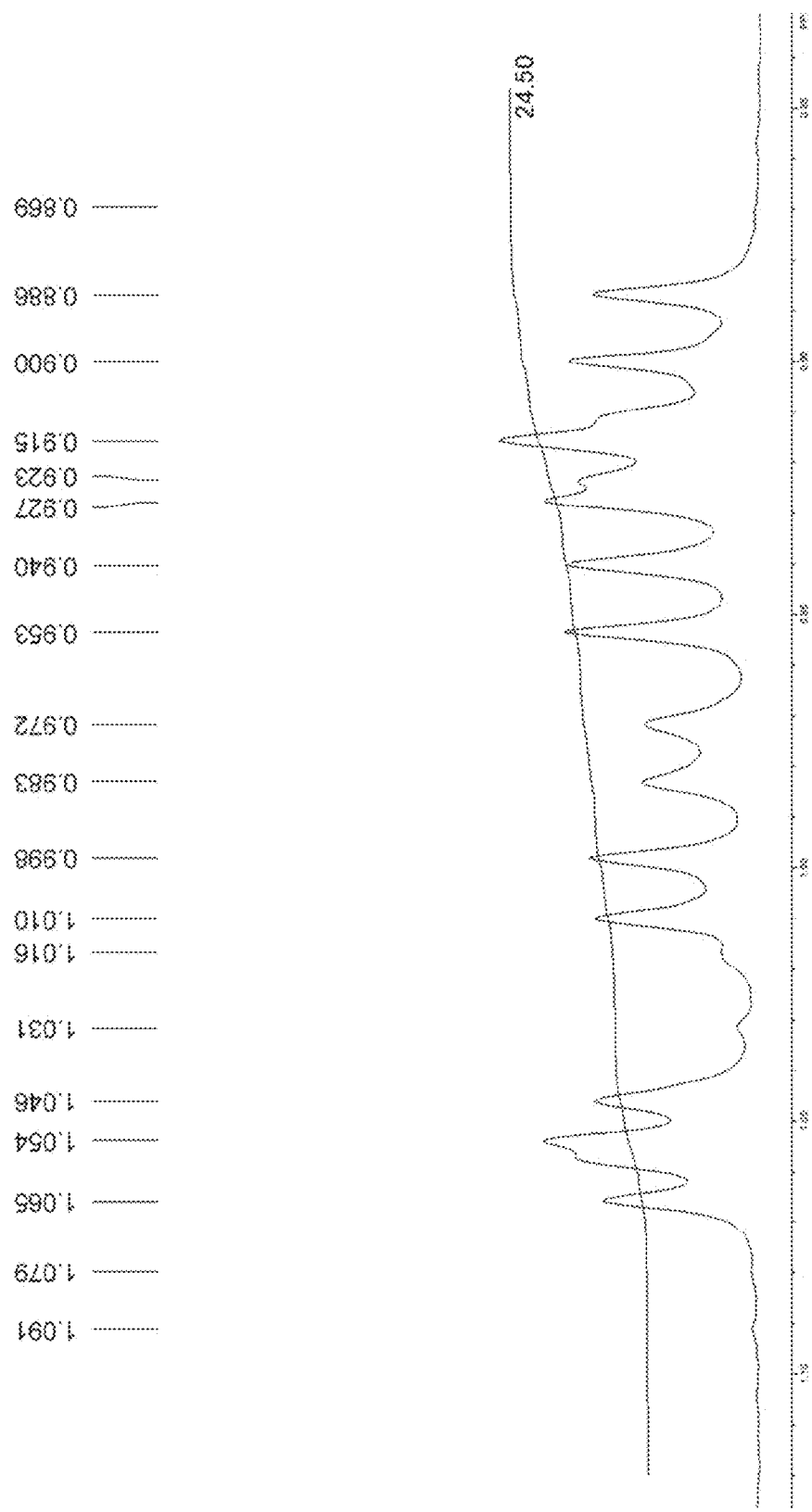
Figure 1:
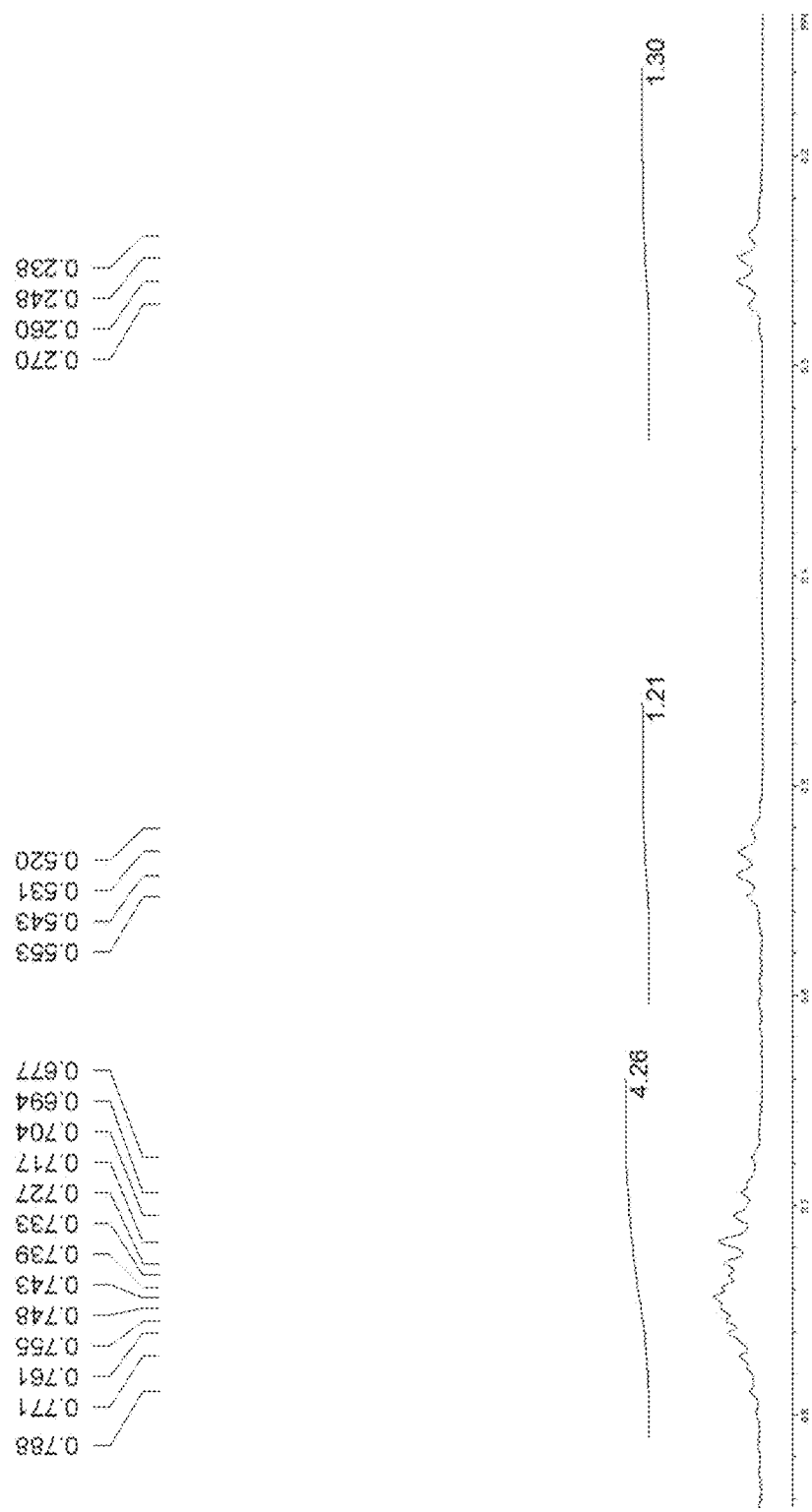
Figure 2:
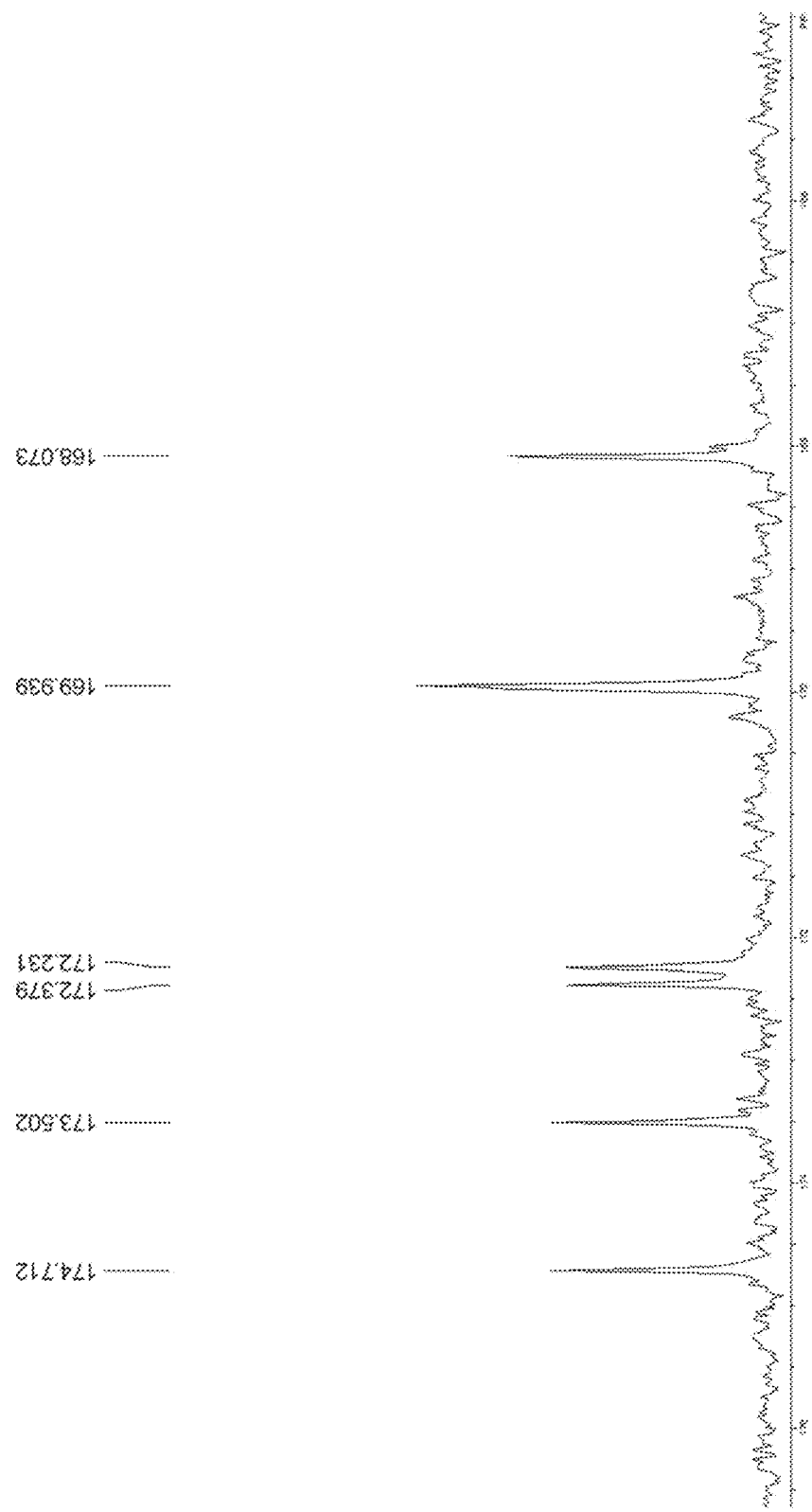
FIG. 2(A) shows $^{13}$C NMR data of 1 ($CDCl_3$).
FIG. 2(B) shows $^{13}$C NMR data of 1 ($CDCl_3$).
FIG. 2(C) shows $^{13}$C NMR data of 1 ($CDCl_3$).
FIG. 2(D) shows $^{13}$C NMR data of 1 ($CDCl_3$).
Figure 2:
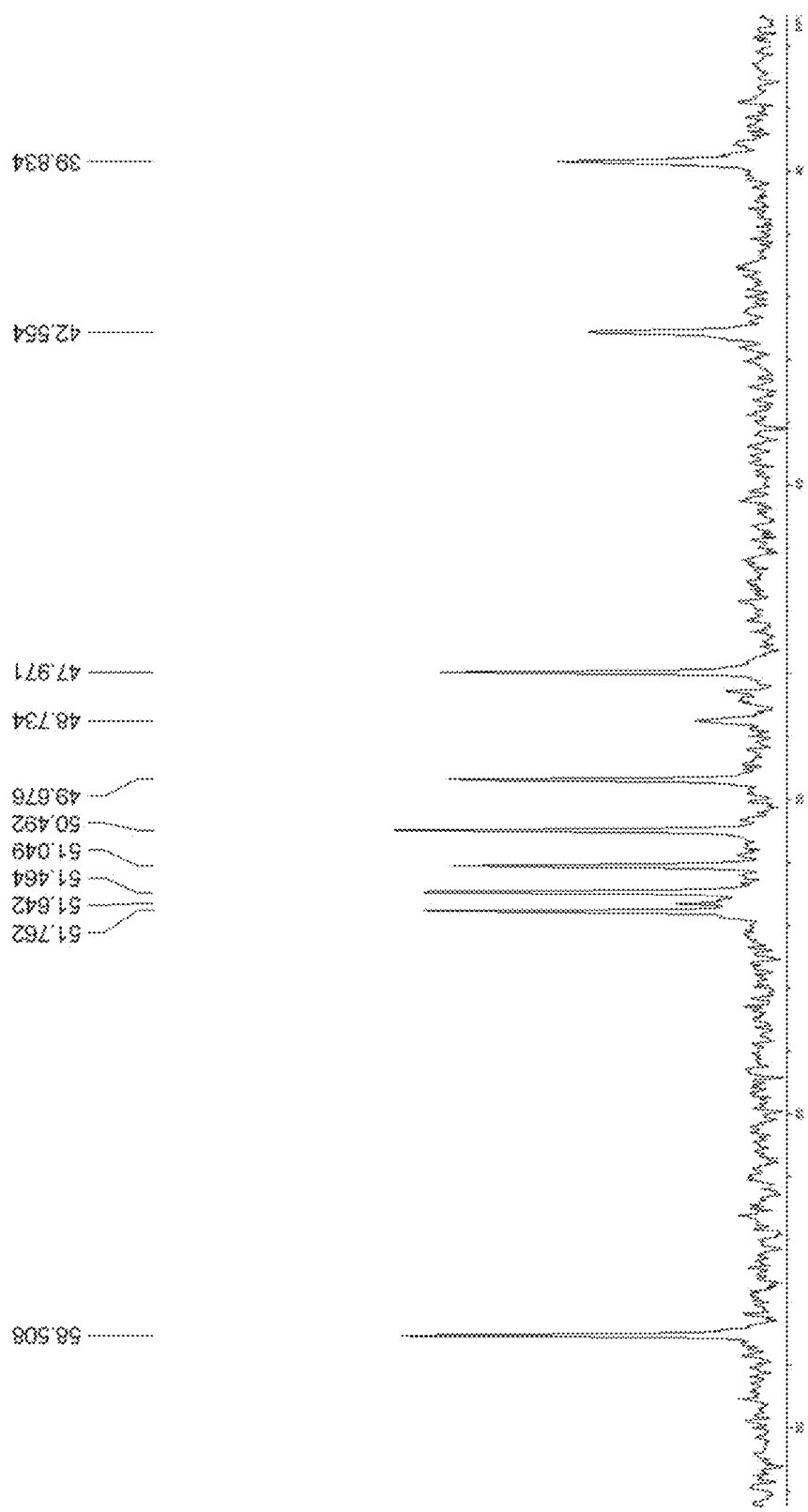
Figure 2:
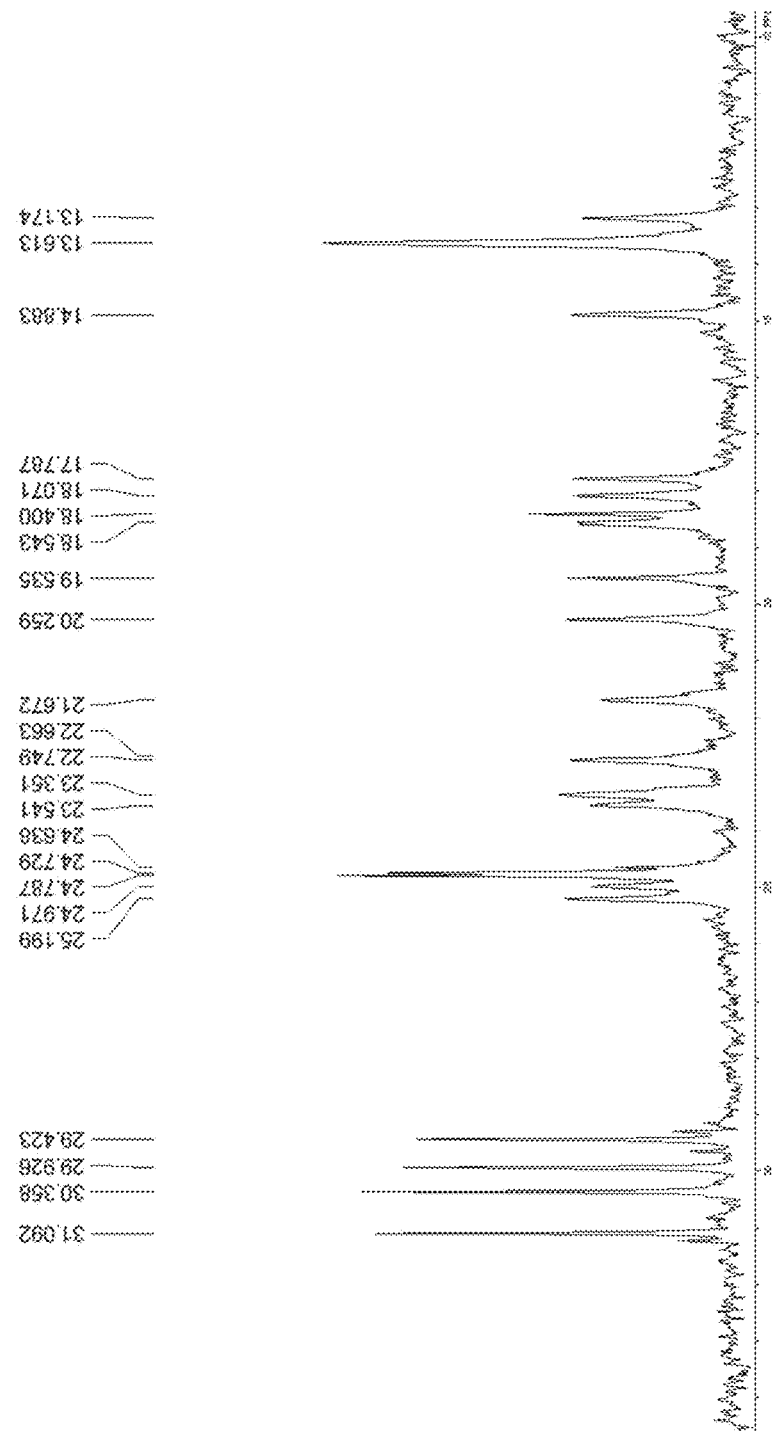
Figure 3:
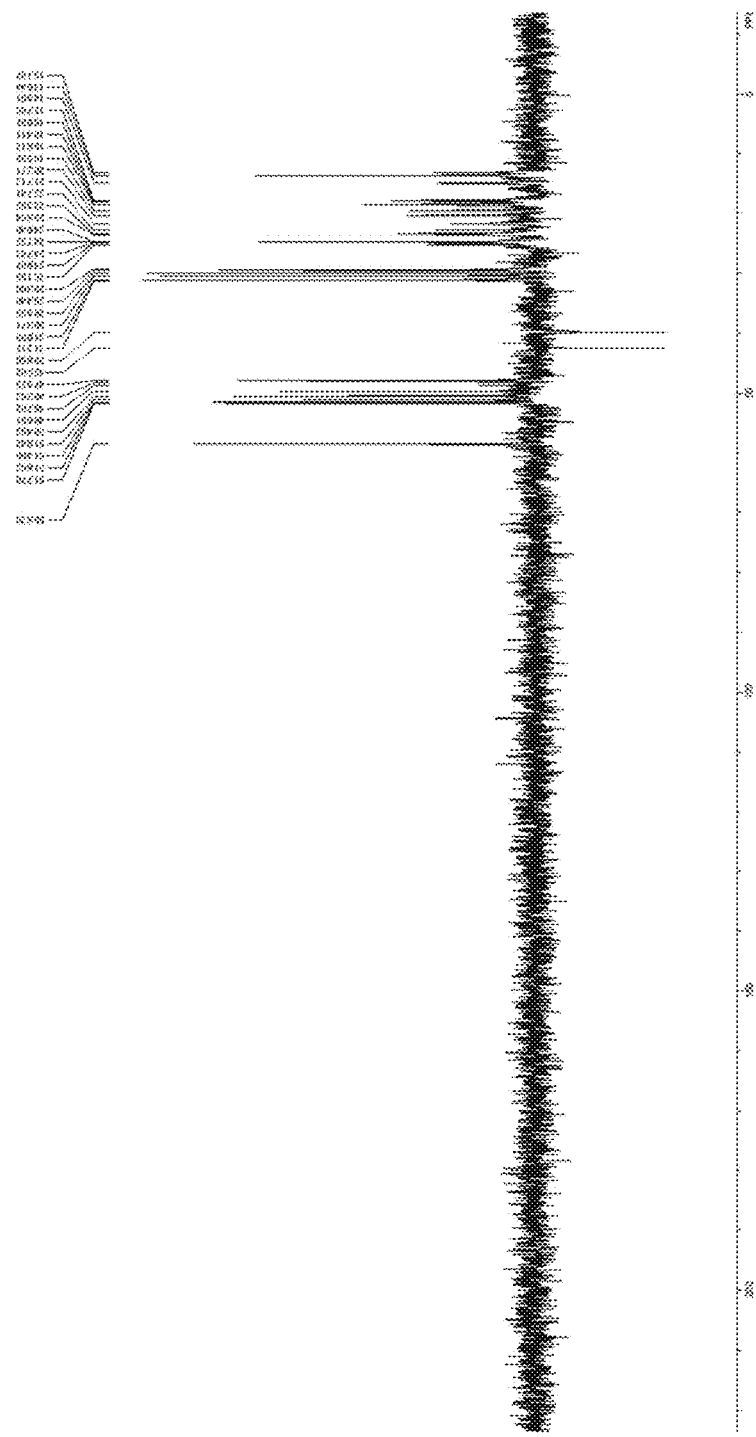
FIG. 3(A) shows DEPT-135 NMR data of 1 ($CDCl_3$).
FIG. 3(B) shows DEPT-135 NMR data of 1 ($CDCl_3$).
Figure 3:
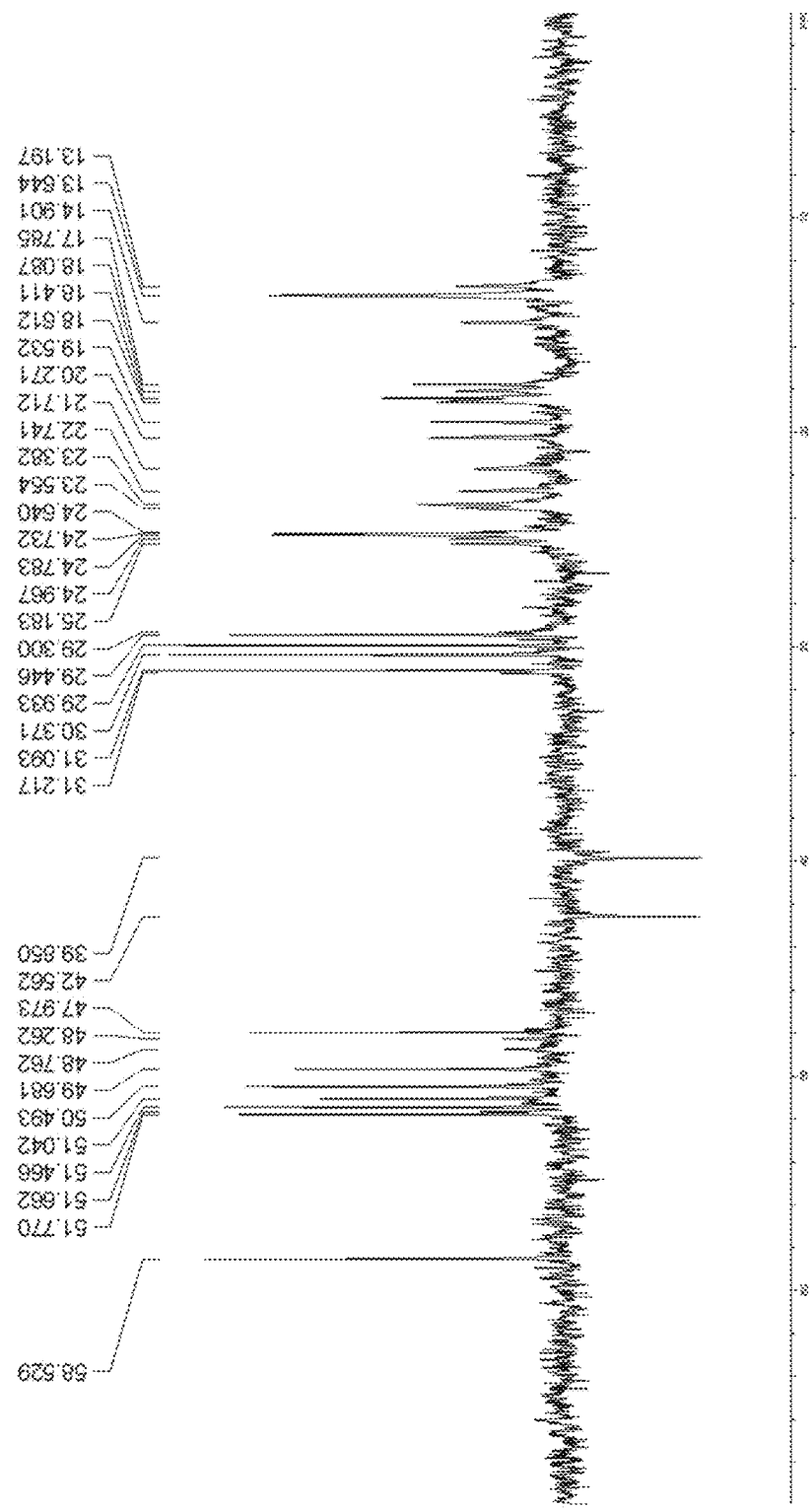
Figure 4:
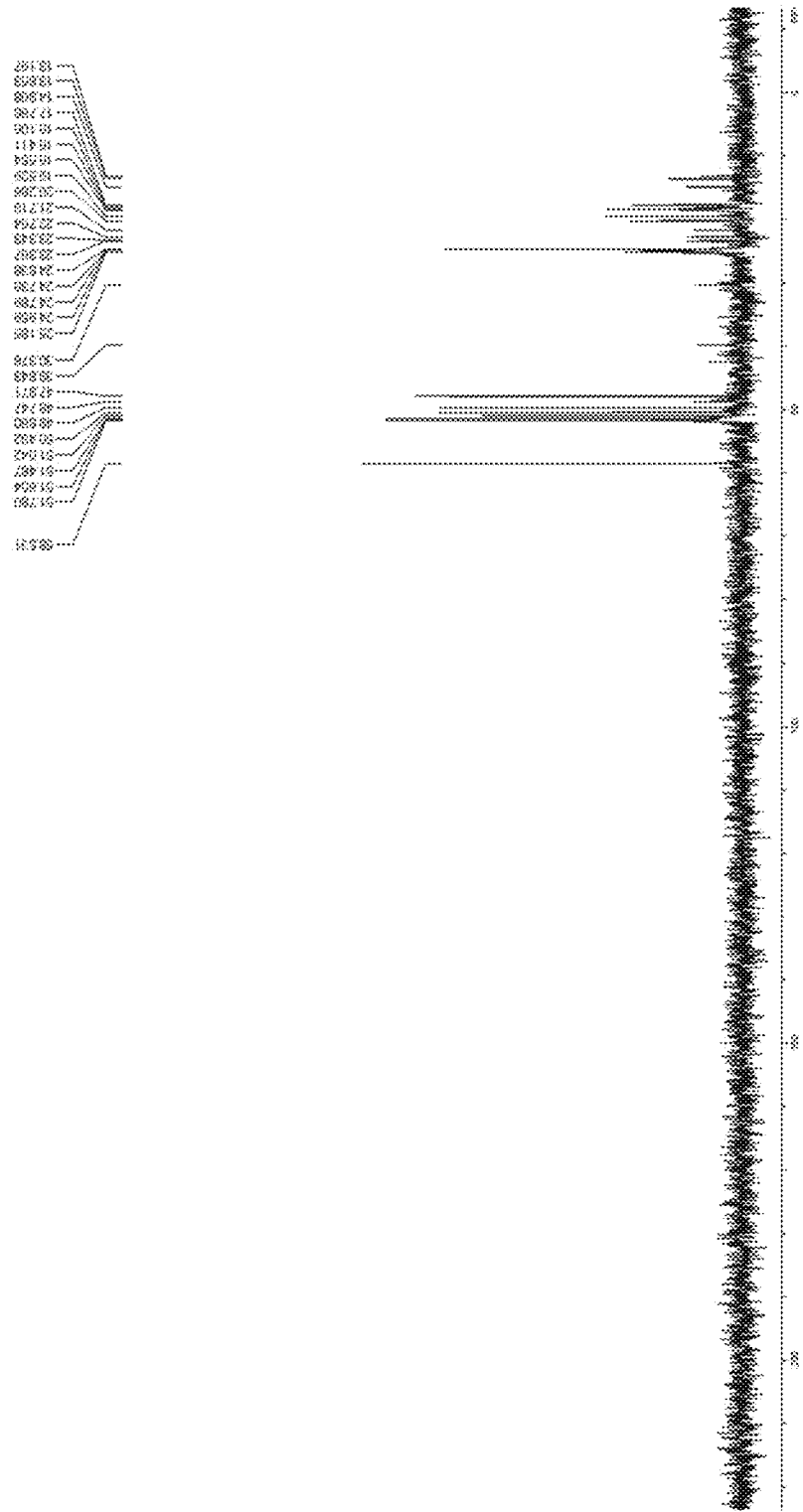
FIG. 4(A) shows DEPT-90 NMR data of 1 ($CDCl_3$).
FIG. 4(B) shows DEPT-90 NMR data of 1.
Figure 4:
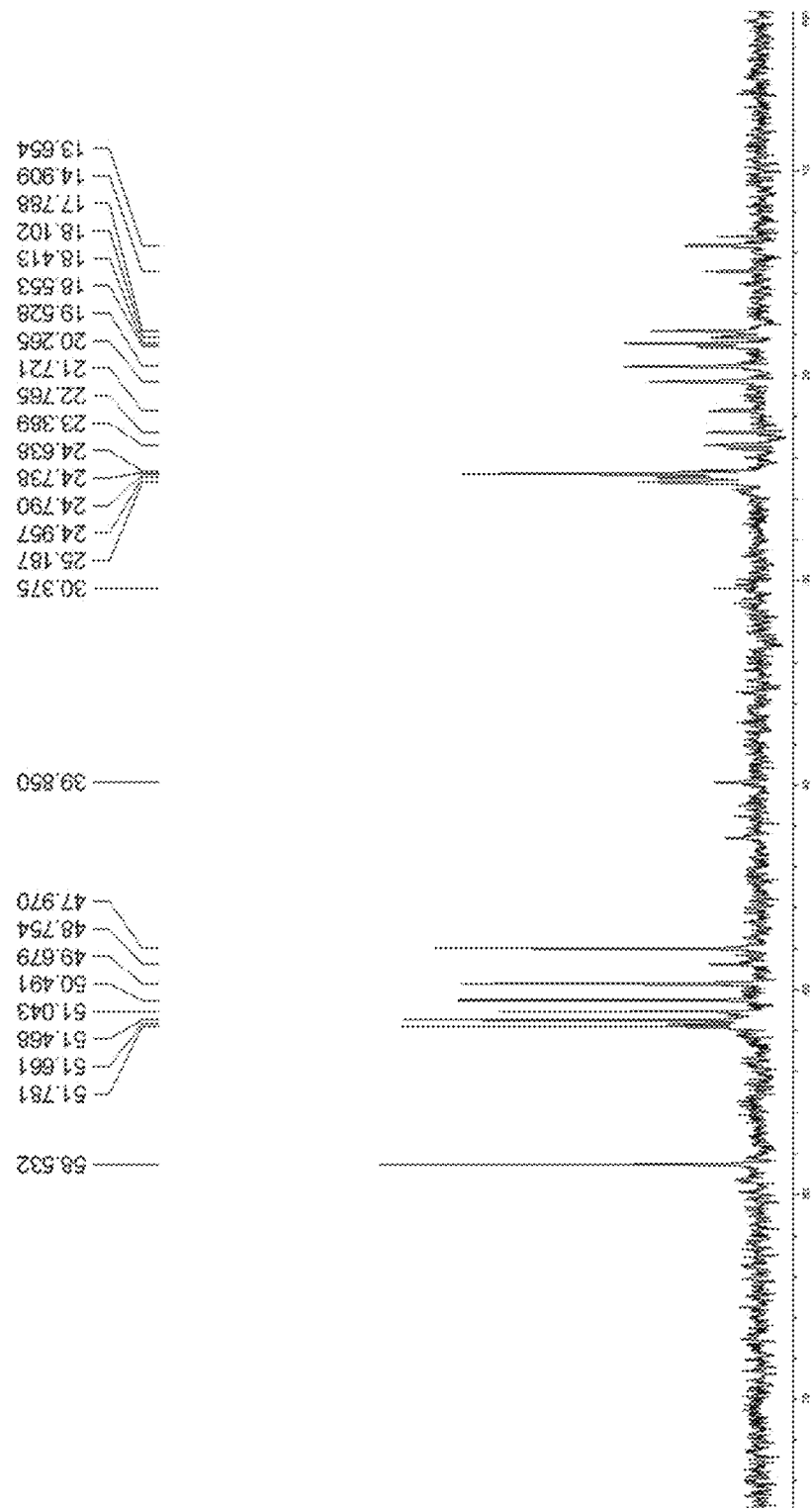
Figure 5A:
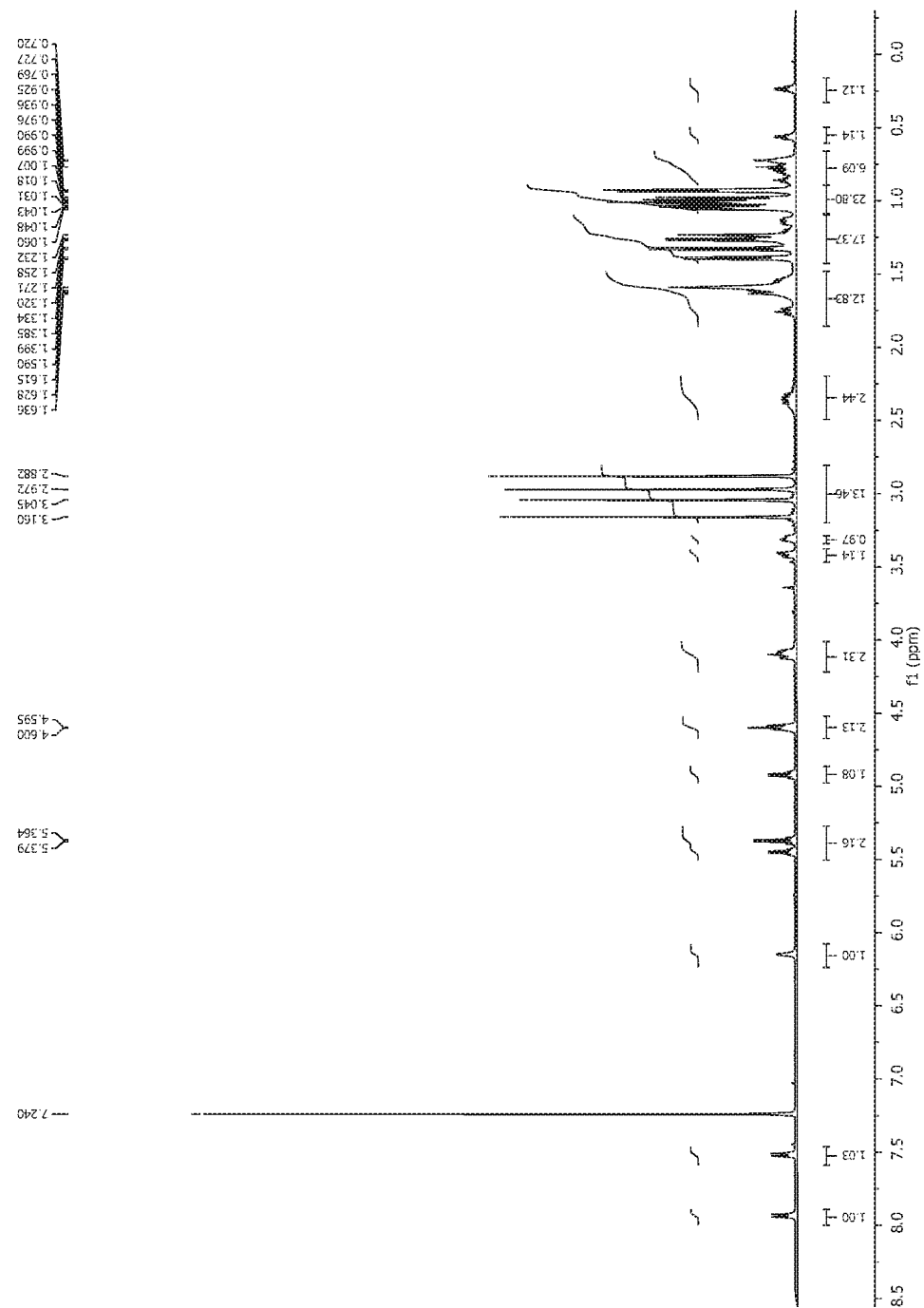
FIG. 5(A) shows $^1$H NMR data of 2 ($CDCl_3$).
Figure 5B:
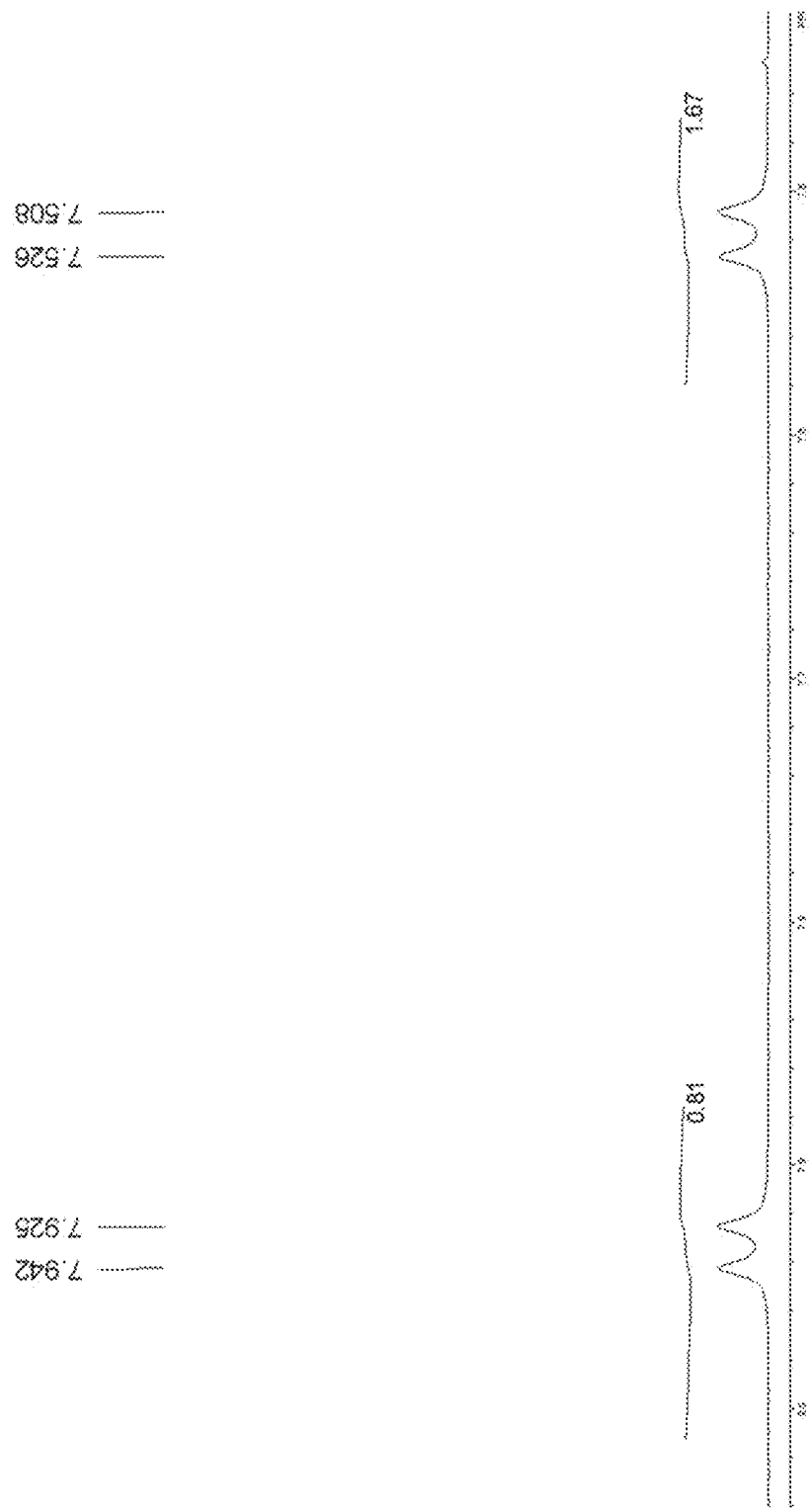
FIG. 5(B) shows $^1$H NMR data of 2 ($CDCl_3$).
Figure 5:
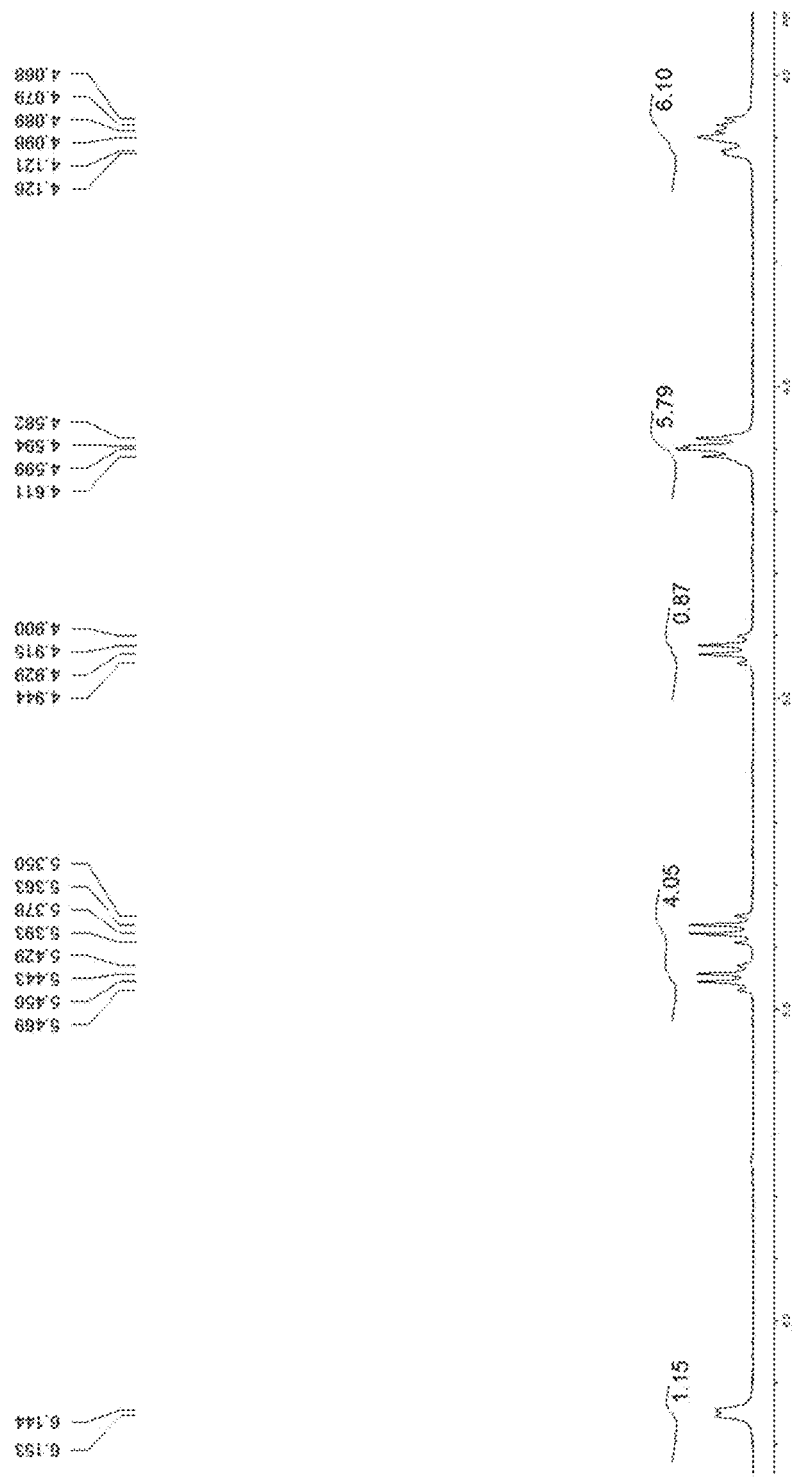
FIG. 5(C) shows $^1$H NMR data of 2 ($CDCl_3$).
FIG. 5(D) shows $^1$H NMR data of 2 ($CDCl_3$).
FIG. 5(E) shows $^1$H NMR data of 2 ($CDCl_3$).
FIG. 5(F) shows $^1$H NMR data of 2 (CDCl$_3$).
Figure 5:
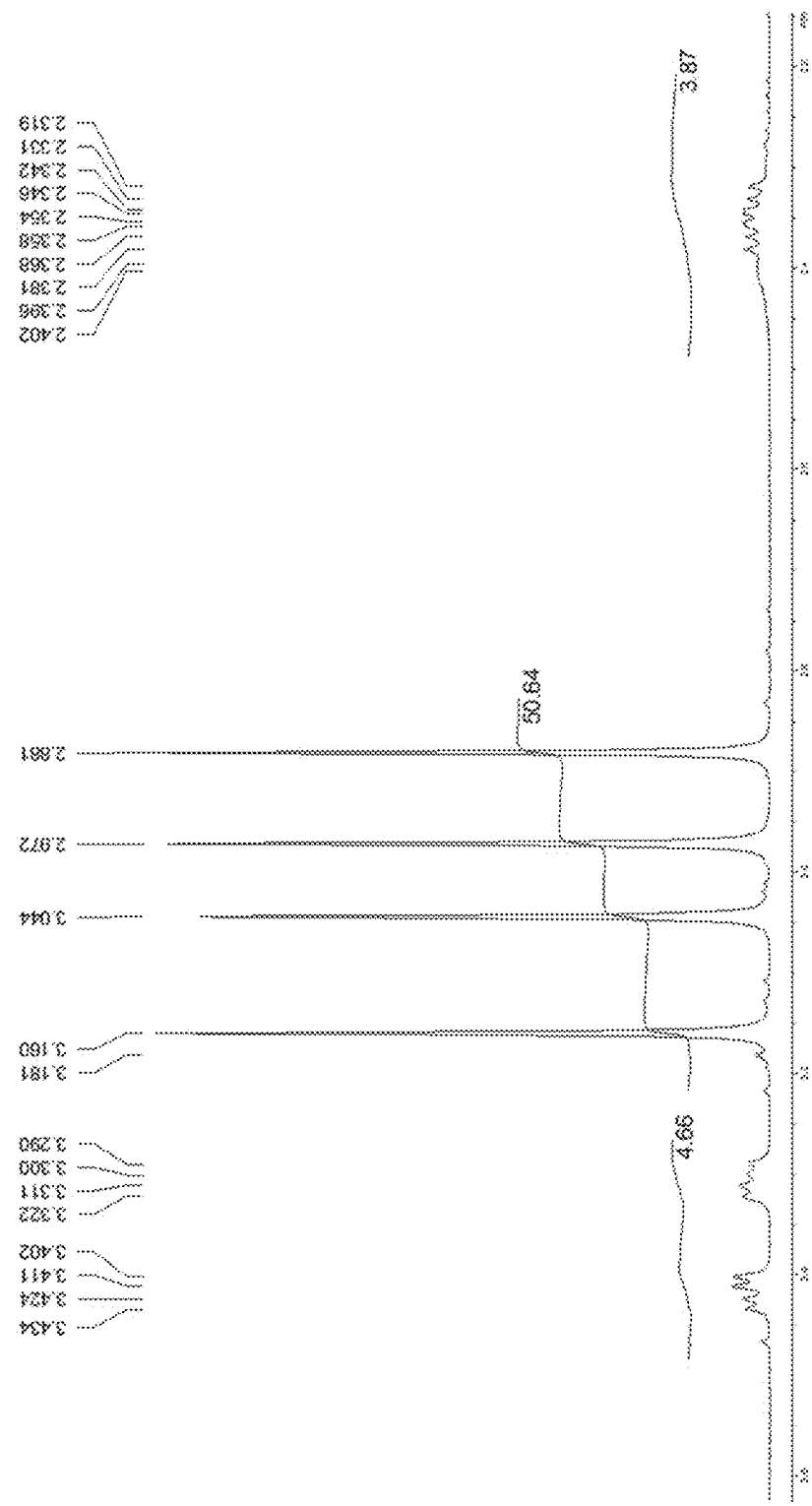
Figure 5:
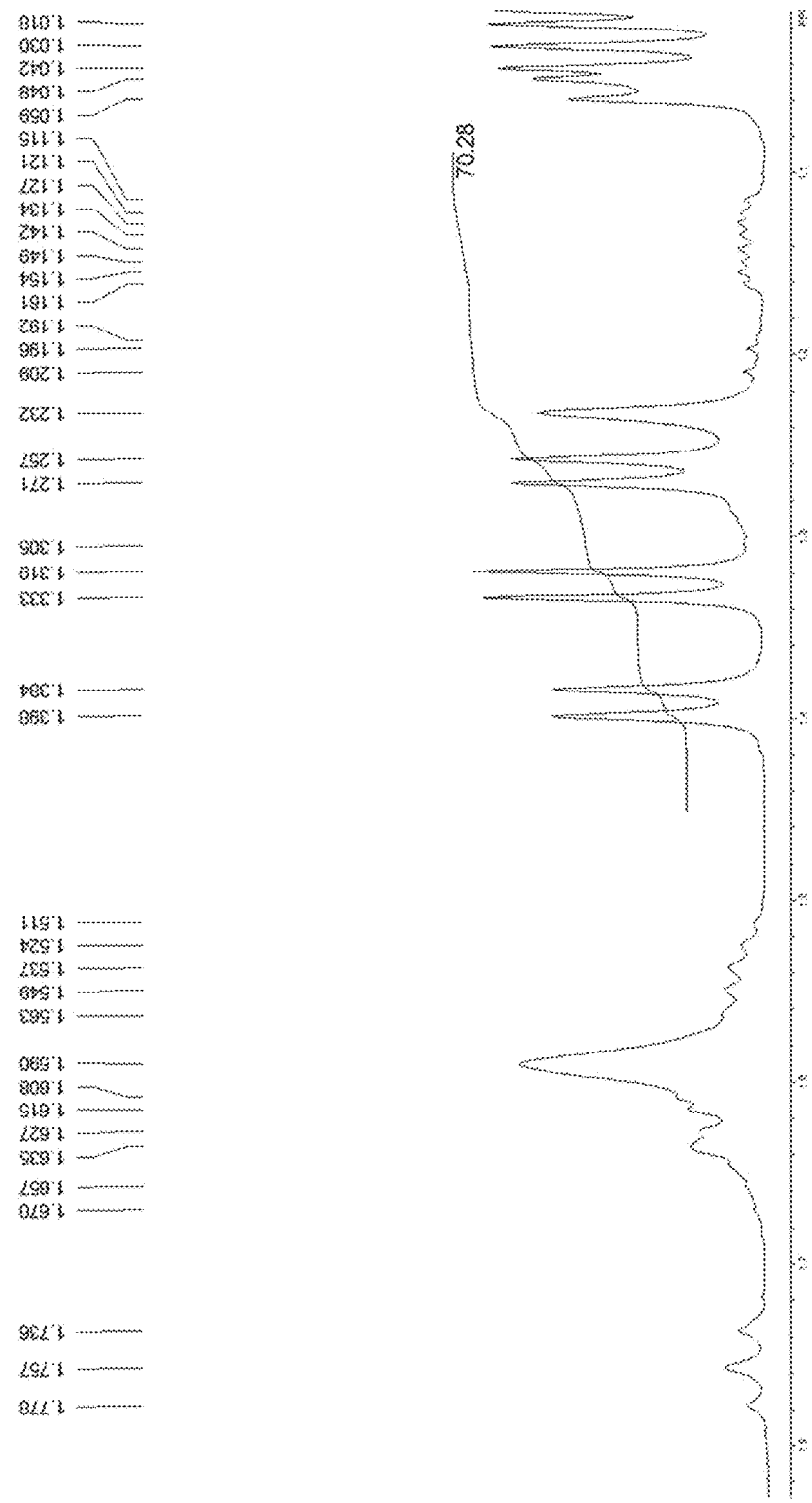
Figure 5:
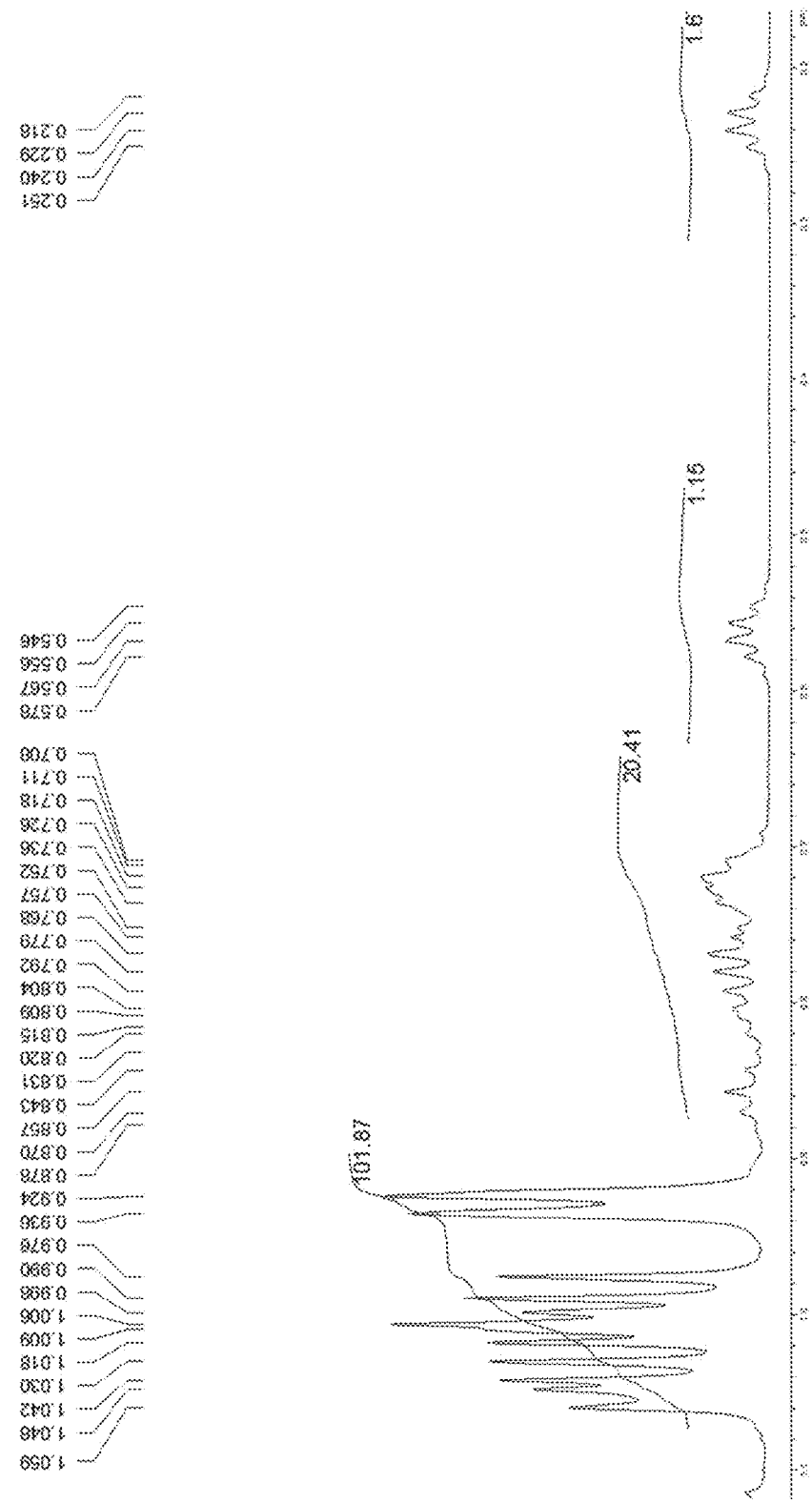
Figure 6:
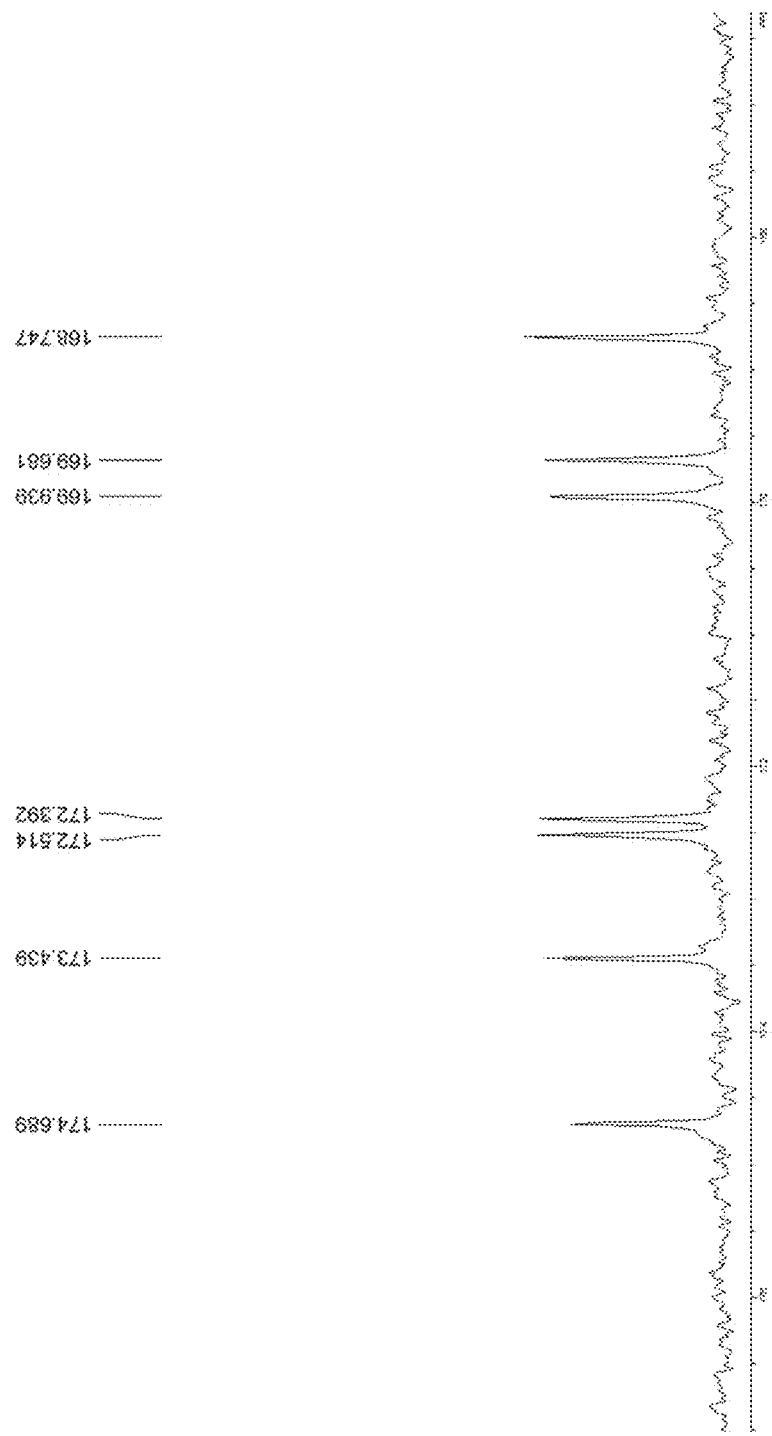
FIG. 6(A) shows $^{13}$C NMR data of 2 (CDCl$_3$).
FIG. 6(B) shows $^{13}$C NMR data of 2 (CDCl$_3$).
FIG. 6(C) shows $^{13}$C NMR data of 2 (CDCl$_3$).
FIG. 6(D) shows $^{13}$C NMR data of 2 (CDCl$_3$).
Figure 6:
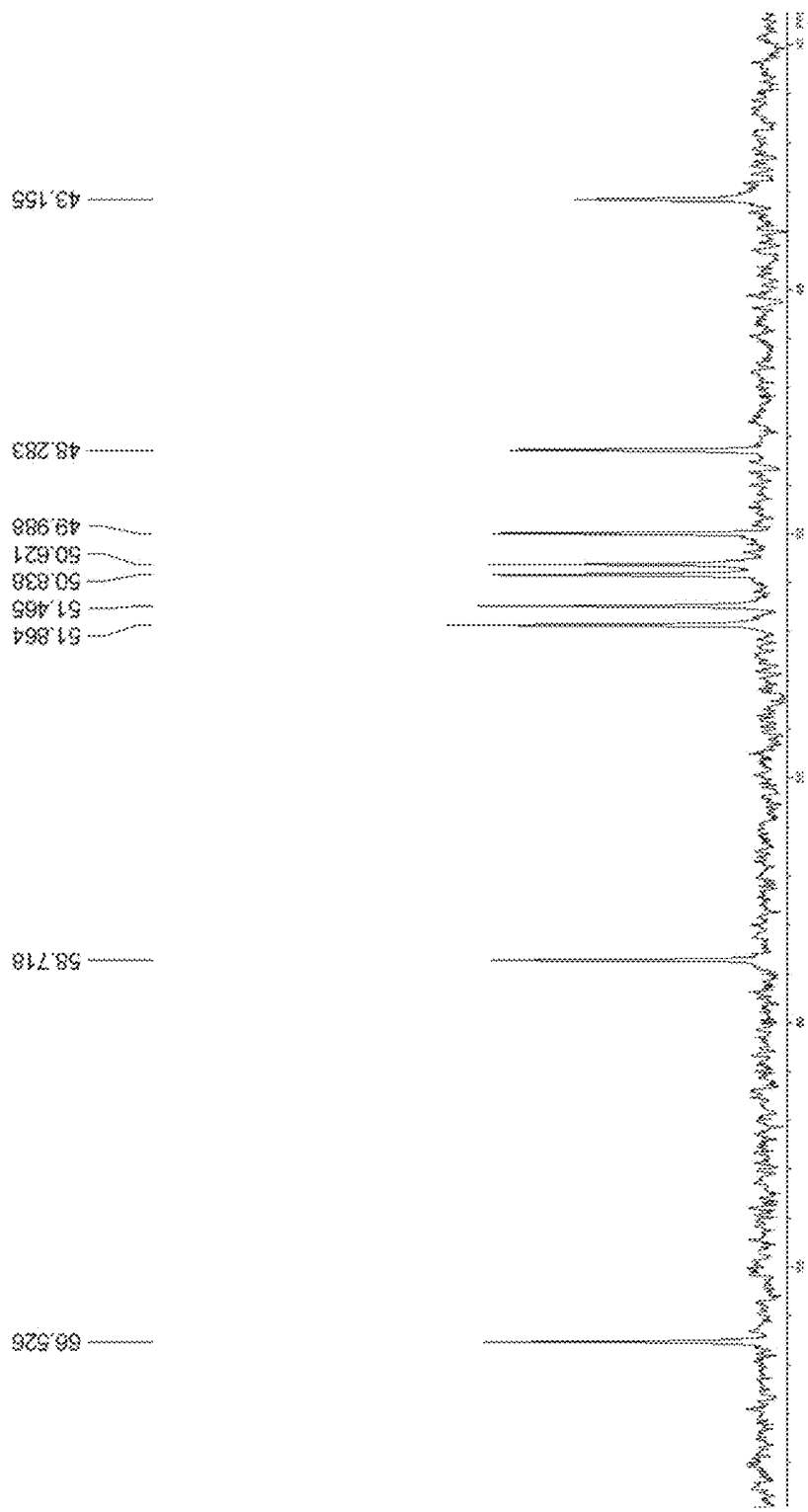
Figure 6:
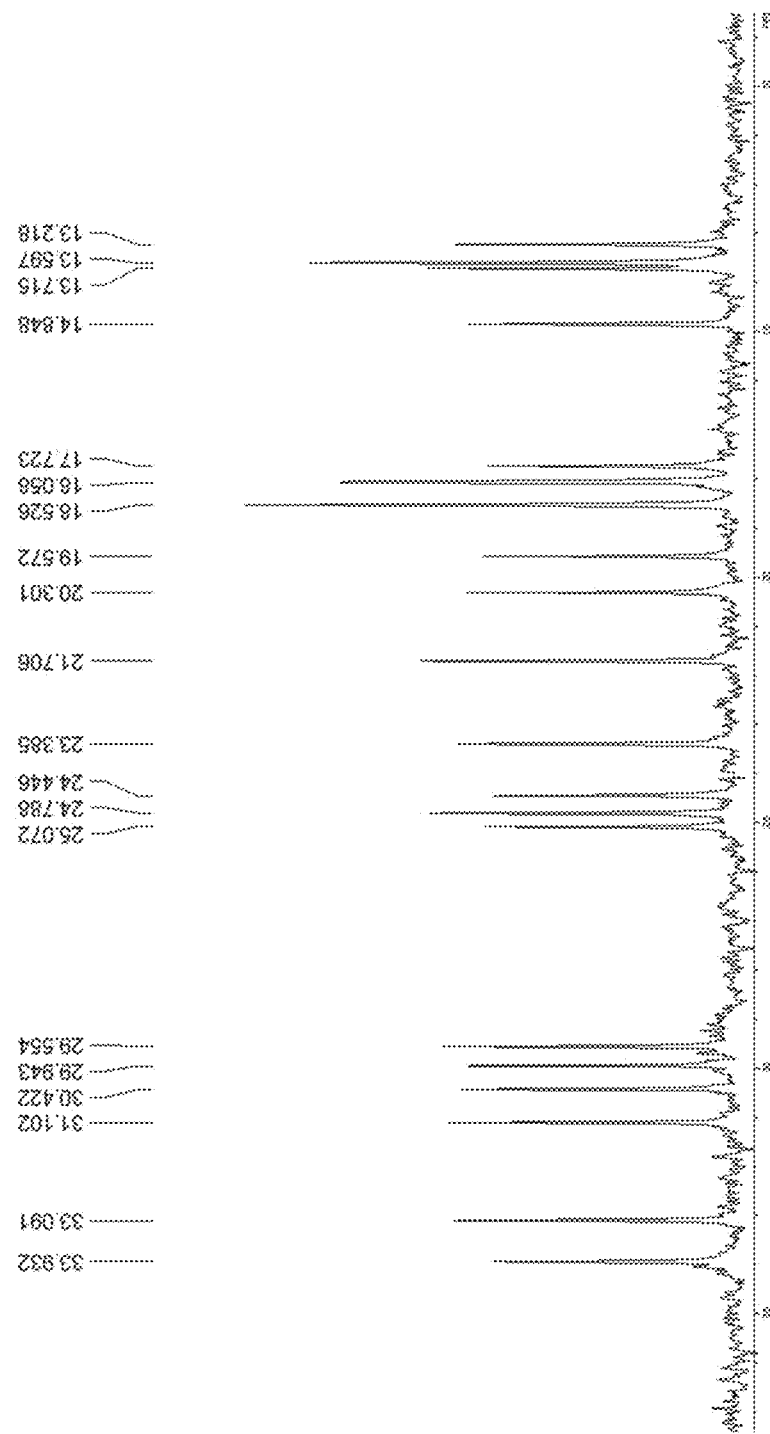
Figure 7:
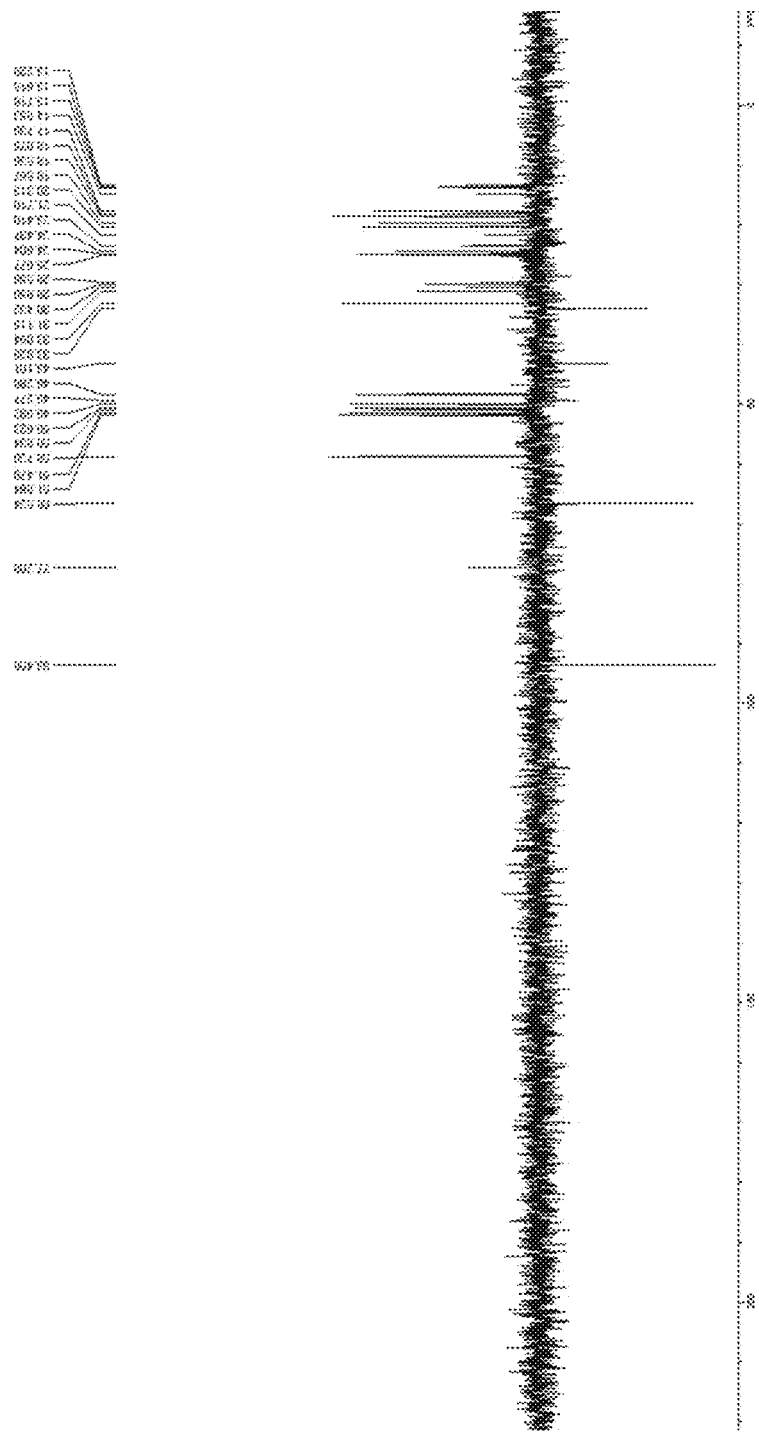
FIG. 7(A) shows DEPT-135 NMR data of 2 (CDCl$_3$).
FIG. 7(B) shows DEPT-135 NMR data of 2 (CDCl$_3$).
Figure 7:
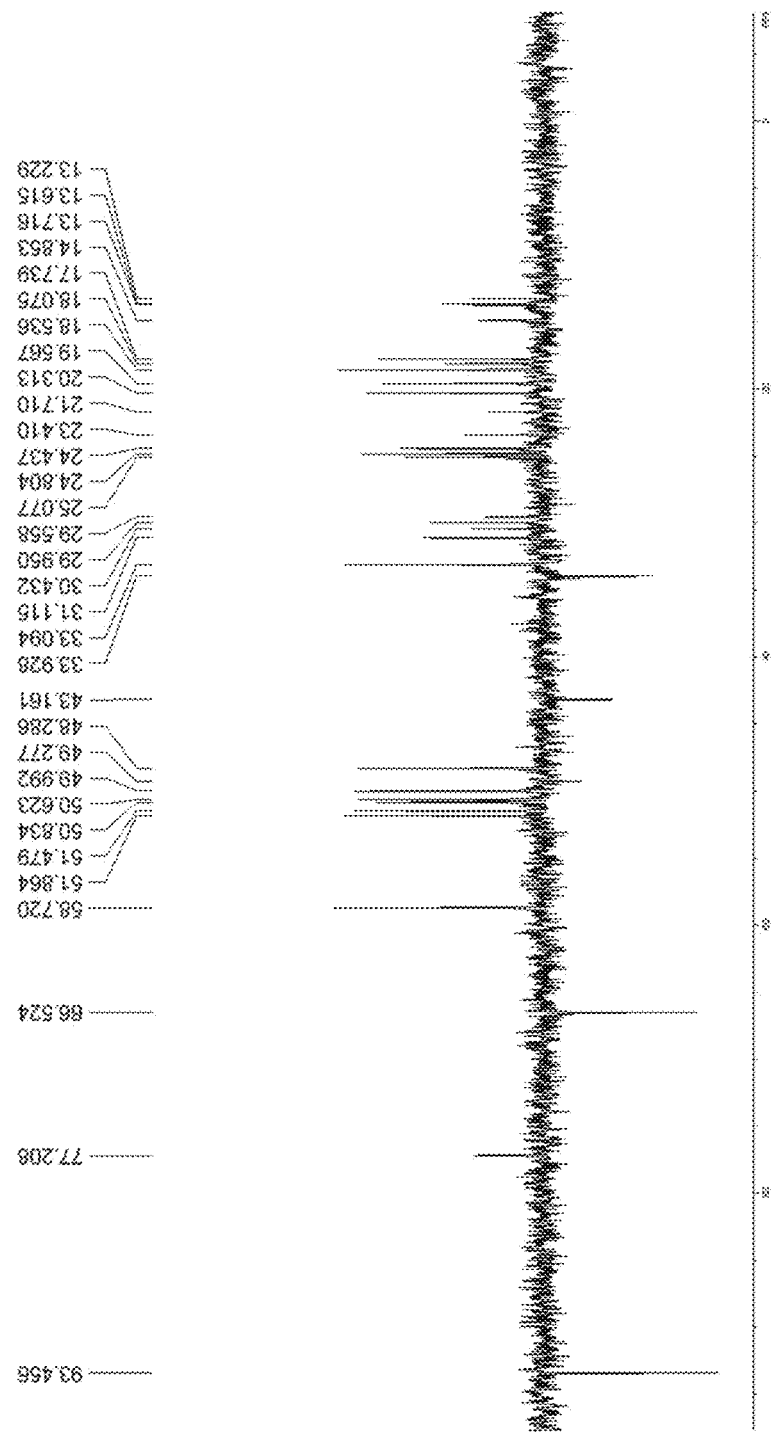
Figure 8:
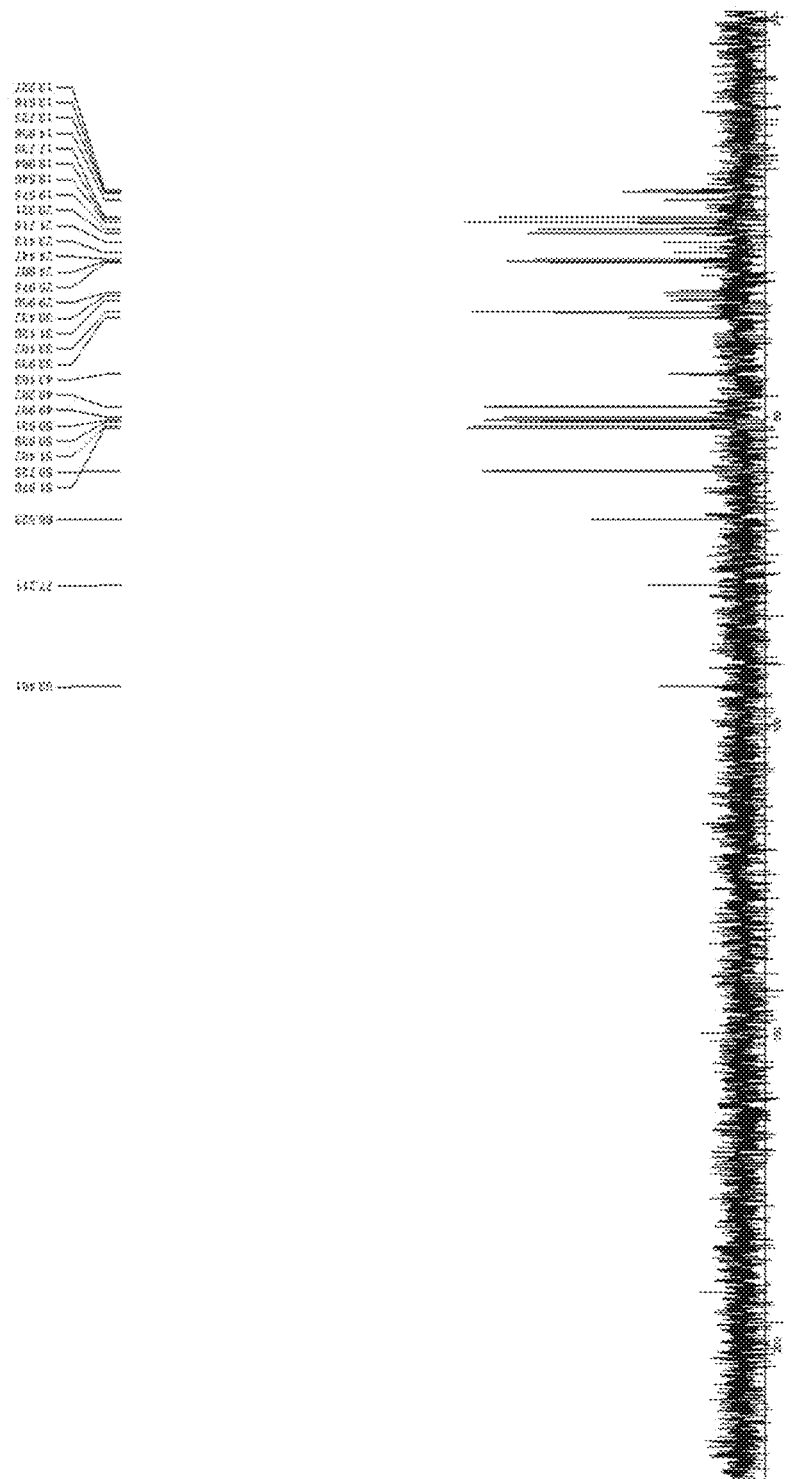
FIG. 8(A) shows DEPT-90 NMR data of 2 (CDCl$_3$).
FIG. 8(B) shows DEPT-90 NMR data of 2.
Figure 8:
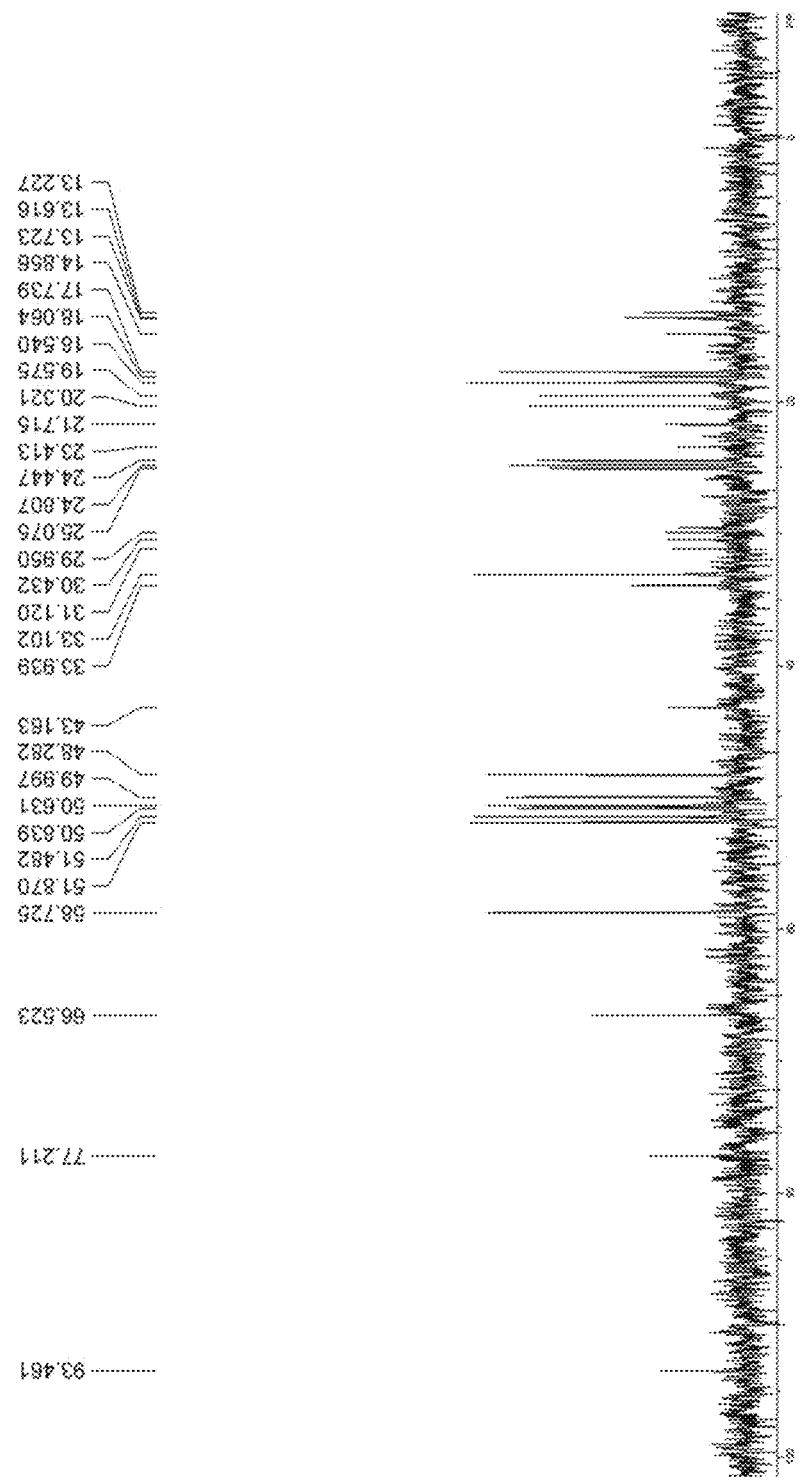
Figure 9:
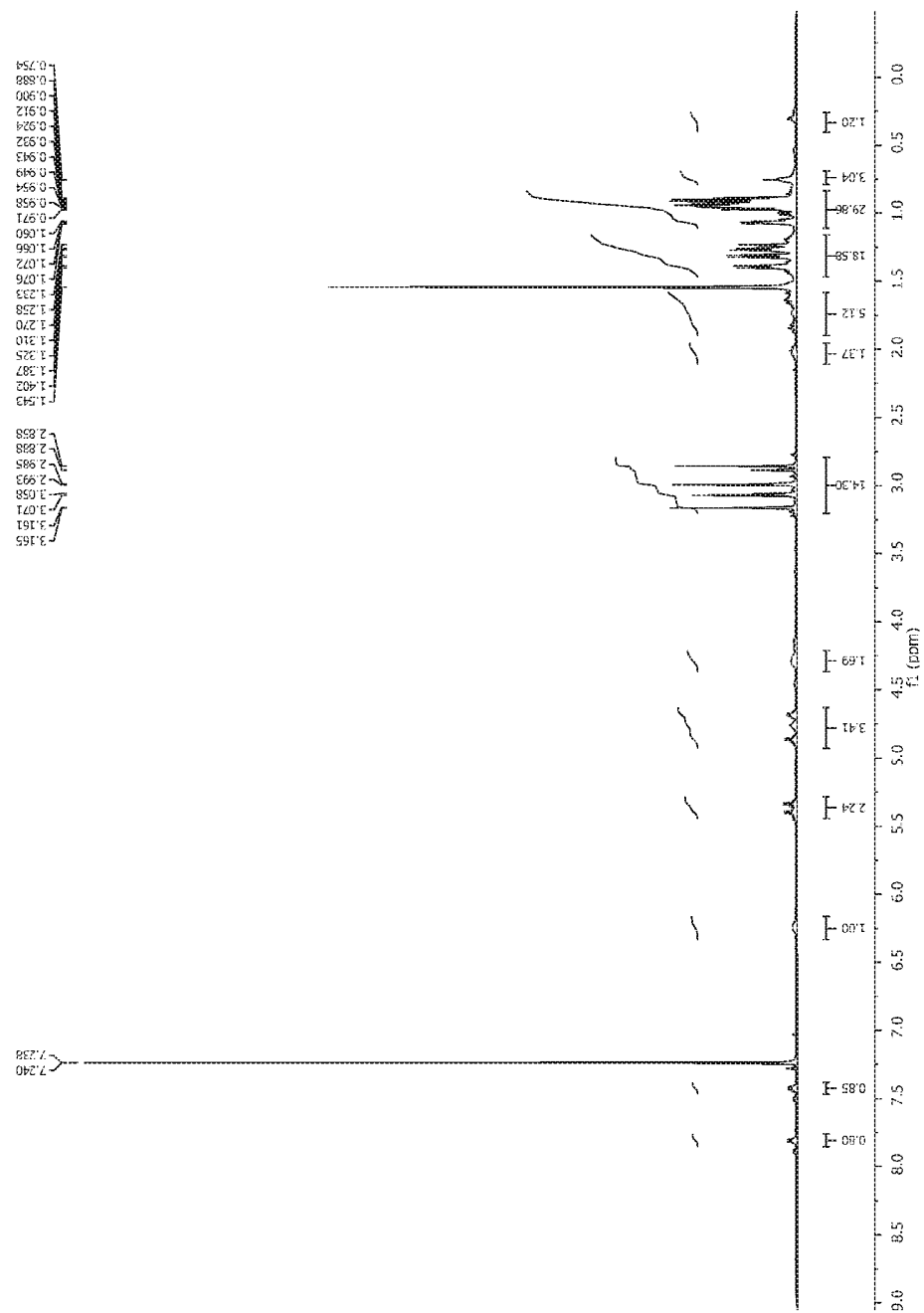
FIG. 9(A) shows $^1$H NMR data of 3 (CDCl$_3$).
FIG. 9(B) shows $^1$H NMR data of 3 (CDCl$_3$).
FIG. 9(C) shows $^1$H NMR data of 3 (CDCl$_3$).
FIG. 9(D) shows $^1$H NMR data of 3 (CDCl$_3$).
FIG. 9(E) shows $^1$H NMR data of 3 (CDCl$_3$).
FIG. 9(F) shows $^1$H NMR data of 3 (CDCl$_3$).
FIG. 9(G) shows $^1$H NMR data of 3 (CDCl$_3$).
Figure 9:
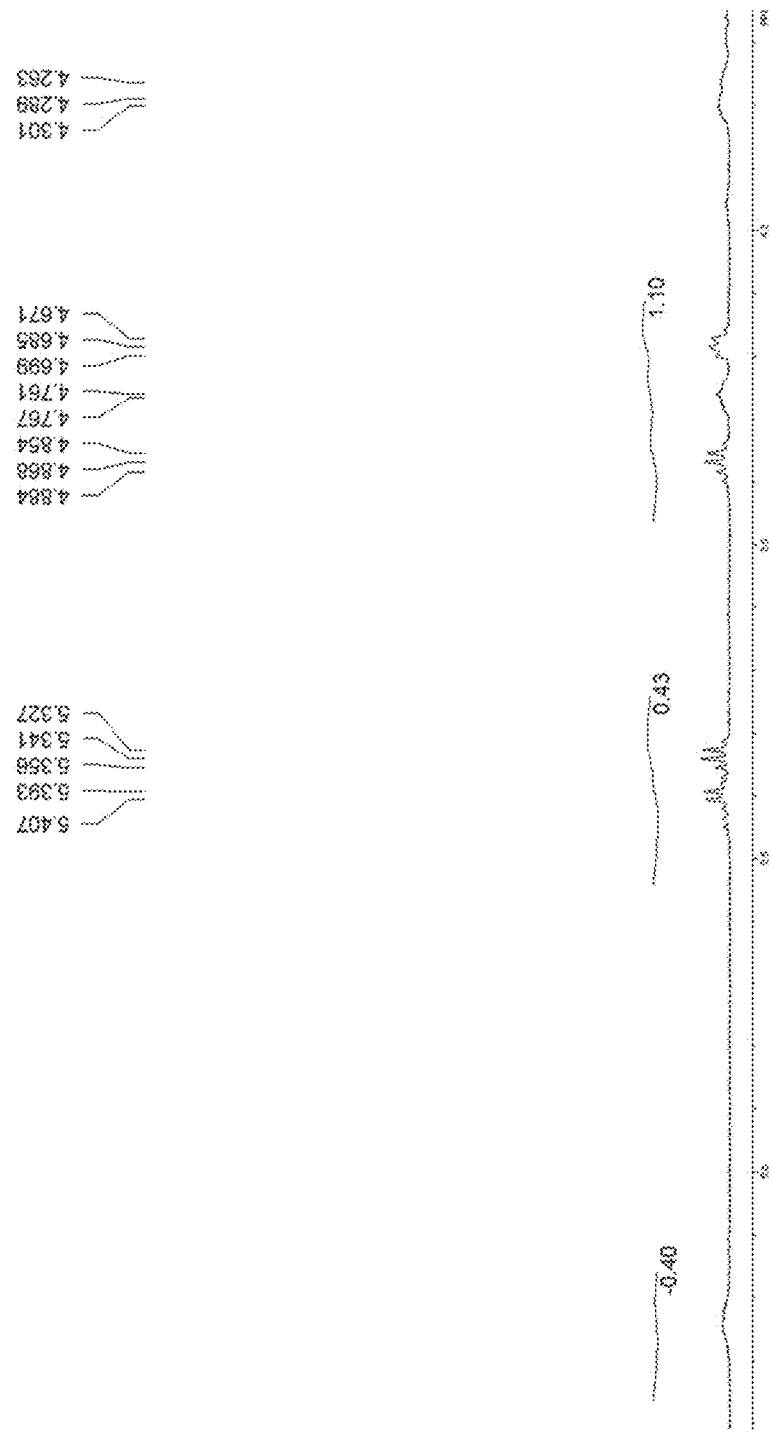
Figure 9:
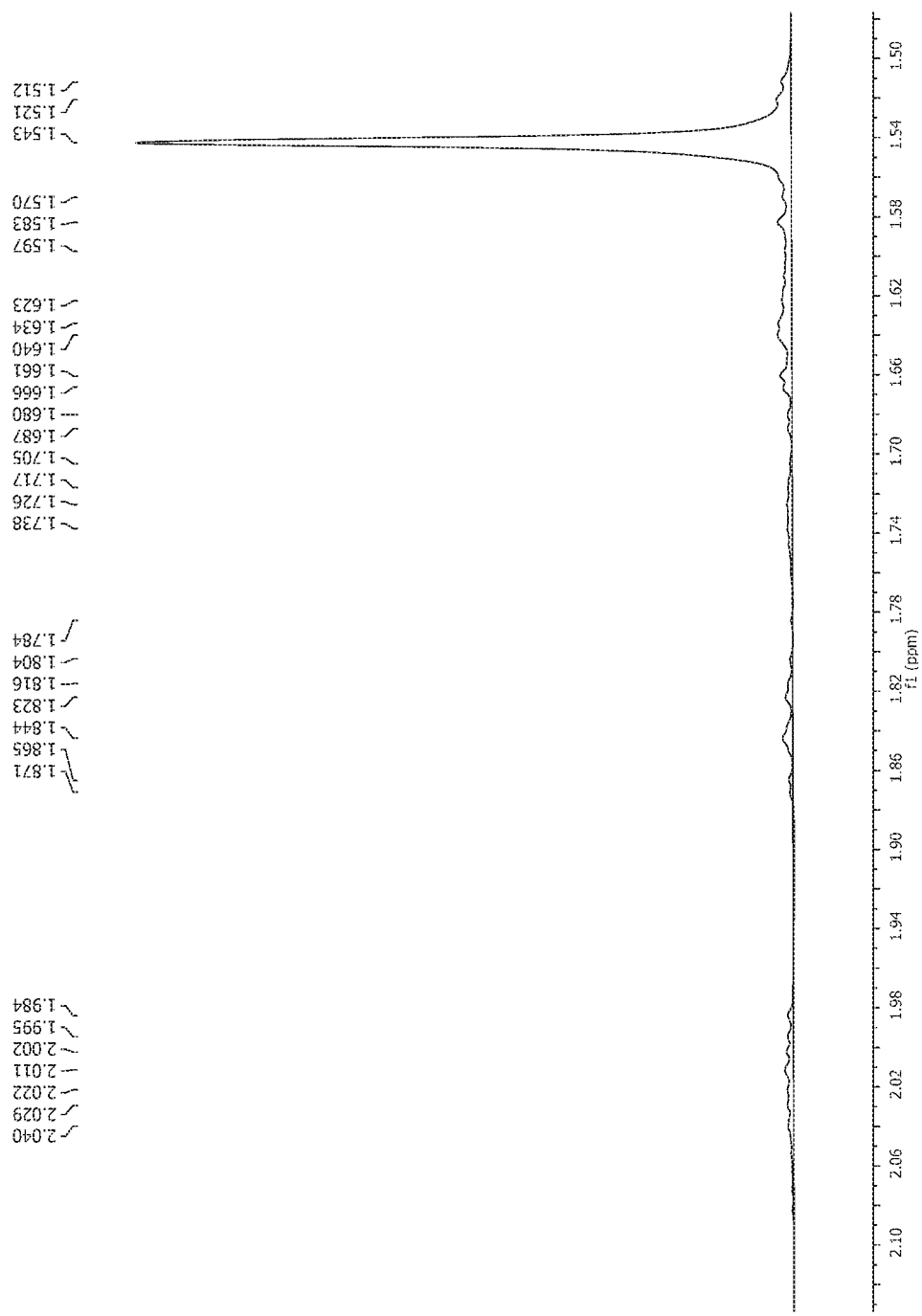
Figure 9:
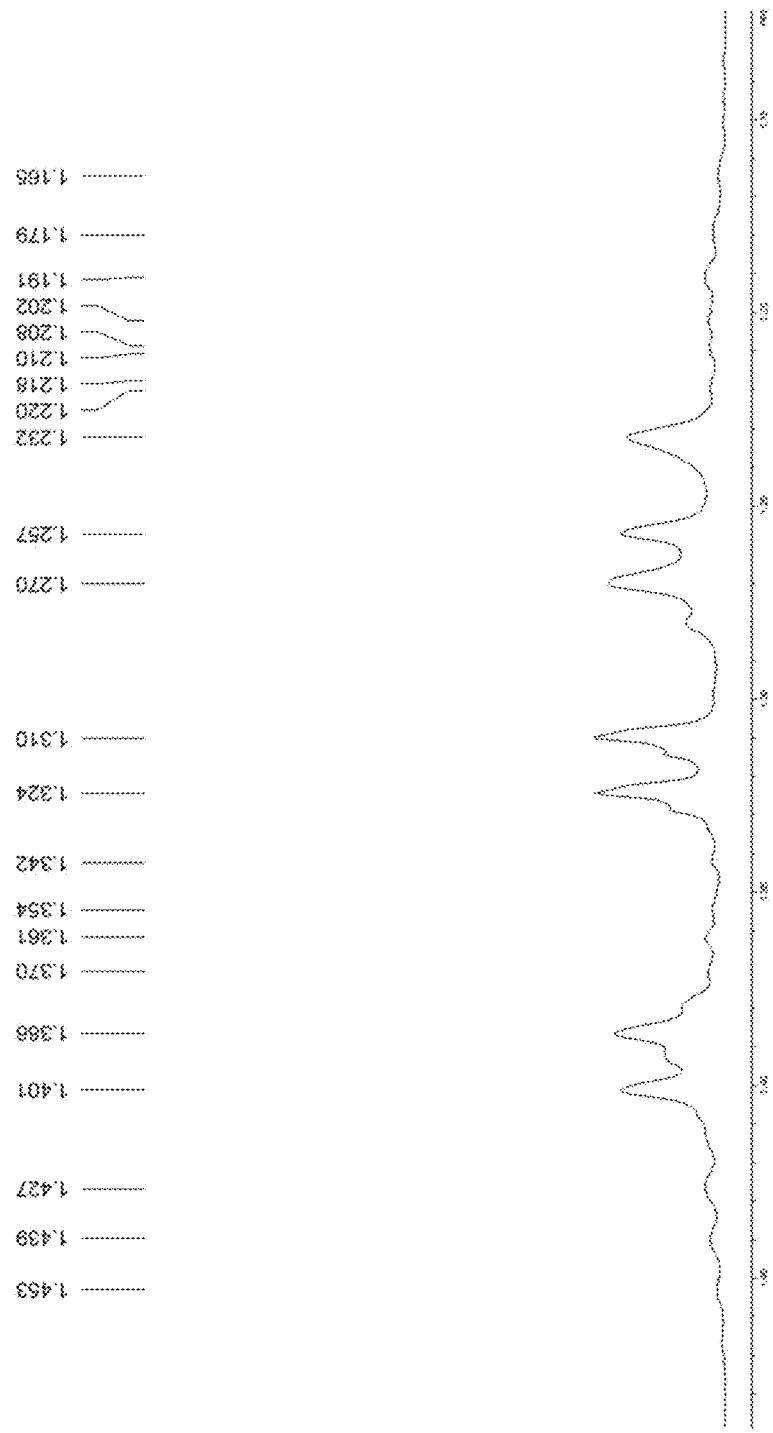
Figure 9:
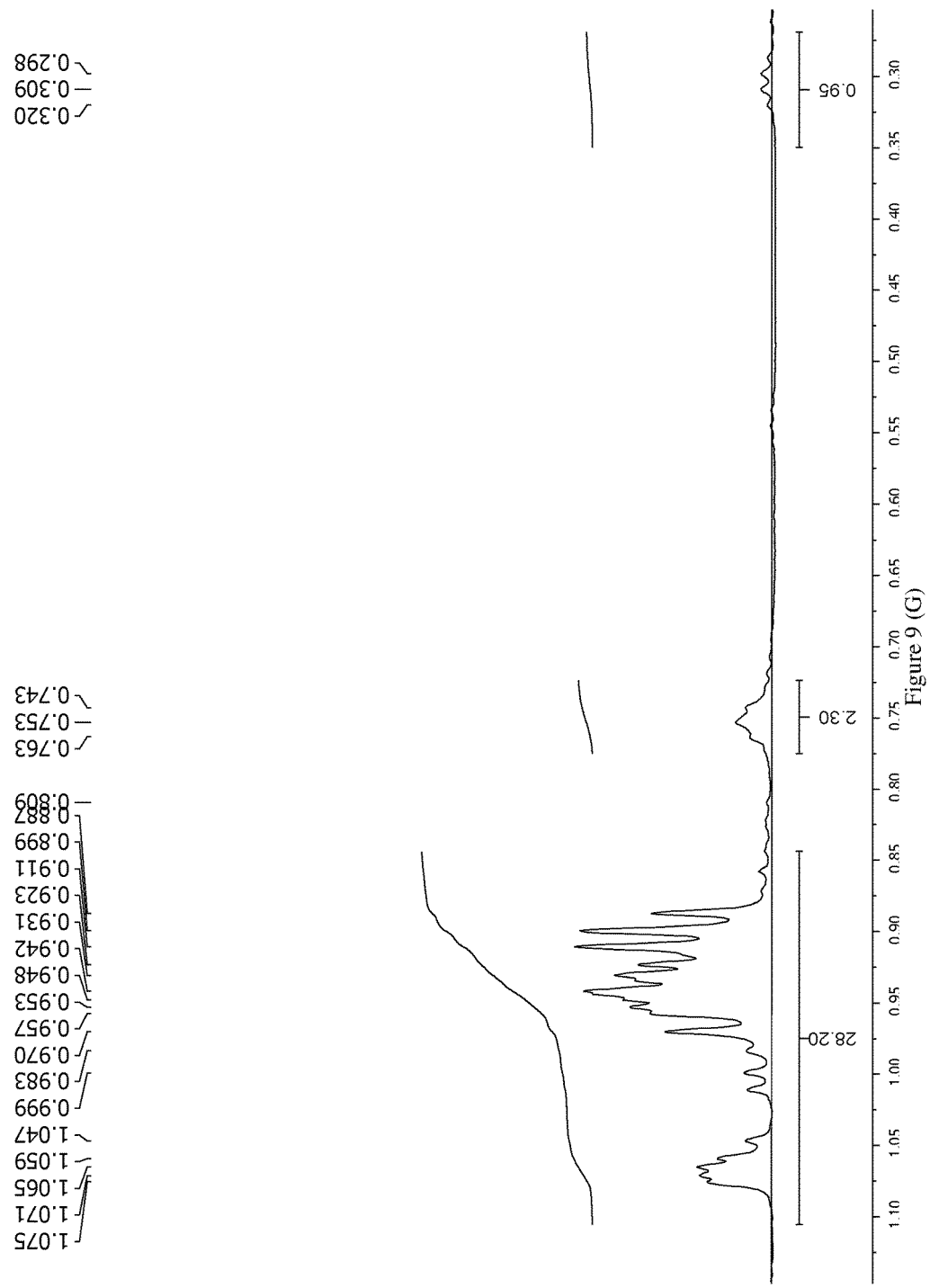
Figure 10:
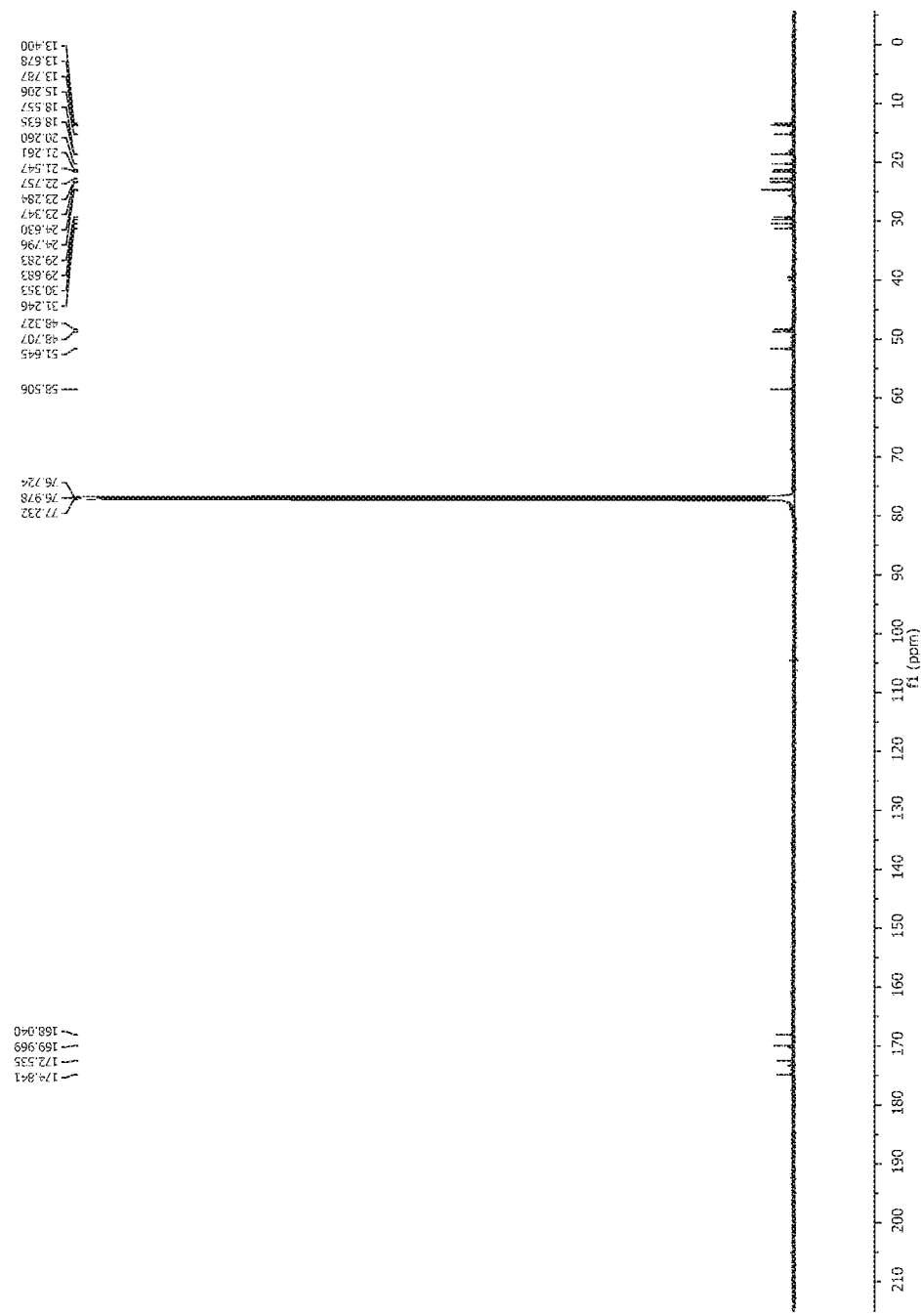
FIG. 10(A) shows $^{13}$C NMR data of 3 (CDCl$_3$).
FIG. 10(B) shows $^{13}$C NMR data of 3 (CDCl$_3$).
FIG. 10(C) shows $^{13}$C NMR data of 3 (CDCl$_3$).
FIG. 10(D) shows $^{13}$C NMR data of 3 (CDCl$_3$).
Figure 10:
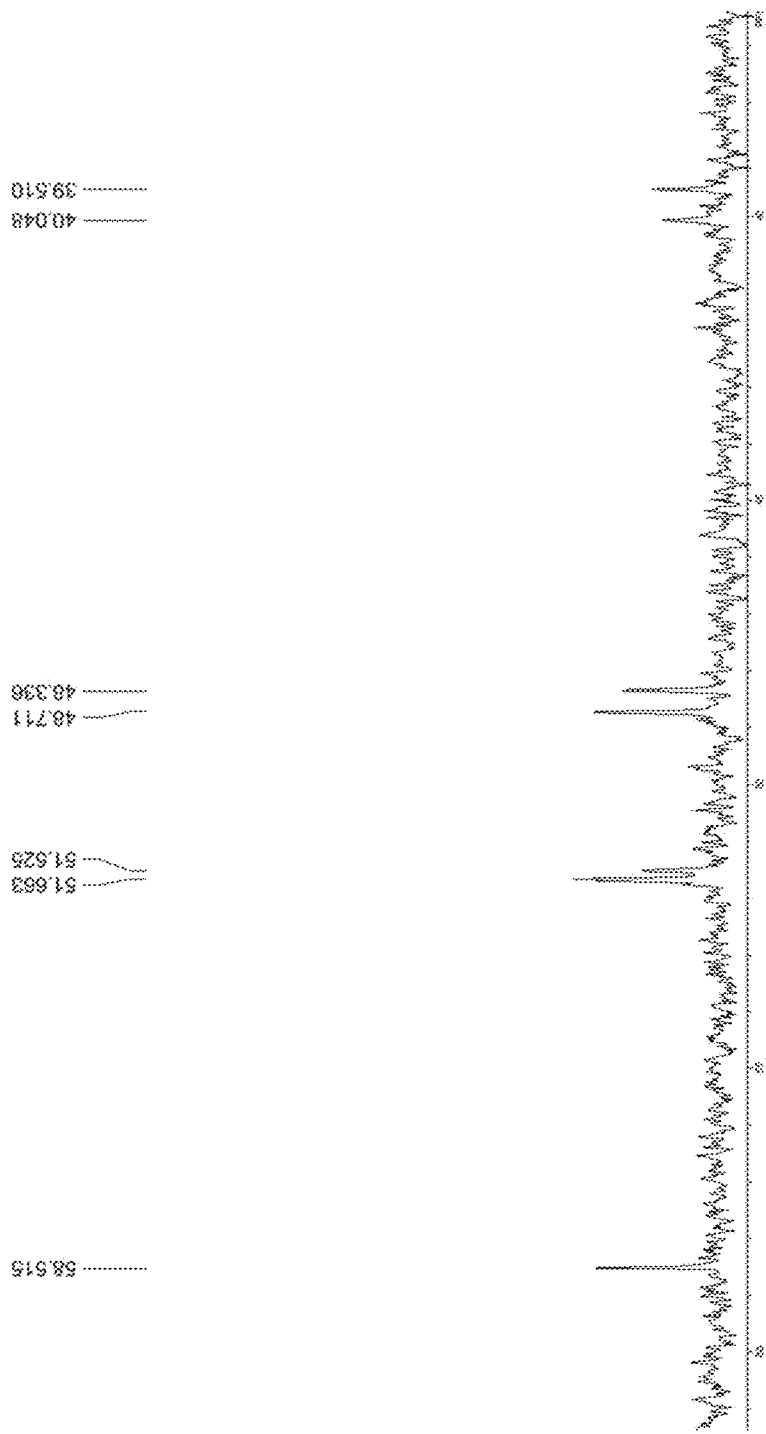
Figure 10D:
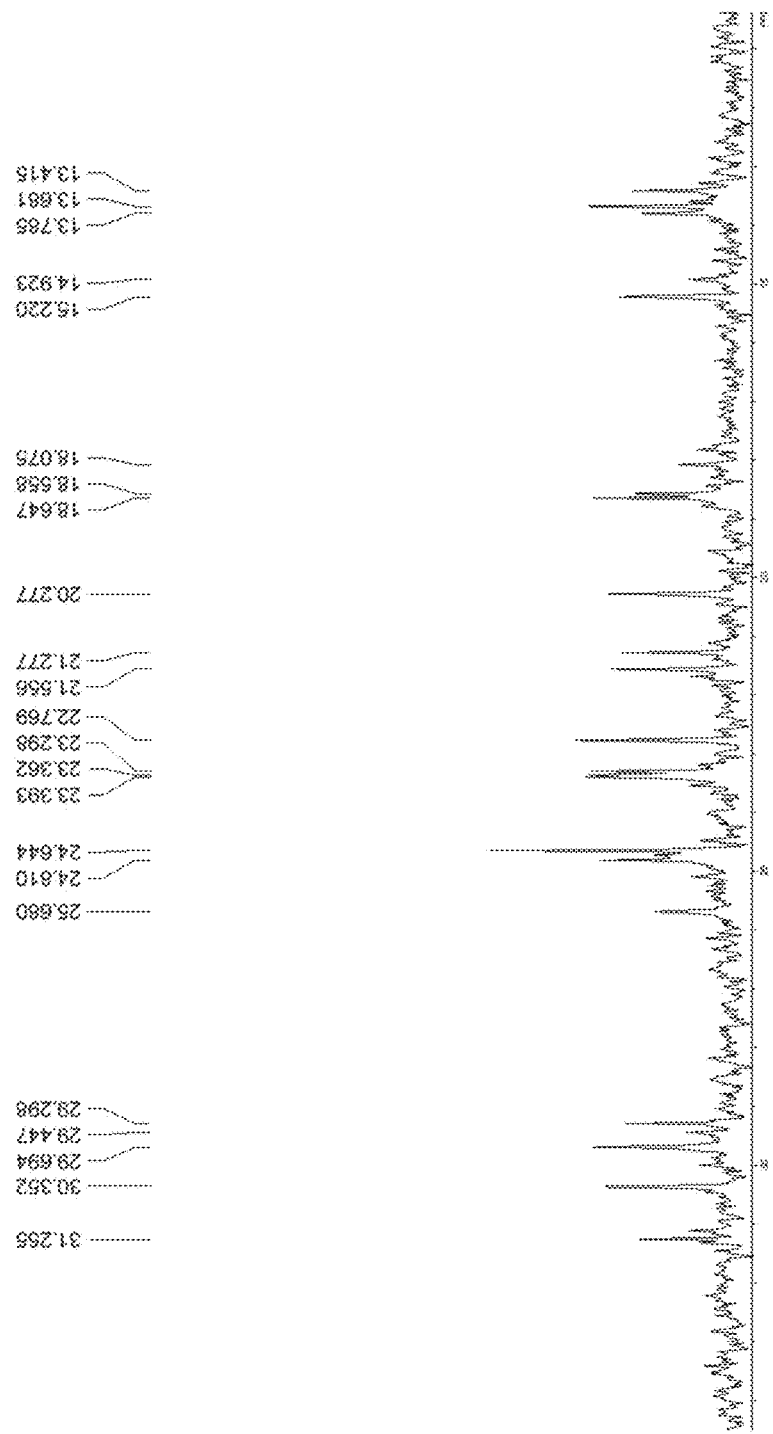
Figure 11:
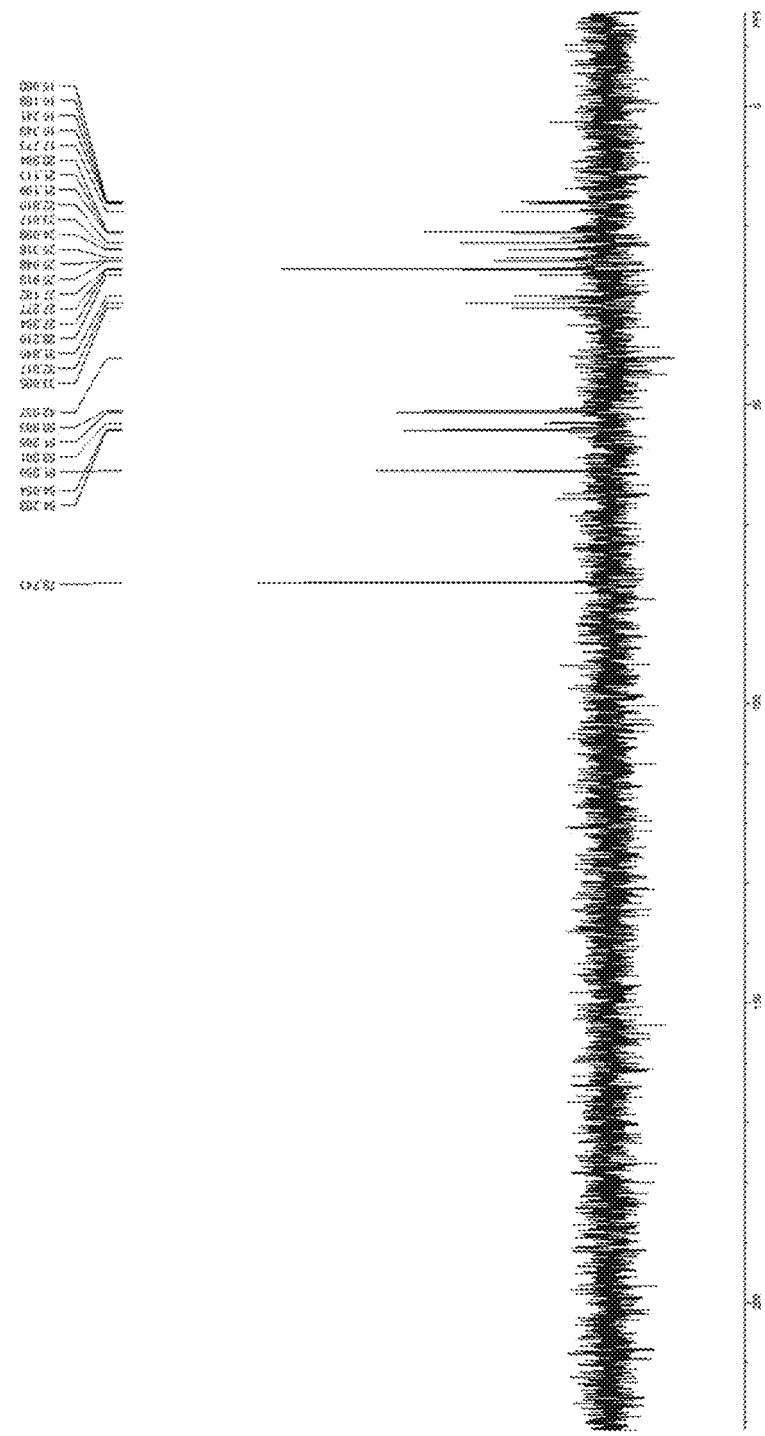
FIG. 11(A) shows DEPT-135 NMR data of 3 (CDCl$_3$).
FIG. 11(B) shows DEPT-135 NMR data of 3 (CDCl$_3$).
Figure 11:
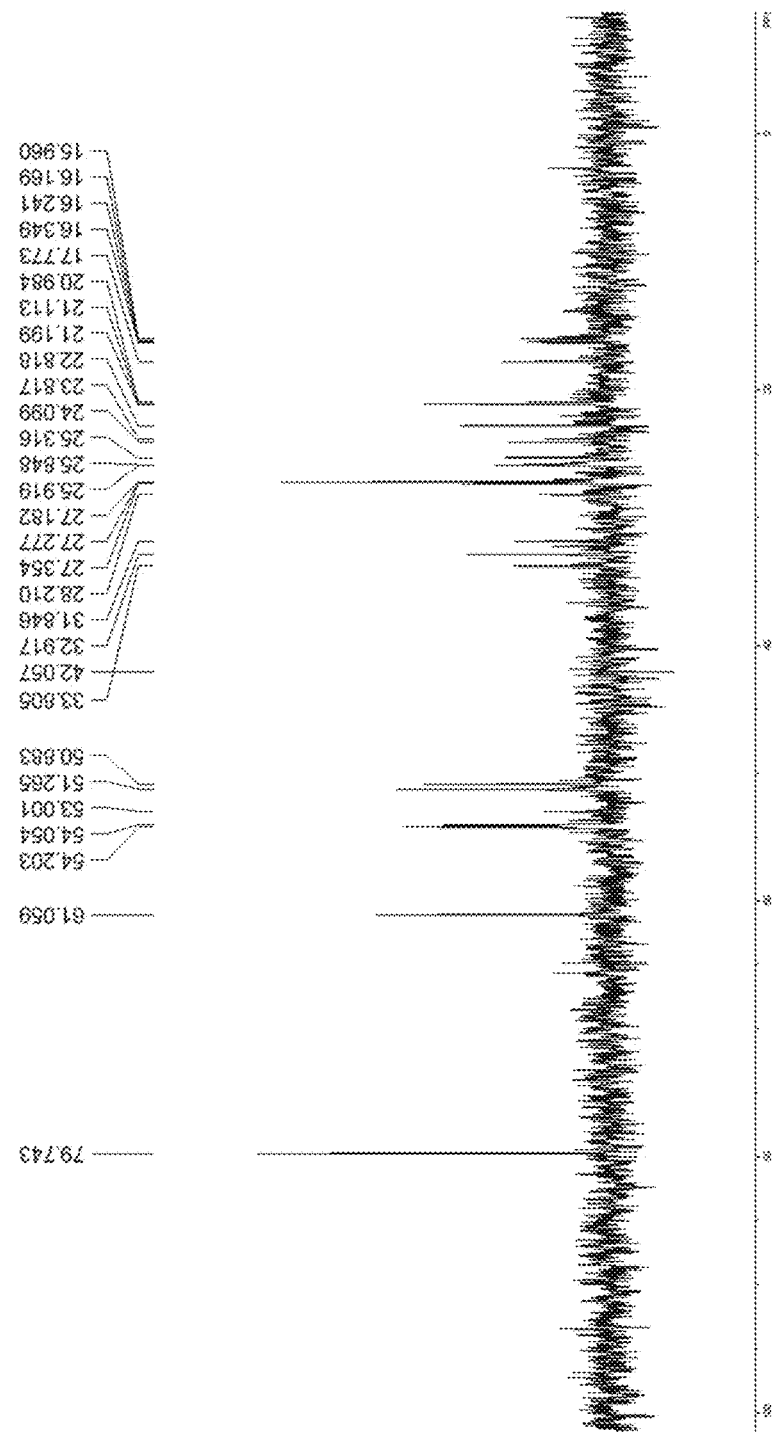
Figure 12:
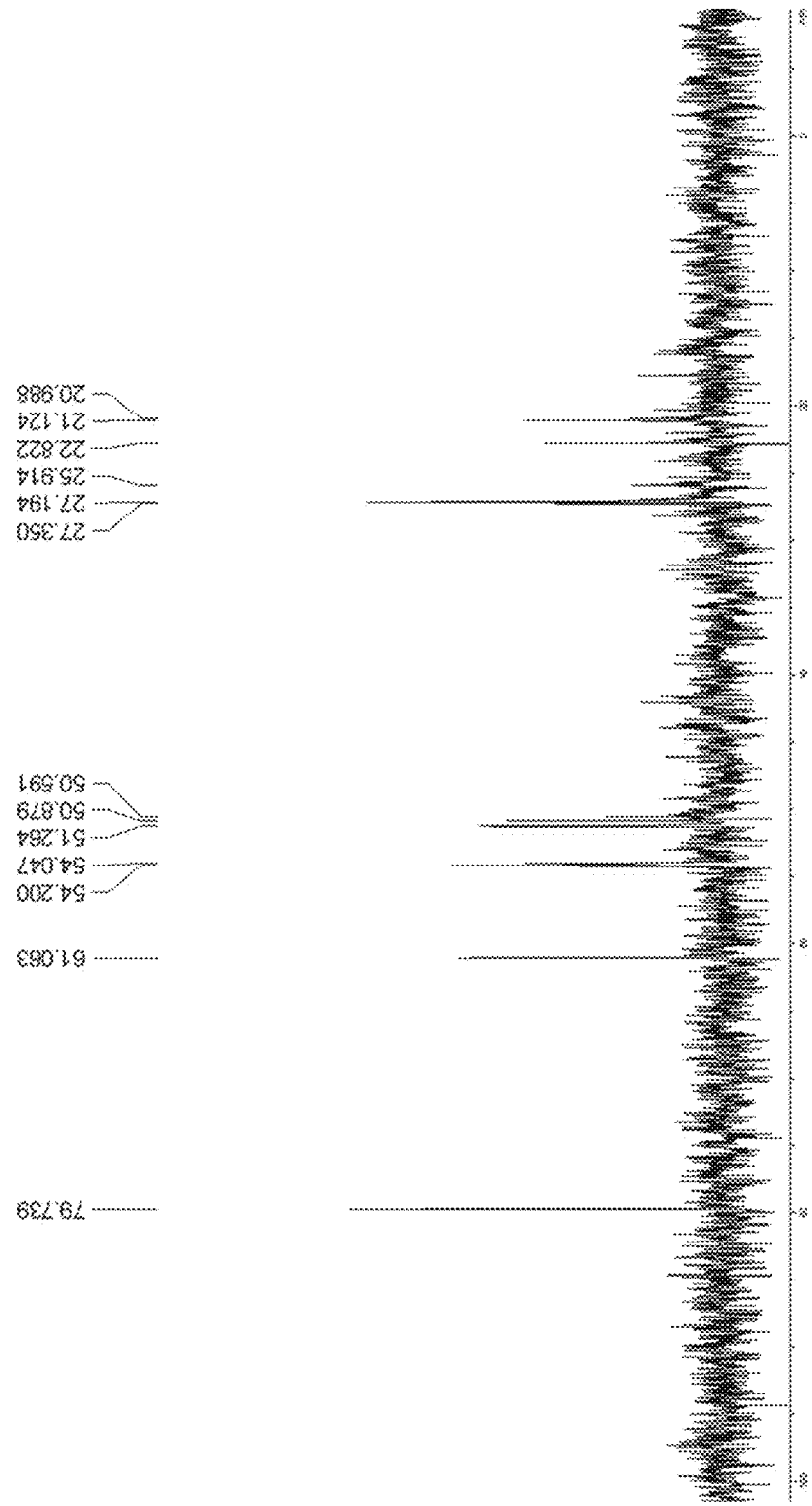
FIG. 12(A) shows DEPT-90 NMR data of 3 (CDCl$_3$).
FIG. 12(B) shows DEPT-90 NMR data of 3 (CDCl$_3$).
Figure 12:
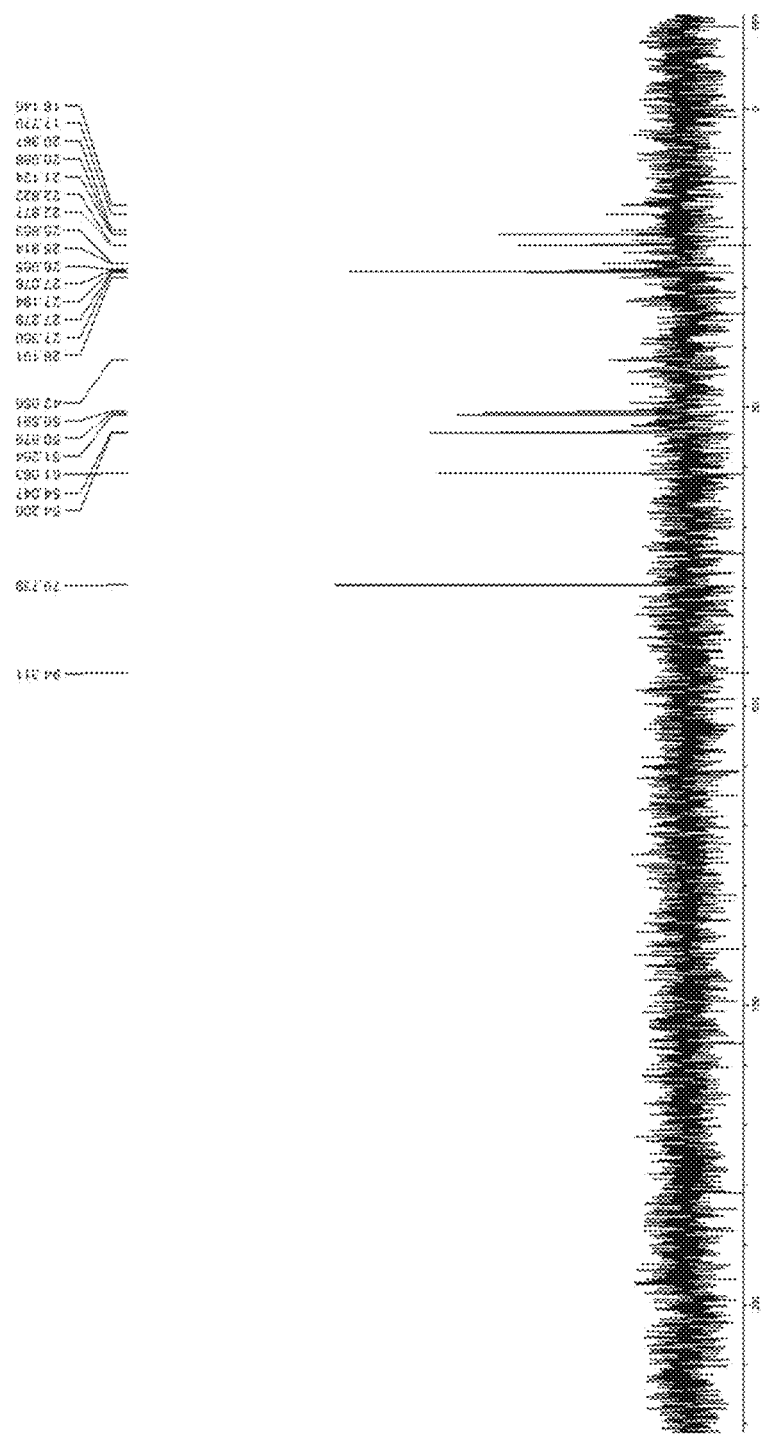

The present invention is not to be limited in scope by any of the specific embodiments described herein. The following embodiments are presented for exemplification only.

In his continuing drug discovery program, the inventor has discovered potent anticancer and anti-obesity compounds from a plant. The promising compounds belong to cyclopeptides containing a novel amino acid residue, and they were isolated from the stem barks of *Maytenus variabilis* (Loes.) C. Y. Cheng (Celastraceae). The novel cyclopeptide compounds (1, 2 and 3) demonstrated tumor cell killing activity against a panel of human cancer cell lines with IC$_{50}$ values in the range of 0.05-52 nM. Compound 1 also demonstrated to be effective on reducing body weight of mice.

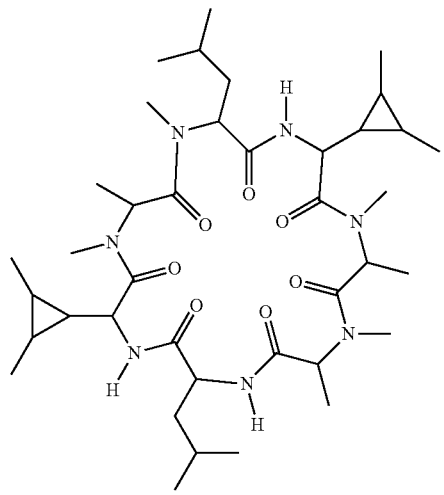

1

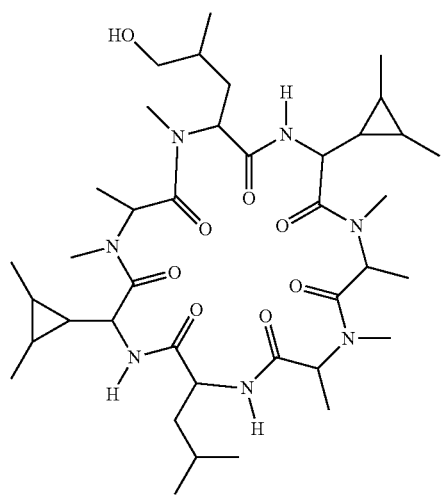

2

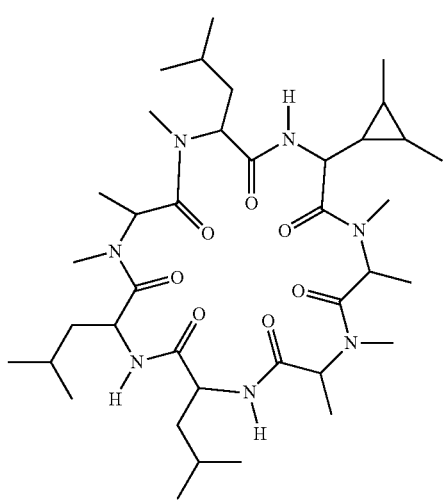

3

The inventor discovered several potent anticancer and anti-obesity compounds (1, 2 and 3) belonging to cycloheptapeptide molecules, which the inventor designated as "mavacyocines". The inventor has further synthesized several mavacyocine compounds (MV-A, MV-C and MV-D), and one orientation of compound 2 is determined as MV-B. These compounds demonstrated tumor cell killing activity against a panel of human cancer cell lines with $IC_{50}$ values in the range of 0.05-52 nM. Compound MV-A also demonstrated to be effective on reducing body weight of mice.

MV-A

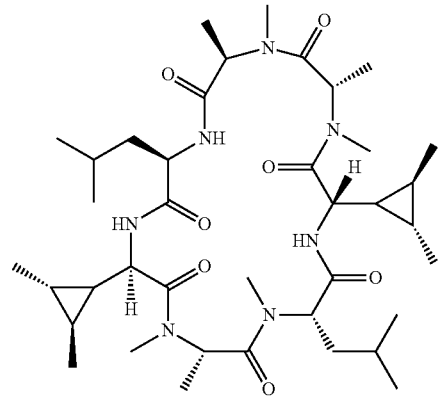

MV-B

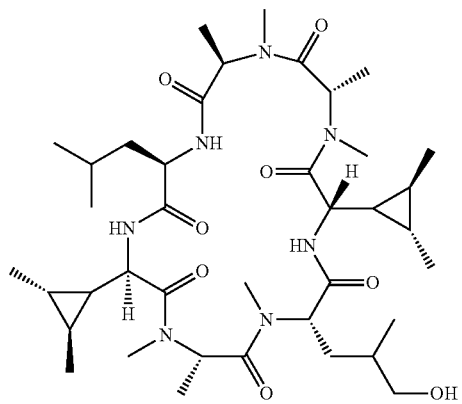

MV-C

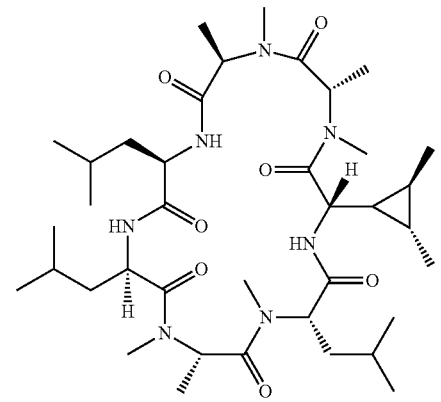

MV-D

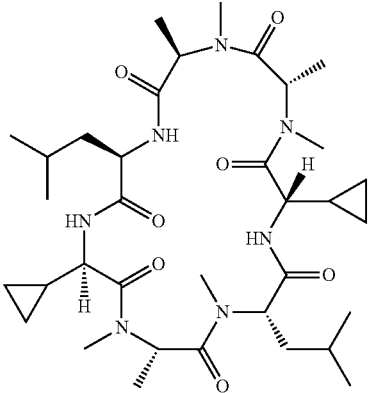

The mavacyocines (MV-A, MV-B, MV-C and MV-D) have demonstrated potent biological activities, and warrant further study and development. Thus, mavacyocine compounds with an improved biological activities and low in toxicity are needed.

Cycloheptapeptide Compound

The term "cycloheptapeptide" as used herein includes reference to a cyclopeptide compound whose amino and carboxyl termini are linked together by a peptide bond to form a circular chain. A cycloheptapeptide comprises the basic structure shown as below:

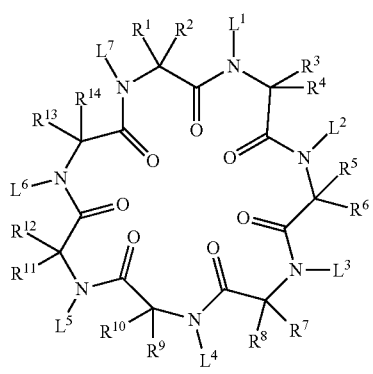

Cycloheptapeptide

The term "cyclohepta-depsipeptide" as used herein includes reference to a cyclodepsipeptide compound, which has at least one lactone linkage in place of one of the amides. A cyclohepta-depsipeptide comprises the basic structure shown as below:

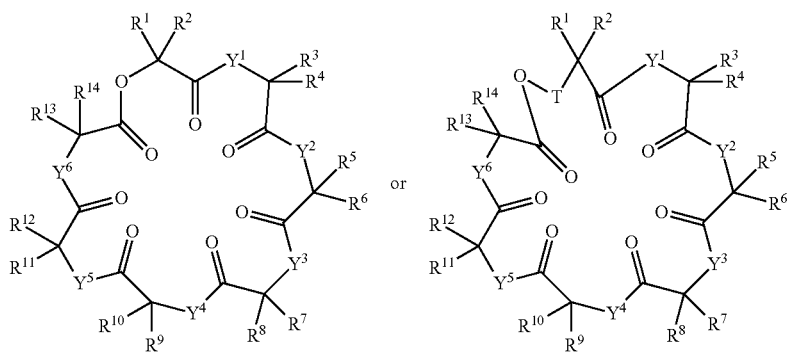

Cyclohepta-depsipeptide $Y^1$, $Y^2$, $Y^3$, $Y^4$, $Y^5$ and $Y^6$ can be oxygen, sulfur or nitrogen substituted with an L group (L can be $L^1$, $L^2$, $L^3$, $L^4$, $L^5$ or $L^6$). T can be a hydrocarbyl or an alkoxy. At least one of the $Y^1$, $Y^2$, $Y^3$, $Y^4$, $Y^5$ and $Y^6$ is nitrogen.

Mavacyocine and Core Structures

The term "mavacyocine" as used herein includes reference to a compound comprising the basic structure shown as below:

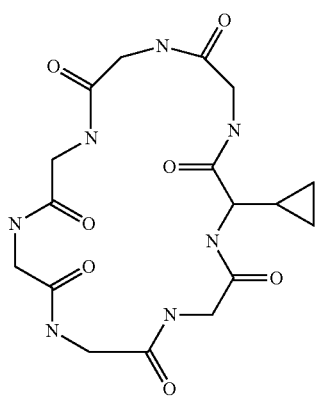

Mavacyocine

The carbon and nitrogen numbering of a mavacyocine molecule as used herein includes reference to a compound comprising numbering system shown as below:

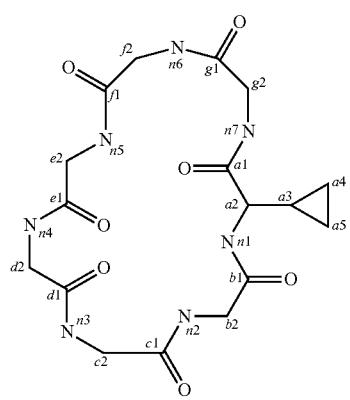 [SMILES: O=C1CNC(=O)CNC(=O)CNC(=O)C(C2CC2)NC(=O)CNC(=O)CNC(=O)CN1]

Further, the carbon and nitrogen numbering of a mavacyocine molecule with substitution groups as used herein includes reference to MV-A numbering system shown as below:

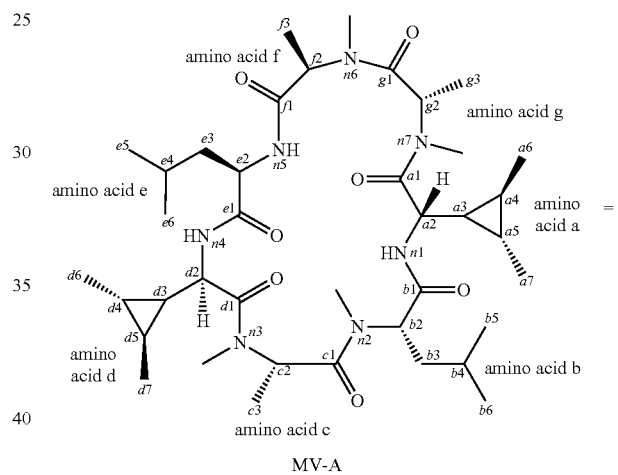

MV-A

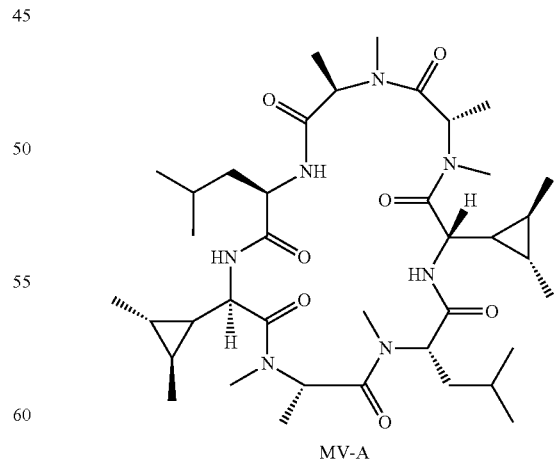

MV-A

Further, the carbon and nitrogen numbering of a mavacyocine molecule with substitution groups as used herein includes reference to MV-B numbering system shown as below:

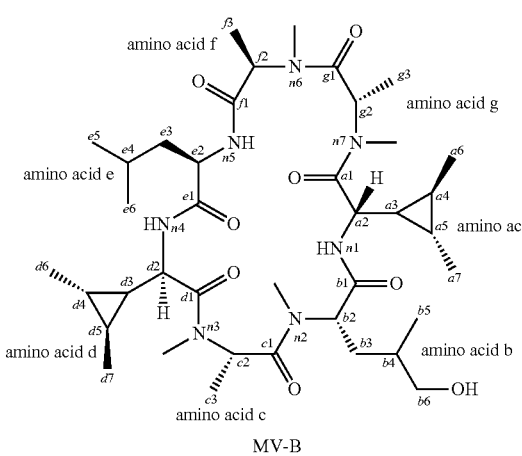

MV-B

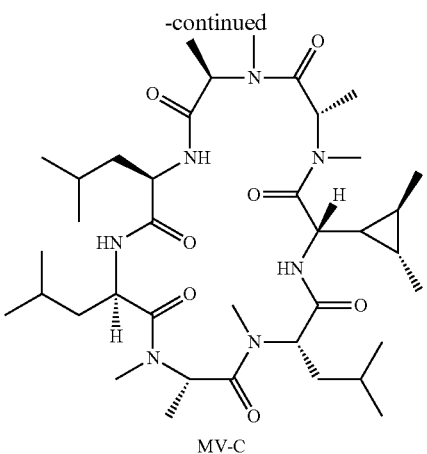

MV-C

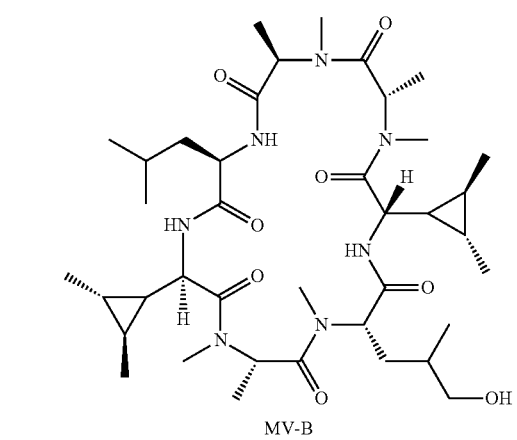

MV-B

Further, the carbon and nitrogen numbering of a mavacyocine molecule with substitution groups as used herein includes reference to MV-C numbering system shown as below:

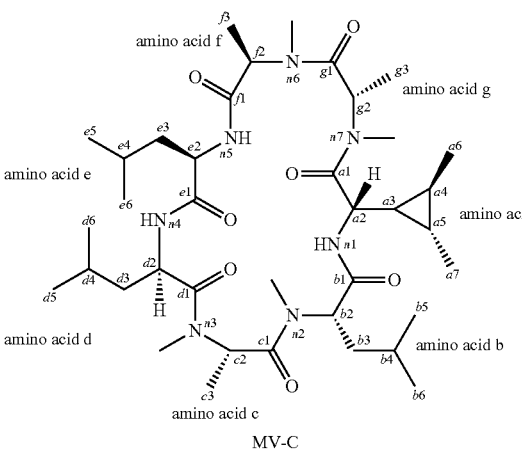

MV-C

Further, the carbon and nitrogen numbering of a mavacyocine molecule with substitution groups as used herein includes reference to MV-D numbering system shown as below:

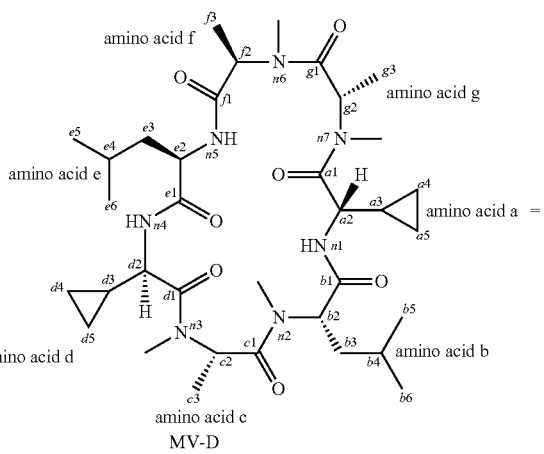

MV-D

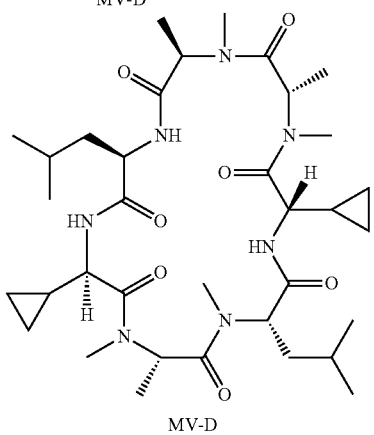

MV-D

Hydrocarbyl

The term "hydrocarbyl" as used herein includes reference to a moiety consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g. cyclopropylmethyl); cycloalkyl (e.g. cyclopropyl, cyclobutyl, cyclopentyl or cyclohexyl); aryl (e.g. phenyl, naphthyl or fluorenyl) and the like.

Alkyl

The terms "alkyl" and "$C_{1-6}$ alkyl" as used herein include reference to a straight or branched chain alkyl moiety having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like. In particular, the alkyl moiety may have 1, 2, 3 or 4 carbon atoms.

Alkenyl

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

Alkynyl

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

Alkoxy

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbomyl, bicyclo[2.2.2]octyl and the like.

Aryl

The term "aryl" as used herein includes reference to an aromatic ring system comprising 6, 7, 8, 9, 10, 11, 12, 13, 14, 15 or 16 ring carbon atoms. The ring or ring system may be substituted with one or more hydrocarbyl groups. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

Cyclic Group

"Cyclic group" means a ring or ring system, which may be unsaturated or partially unsaturated but is usually saturated, typically containing 5 to 13 ring-forming atoms, for example a 3, 4-, 5- or 6-membered ring. The ring or ring system may be substituted with one or more hydrocarbyl groups. Cyclic group includes carbocyclyl and heterocyclyl moieties.

Carbocyclyl

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, 3-, 4-, 5- or 6-membered rings, which may be saturated or unsaturated. The ring or ring system may be substituted with one or more hydrocarbyl groups. A carbocyclic moiety is, for example, selected from cyclopropyl, cyclobutyl, cyclopentyl, cyclohexyl, norbornyl, bicyclo[2.2.2]octyl, phenyl, naphthyl, fluorenyl, azulenyl, indenyl, anthryl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated. The ring or ring system may be substituted with one or more hydrocarbyl groups.

A heterocyclic moiety is, for example, selected from oxiranyl, azirinyl, 1, 2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, pyrrolizidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4V-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazoiyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

Heterocycloalkyl

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like. The ring or ring system may be substituted with one or more hydrocarbyl groups.

Heteroaryl

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. The ring or ring system may be substituted with one or more hydrocarbyl groups. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Amino Acid

The term "amino acid" as used herein includes reference to a compound comprising the basic structure shown as below:

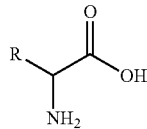

R is selected from $R^1$, —$OR^1$, —$C(O)R^1$ and —$C(O)OR^1$;

$R^1$ is independently selected from hydrogen, halogen, trifluoromethyl, cyano, nitro, hydrocarbyl optionally substituted with 1, 2, 3, 4 or 5 $R^2$, —$(CH_2)_k$-heterocyclyl optionally substituted with 1, 2, 3, 4 or 5 $R^2$, —$OR^3$, —$C(O)R^4$, —$C(O)N(R^3)R^4$, —$C(O)OR^3$, —$OC(O)R^3$, —$S(O)_2R^3$, —$S(O)_2N(R^3)R^4$, —$N(R^3)R^4$, —$N(R^3)N(R^3)R^4$, —$N(R^3)C(O)R^4$ and —$N(R^3)S(O)_2R^4$;

$R^2$ is independently selected from halogen, trifluoromethyl, cyano, nitro, oxo, =$NR^3$, —$OR^3$, —$C(O)R^4$, —$C(O)N(R^3)R^4$, —$C(O)OR^3$, —$OC(O)R^4$, —$S(O)_2R^3$, —$S(O)_2N(R^3)R^4$, —$N(R^3)R^4$, —$N(R^3)N(R^3)R^4$, —$N(R^3)C(O)R^4$ and —$N(R^3)S(O)_2R^4$;

$R^3$ and $R^4$ are each independently hydrogen or selected from hydrocarbyl and —$(CH_2)_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; wherein k is an integer between 1 and 6 (e.g. 1, 2 or 3);

The nitrogen atom of the amino acids may be alkylated to form N-alkylated amino acids. The amino acids can be L-amino acids, or D-enantiomers of all of the above. An amino acid is, for example, selected from twenty genetically encoded L-amino acids (Table 1), common non-encoded amino acids (Table 1), and the like. It also includes α-amino-cyclic-acetic acids (see below the term "α-Amino-cyclic-acetic acid".

TABLE 1

Genetically encoded L-amino acids and common non-encoded amino acids

| Amino Acid | Common Abbreviation |
| --- | --- |
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |
| β-Alanine | bAla |
| 2,3-Diaminopropionic | Dpr |
| α-Aminoisobutyric acid | Aib |
| N-Methylglycine (sarcosine0 | MeGly |
| Ornithine | Orn |
| Citrulline | Cit |
| t-Butylalanine | t-BuA |
| t-Butylglycine | t-BuG |
| N-Methylisoleucine | N-PhGly |
| Phenylglycine | Phg |
| Cyclohexylalanine | Cha |
| Norleucine | Nle |
| 2-Naphthylalanine | 2-Nal |
| 4-Chlorophenylalanine | Phe(4-Cl) |
| 2-Florophenylalanine | Phe(2-F) |
| 3-Florophenylalanine | Phe(3-F) |
| 4-Florophenylalanine | Phe(4-F) |
| Penicillamine | Pen |
| 1,2,3,4-tetrahydroisoquinoline-3-carboxylic acid | Tic |
| β-2-Thienylalanine | Thi |
| Methionine sulfoxide | MSO |
| Homoarginine | hArg |
| N-Acetyl lysine | AcLys |
| 2,4-Diamino butyric acid | $A_2Bu$ |
| p-Aminophenylalanine | Phe(pNH$_2$) |
| N-Methylvaline | MeVal |
| Homocysteine | hCys |
| Homoserine | hSer |
| 2,3-Diaminobutyric acid | DBU |

α-Amino-Cyclic-Acetic Acid

The term "α-amino-cyclic-acetic acid" as used herein includes reference to a compound comprising the basic structure shown as below:

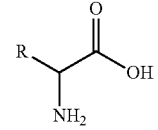

R is selected from cyclic group and —$(CH_2)_k$-cyclic group, either of which is optionally substituted with 1, 2, 3, 4 or 5 substituents independently selected from $R^1$, —$OR^2$, —$C(O)R^3$, —$C(O)N(R^2)R^3$, —$C(O)OR^2$, —$OC(O)R^2$, —$S(O)_2R^2$, —$S(O)_2N(R^2)R^3$, —$N(R^2)R^3$, —$N(R^2)N(R^2)R^3$, —$N(R^2)C(O)R^3$ and —$N(R^2)S(O)_2R^3$;

$R^1$ is independently selected from halogen, trifluoromethyl, cyano, nitro, oxo, =$NR^2$, —$OR^2$, —$C(O)R^3$, —$C(O)N(R^2)R^3$, —$C(O)OR^2$, —$OC(O)R^3$, —$S(O)_2R^2$, —$S(O)_2N(R^2)R^3$, —$N(R^2)R^3$, —$N(R^2)N(R^2)R^3$, —$N(R^2)C(O)R^3$ and —$N(R^2)S(O)_2R^3$;

$R^2$ and $R^3$ are each independently hydrogen or selected from hydrocarbyl and —$(CH_2)_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; wherein k is an integer between 1 and 6 (e.g. 1, 2 or 3).

Amide

The term "amide" as used herein includes reference to a compound comprising the basic structure shown as below:

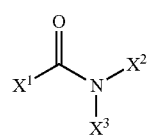

$X^1$ is selected from $R^1$, —$OR^1$, —$C(O)R^1$ and —$C(O)OR^1$;

$X^2$ and $X^3$ are each independently selected from —$C(O)R^1$ and —$C(O)OR^1$;

$R^1$ is independently selected from hydrogen, halogen, trifluoromethyl, cyano, nitro, hydrocarbyl optionally substituted with 1, 2, 3, 4 or 5 $R^2$, —$(CH_2)_k$-heterocyclyl optionally substituted with 1, 2, 3, 4 or 5 $R^2$, —$OR^3$, —$C(O)R^4$, —$C(O)N(R^3)R^4$, —$C(O)OR^3$, —$OC(O)R^3$, —$S(O)_2R^3$, —$S(O)_2N(R^3)R^4$, —$N(R^3)R^4$, —$N(R^3)N(R^3)R^4$, —$N(R^3)C(O)R^4$ and —$N(R^3)S(O)_2R^4$;

$R^2$ is independently selected from halogen, trifluoromethyl, cyano, nitro, oxo, =$NR^3$, —$OR^3$, —$C(O)R^4$, —$C(O)N(R^3)R^4$, —$C(O)OR^3$, —$OC(O)R^4$, —$S(O)_2R^3$, —$S(O)_2N(R^3)R^4$, —$N(R^3)R^4$, —$N(R^3)N(R^3)R^4$, —$N(R^3)C(O)R^4$ and —$N(R^3)S(O)_2R^4$;

$R^3$ and $R^4$ are each independently hydrogen or selected from hydrocarbyl and —$(CH_2)_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; wherein k is an integer between 1 and 6 (e.g. 1, 2 or 3).

Amine

The term "amine" as used herein includes reference to a compound comprising the basic structure shown as below:

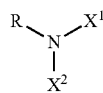

$X^1$ and $X^2$ are each independently selected from $R^1$, —$C(O)R^1$ and —$C(O)OR^1$;

R is independently selected from hydrocarbyl optionally substituted with 1, 2, 3, 4 or 5 $R^2$, —$(CH_2)_k$-heterocyclyl optionally substituted with 1, 2, 3, 4 or 5 $R^2$, —$OR^3$, —$C(O)R^4$, —$C(O)N(R^3)R^4$, —$C(O)OR^3$, —$OC(O)R^3$, —$S(O)_2R^3$, —$S(O)_2N(R^3)R^4$, —$N(R^3)R^4$, —$N(R^3)N(R^3)R^4$, —$N(R^3)C(O)R^4$ and —$N(R^3)S(O)_2R^4$;

$R^1$ is independently selected from hydrogen, halogen, trifluoromethyl, cyano, nitro, hydrocarbyl optionally substituted with 1, 2, 3, 4 or 5 $R^2$, —$(CH_2)_k$-heterocyclyl optionally substituted with 1, 2, 3, 4 or 5 $R^2$, —$OR^3$, —$C(O)R^4$, —$C(O)N(R^3)R^4$, —$C(O)OR^3$, —$OC(O)R^3$, —$S(O)_2R^3$, —$S(O)_2N(R^3)R^4$, —$N(R^3)R^4$, —$N(R^3)N(R^3)R^4$, —$N(R^3)C(O)R^4$ and —$N(R^3)S(O)_2R^4$;

$R^2$ is independently selected from halogen, trifluoromethyl, cyano, nitro, oxo, =$NR^3$, —$OR^3$, —$C(O)R^4$, —$C(O)N(R^3)R^4$, —$C(O)OR^3$, —$OC(O)R^4$, —$S(O)_2R^3$, —$S(O)_2N(R^3)R^4$, —$N(R^3)R^4$, —$N(R^3)N(R^3)R^4$, —$N(R^3)C(O)R^4$ and —$N(R^3)S(O)_2R^4$;

$R^3$ and $R^4$ are each independently hydrogen or selected from hydrocarbyl and —$(CH_2)_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; wherein k is an integer between 1 and 6 (e.g. 1, 2 or 3).

Peptide Bond

The term "peptide bond" as used herein includes reference to a covalent chemical bond formed between two amino acids when the carboxylic acid group of one molecule reacts with the amino group of the other molecule.

Halogen

The term "halogen" as used herein includes reference to F, Cl, Br or I.

Halogen Containing Moiety

The expression "halogen containing moiety" as used herein includes reference to a moiety comprising 1 to 30 plural valence atoms selected from carbon, nitrogen, oxygen and sulphur which moiety includes at least one halogen. The moiety may be hydrocarbyl for example $C_{1-6}$ alkyl or $C_{1-6}$alkoxy, or carbocyclyl for example aryl.

Enantiomer

The term "enantiomer" as used herein means one of two stereoisomers that have mirror images of one another.

Racemate

The term "racemate" as used herein means a mixture of equal amounts of enantiomers of a chiral molecule.

Diastereomer

The term "diastereomer" as used herein means one of a class of stereoisomers that are not enantiomers, but that have different configurations at one or more of the equivalent chiral centers. Example of diasteromers are epimers that differ in configuration of only one chiral center.

Stereoisomer

The term "stereoisomer" as used herein means one of a class of isomeric molecules that have the same molecular formula and sequence of bonded atoms, but different three-dimensional orientations of their atoms in space.

Tautomers

The term "tautomer" means isomeric molecules that readily interconvert by a chemical reaction. The reaction commonly results in the migration of a hydrogen atom, which results in a switch of a single bond and adjacent double bond.

Prodrug

A prodrug is a medication that is administered as an inactive (or less than fully active) chemical derivative that is subsequently converted to an active pharmacological agent in the body, often through normal metabolic processes.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or un-substituted. It will, of course, be understood that substituents are only at positions where they are chemically possible, the person skilled in the art being able to decide (either experimentally or theoretically) without inappropriate effort whether a particular substitution is possible.

Independently

Where two or more moieties are described as being "each independently" selected from a list of atoms or groups, this means that the moieties may be the same or different. The identity of each moiety is therefore independent of the identities of the one or more other moieties.

Embodiments of the invention are described below. Preferred features of each aspect of the invention are as for each of the other aspects mutatis mutandis. Moreover, it will be appreciated that the features specified in each embodiment may be combined with other specified features, to provide further embodiments.

Compounds of the Present Invention

The invention involves the use of cycloheptapeptide and cyclohepta-depsipeptide compounds including derivatives of 1, 2 or 3. Preferably the compounds are cycloheptapeptide and cyclohepta-depsipeptide compounds of which at least one of the peptide bonds is resulted from the coupling of the carbolic acid group of an amino acid and the amino group of an α-amino-cyclic-acetic acid. Further preferred are cycloheptapeptide and cyclohepta-depsipeptide compounds of which the nitrogen atom of at least one of the peptide bonds may be alkylated.

In an exemplary embodiment, the invention provides compounds of the formulae (I) and (II):

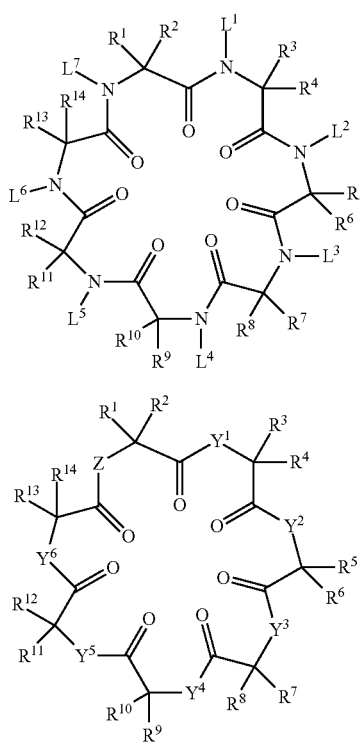

Wherein $R^1$, $R^2$, $R^3$, $R^4$, $R^5$, $R^6$, $R^7$, $R^8$, $R^9$, $R^{10}$, $R^{11}$, $R^{12}$, $R^{13}$ are each independently hydrogen, halogen or a moiety comprising 1 to 30 plural valence atoms selected from carbon, nitrogen, oxygen and sulphur;

At least one of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is a cyclic group;

$R^1$ and $R^2$, $R^3$ and $R^4$, $R^5$ and $R^6$, $R^7$ and $R^8$, $R^9$ and $R^{10}$, $R^{11}$ and $R^{12}$ or $R^{13}$ and $R^{14}$ may be taken together with the carbon atoms to which they are attached to form one or more carboxyl groups (C=O); or while one of $R^1$ and $R^2$, $R^3$ and $R^4$, $R^5$ and $R^6$, $R^7$ and $R^8$, $R^9$ and $R^{10}$, $R^{11}$ and $R^{12}$ or $R^{13}$ and $R^{14}$ is hydrogen, halogen, hydrocarbyl or alkoxy, the other one of $R^1$ and $R^2$, $R^3$ and $R^4$, $R^5$ and $R^6$, $R^7$ and $R^8$, $R^9$ and $R^{10}$, $R^{11}$ and $R^{12}$ or $R^{13}$ and $R^{14}$ is independently selected from $R^{15}$, —$OR^{15}$, —$C(O)R^{15}$ and —$C(O)OR^{15}$;

$R^{15}$ is independently selected from hydrogen, halogen, trifluoromethyl, cyano, nitro, hydrocarbyl optionally substituted with 1, 2, 3, 4 or 5 $R^{16}$, —$(CH_2)_k$-heterocyclyl optionally substituted with 1, 2, 3, 4 or 5 $R^{16}$, —$OR^{17}$, —$C(O)R^{18}$, —$C(O)N(R^{17})R^{18}$, —$C(O)OR^{17}$, —$OC(O)R^{17}$, —$S(O)_2R^{17}$, —$S(O)_2N(R^{17})R^{18}$, —$N(R^{17})R^{18}$, —$N(R^{17})N(R^{17})R^{18}$, —$N(R^{17})C(O)R^{18}$ and —$N(R^{17})S(O)_2R^{18}$;

$R^{16}$ is independently selected from halogen, trifluoromethyl, cyano, nitro, oxo, =$NR^{17}$, —$OR^{17}$, —$C(O)R^{18}$, —$C(O)N(R^{17})R^{18}$, —$C(O)OR^{17}$, —$OC(O)R^{18}$, —$S(O)_2R^{17}$, —$S(O)_2N(R^{17})R^{18}$, —$N(R^{17})R^{18}$, —$N(R^{17})N(R^{17})R^{18}$, —$N(R^{17})C(O)R^{18}$ and —$N(R^{17})S(O)_2R^{18}$;

$R^{17}$ and $R^{18}$ are each independently hydrogen or selected from hydrocarbyl and —$(CH_2)_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy; wherein k is an integer between 1 and 6 (e.g. 1, 2 or 3);

$L^1$, $L^2$, $L^3$, $L^4$, $L^5$, $L^6$ and $L^7$ are each independently selected from $R^{15}$, —$C(O)R^{15}$ and —$C(O)OR^{15}$;

$R^1$, $R^2$, $R^3$, $R^4$, $R^5$, $R^6$, $R^7$, $R^8$, $R^9$, $R^{10}$, $R^{11}$, $R^{12}$, $R^{13}$ $R^{14}$, $L^1$, $L^2$, $L^3$, $L^4$, $L^5$, $L^6$ and $L^7$ may be taken together with the carbon atoms and the nitrogen atoms to which they are attached to form one or more cyclic groups which is optionally substituted with halogen or a moiety comprising 1 to 30 plural valence atoms selected from carbon, nitrogen, oxygen and sulphur;

Z is selected from oxygen, nitrogen, hydrocarbyl, or alkoxy;

$Y^1$, $Y^2$, $Y^3$, $Y^4$, $Y^5$ and $Y^6$ are each independently selected from oxygen, sulfur, nitrogen with substitution of an $L^1$, $L^2$, $L^3$, $L^4$, $L^5$ or $L^6$ group, $C_{1-6}$ alkyl or $C_{1-6}$ alkoxy. At least one of $Y^1$, $Y^2$, $Y^3$, $Y^4$, $Y^5$ and $Y^6$ is nitrogen with substitution of an $L^1$, $L^2$, $L^3$, $L^4$, $L^5$ or $L^6$ group when Z is oxygen, hydrocarbyl or alkoxy;

or an enantiomer thereof;

or a pharmaceutically acceptable salt or prodrug thereof.

Examples of the compounds of the invention include those shown below. It will of course be appreciated that, where appropriate, each compound may be in the form of the free compound, an enantiomer, an acid or base addition salt, or a prodrug.

EXAMPLES

The dry stem barks (3.0 kg) from the decaying wood of *Maytenus variabilis* (Loes.) C. Y. Cheng (Celastraceae) were collected through purchase from Guizhou, China. A primary screening showed that the methanol extract made from a small of amount of the plant materials (5 g) exhibited complete inhibition activity against HCT116 cancer cells at a concentration of 0.625 µg/mL. All the collected barks are thus submitted to phytochemical study in order to identify anticancer compounds. As a result, three novel cyclic peptides (1, 2 and 3) are isolated from the methanol extract of this plant.

The cyclopeptides 1 and 2 demonstrate potent activity against a panel of cancer cell lines (Tables 2 and 3). Compound 1 displays more potent cell killing activity than those of paclitaxel and vinblastine. It also shows comparative activity to the anticancer compound maytansine. Furthermore, compound 1 is able to inhibit cancer cells by more than 90% at much lower concentration than those of maytansine, paclitaxel and vinblastine (Table 3).

Different from the common cyclopeptides, which are normally formed from the common amino acids listed in Table 1, the structures of compounds 1, 2 and 3 are containing peptide bond(s) made from a novel amino acid. The novel amino acid is identified as α-amino-2,3-dimethyl-cyclopropaneacetic acid (DMCPA), which has not been reported in the literature. The inventor believes that the novel amino acid forms key substructural component(s) responsible for the cancer cell killing activity of the isolated cyclopeptides.

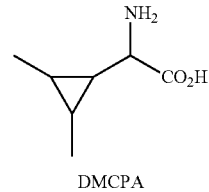

DMCPA

When one of the DMCPA residues is replaced by a leucine residue, the cancer cell killing activity significantly reduces. In comparison with 1, compound 3 contains only one DMCPA residue, which results in reduction of at least 100 times in activity for 3.

In the literature, the inventor finds a cycloheptapeptide (ternatin), which is structurally similar to 1, 2 and 3, but the compound does not have a DMCPA residue. Ternatin was reported to possess cytotoxic activity against murine P388 leukemia cells with $IC_{50}$ value of 1.63 µM (Feng Y J, Blunt J W, Cole A L J, Cannon J F, Robinson W T, Munro M H G. Journal of Organic Chemistry 2003; 68: 2002-2005.). To compare with the literature data of ternatin, the inventor has evaluated the effects of compounds 1 and 2 on murine P388 leukemia cells, which show that 1 and 2 are able to inhibit cell growth of murine P388 leukemia cells by 100% at a concentration of 10 ng/mL. The result demonstrates that the cyclopeptides having the DMCPA residue (i.e. 1 and 2) possess much more potent biologically activity than ternatin.

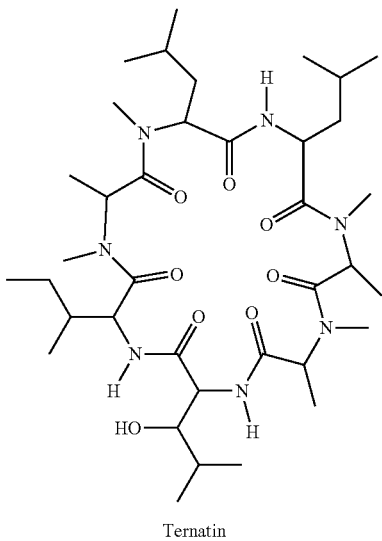 [SMILES: CCC(C)C1NC(=O)C(C(O)C(C)C)NC(=O)C(C)N(C)C(=O)C(C)N(C)C(=O)C(CC(C)C)NC(=O)C(CC(C)C)N(C)C(=O)C(C)N(C)C1=O]

Ternatin

Further, the activity is affected by the presence of an adjacent functional group that may have interference with the DMCPA residue. For example, although compound 2 has comparative activity to paclitaxel, it shows much lower activity than 1. The only structural difference between the two compounds is that the leucine residue near the DMCPA residue in 1 is substituted by a hydroxy group in 2. This hydroxy substitute might have greatly disrupted the binding interaction between the DMCPA residue and the DMCPA targeted protein.

Ternatin has been reported to be a potent inhibitor of fat accumulation against 3T3-L1 murine adipocytes (Shimokawa K, Mashima I, Asai A, Yamada K, Kita M, Uemura D. Tetrahedron Letters 2006; 47: 4445-4448.). Since the chemical structures of compounds 1, 2 and 3 are structurally similar to that of ternatin, the inventor believes that the three compounds may also have inhibition activity against 3T3-L1 murine adipocytes. The inventor further believes that 1, 2 and 3 may exhibit even much higher fat-accumulation inhibitory effects than that of ternatin because these compounds contain DMCPA residue(s). In an animal study, the inventor demonstrate that the body weights of mice are significantly decreased after drug treatment of 1. The average weight of mice (10 mice) drops 1.5 g and 2.2 g after the first treatment (i.p. injection) with 1 at a dose of 1 mg/kg and 2 mg/kg, respectively, but the weight of the mice is kept relatively stable after the first treatment. After six treatments (twice a week), the average weight of mice drops 1.7 g and 4.7 g at 1 mg/kg and 2 mg/kg, respectively. No mice die during the six treatments, and the average weight of mice gains back after the treatment stopped, which showed that the effects of compound 1 on the mice are reversible. No sign of toxicity is observed from dissection of the mice.

TABLE 2

Cytotoxic activity ($IC_{50}$ values) of compounds 1-3

| | Bioactivity: $IC_{50}$ (nM) | | | | |
|---|---|---|---|---|---|
| Compound | KB | HCT116 | LNCaP | A549 | MCF7 |
| 1 | 0.05 | 0.25 | 0.42 | 0.24 | 0.26 |
| 2 | 0.79 | 2.62 | Not tested | 6.35 | 5.83 |
| 3 | 12.5 | 43.5 | Not tested | 51.8 | 26.6 |
| Maytansine | 0.16 | Not tested | 0.56 | 3.18 | 0.69 |
| Paclitaxel | 3.38 | 5.78 | 15.9 | 4.81 | 3.24 |

TABLE 3

Cytotoxic activity ($IC_{90}$ values) of compounds 1-3

| | Bioactivity: $IC_{90}$ (nM) | | | |
|---|---|---|---|---|
| Compound | KB | HCT116 | A549 | MCF7 |
| 1 | 1.65 | 0.69 | 1.02 | 1.47 |
| 2 | 11.4 | Not tested | 6.84 | 9.21 |
| 3 | Not tested | Not tested | Not tested | Not tested |
| Maytansine | ~5 | Not tested | >40 | >20 |
| Paclitaxel | >20 | >20 | >20 | >30 |
| Vinblastine | 10.1 | Not tested | >40 | >50 |

The inventor has discovered potent anticancer compounds from a plant, and further showed that one of the compounds is able to inhibit fat-accumulation in mice.

Plant Materials.

The dry stem barks (3.0 kg) from the decaying wood of *Maytenus variabilis* (Loes.) C. Y. Cheng (Celastraceae) were collected from Guizhou Province, China.

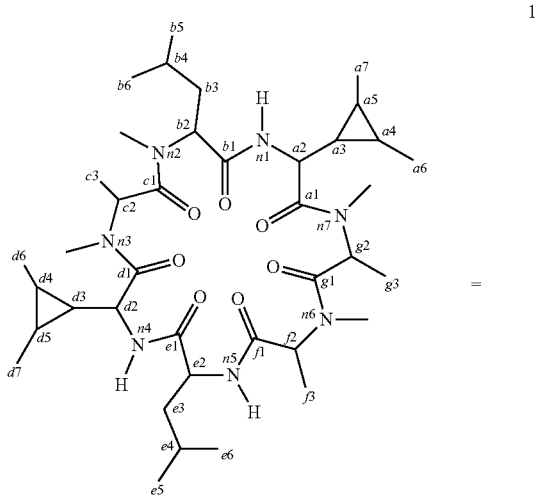

1

1

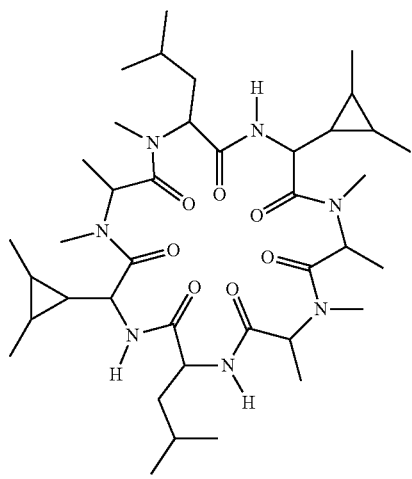

2

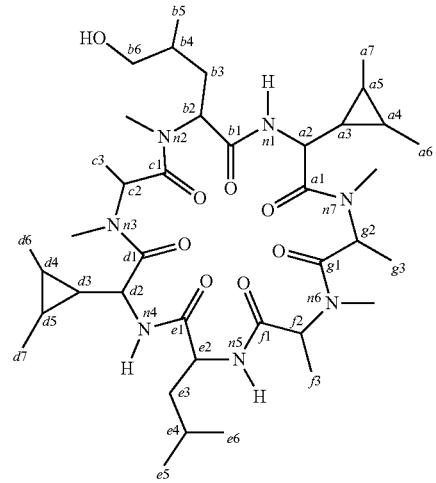

3

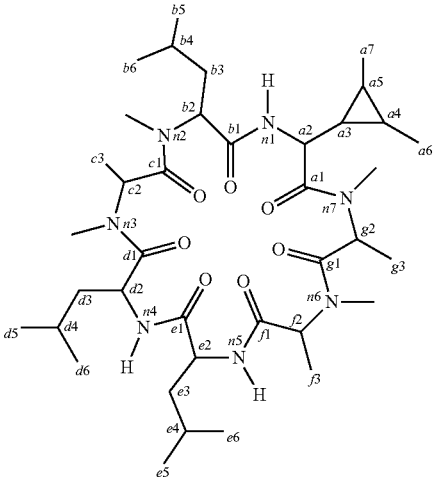

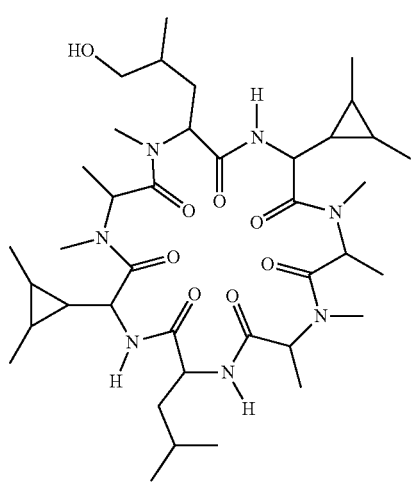

Extraction and Isolation.

The dried and milled stem barks (3 kg) of *Maytenus variabilis* are extracted with methanol (MeOH) to afford an extract, which is subsequently defatted with n-hexane and partitioned with $CHCl_3$. Separation of the $CHCl_3$-soluble fraction by column chromatography on Si gel and RP-18 Si gel columns leads to the isolation of 1 (8.7 mg), 2 (5.2 mg) and 3 (2.1 mg).

Figure 13:
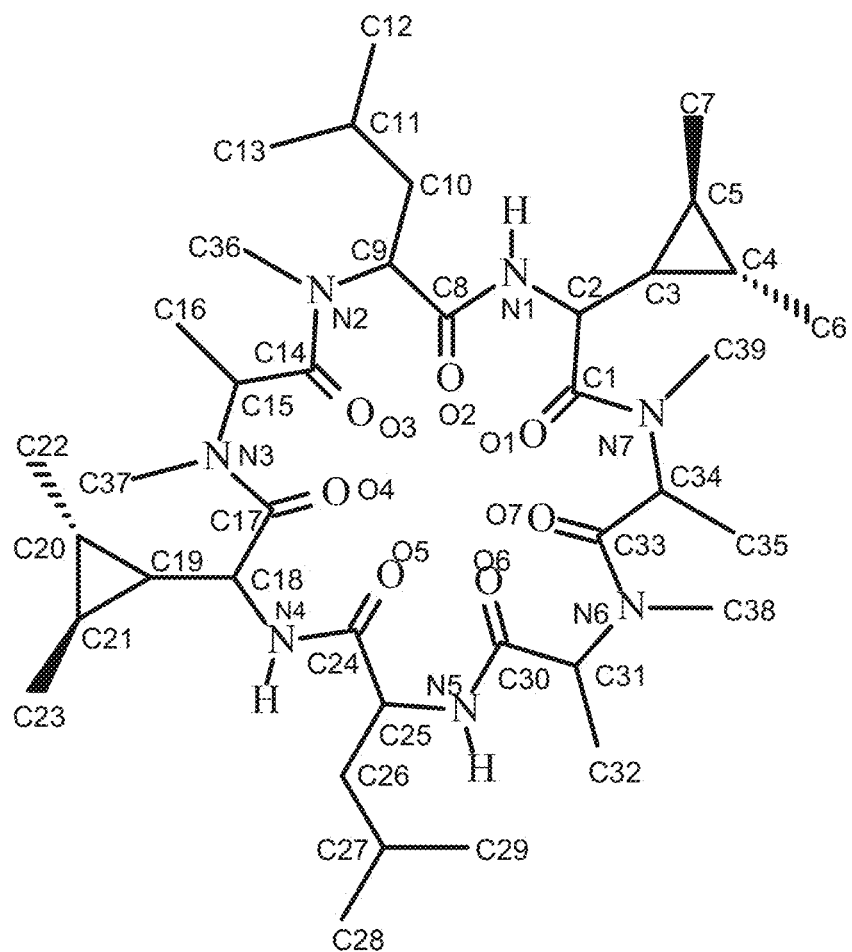
FIG. 13 shows label of the atoms of the structure of compound 1 for X-ray crystallography.
Figure 14:
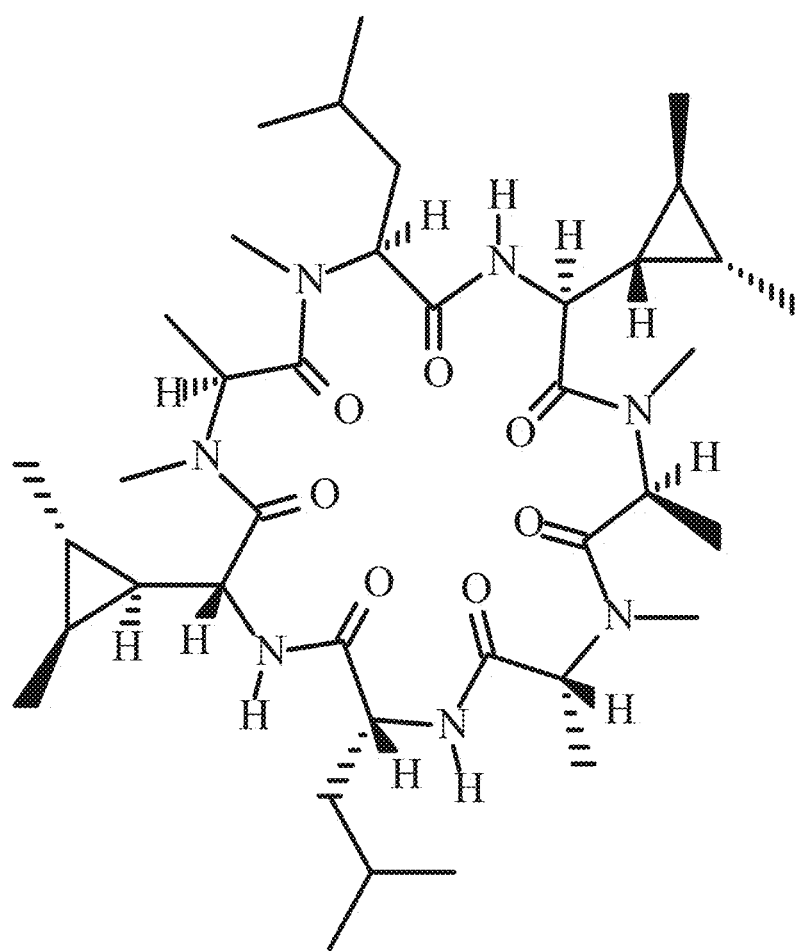
FIG. 14 shows the stereochemistry of the structure of compound 1 determined by X-ray crystallography.
Figure 15:
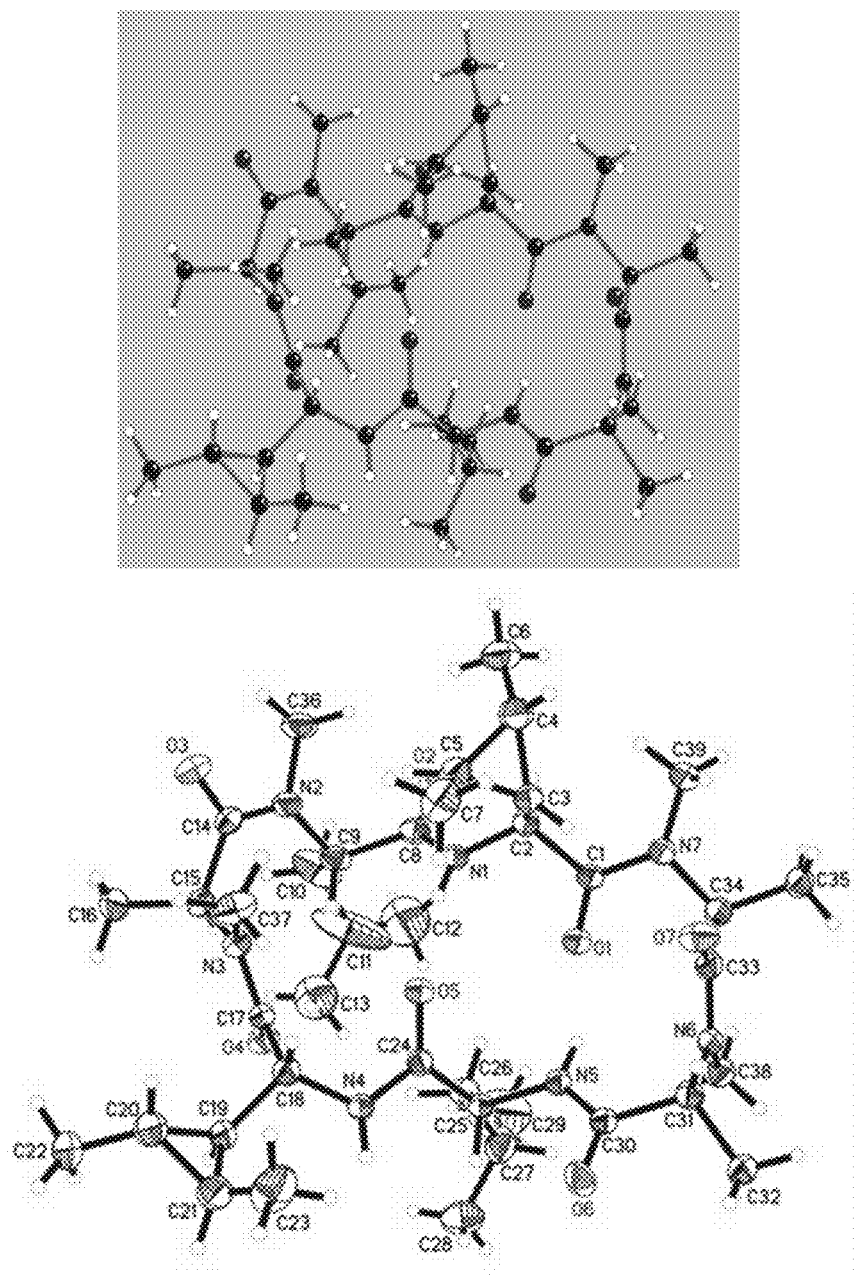
FIG. 15 shows the single-crystal X-ray structures of compound 1.

Compound 1, $[\alpha]_D^{20}$ −2.9° (c 0.17, MeOH); is obtained as a white powder with a molecular formula of $C_{39}H_{67}N_7O_7$ by positive HRESIMS ($[M+H]^+$ m/z 746.5123, calcd. 746.5175) and NMR studies (Tables 4 and 5, and FIGS. 1(A)-1(H) and FIGS. 2(A)-2(D)). In combination of analysis of 2D NMR data including $^1H$-$^1H$ COSY, HMQC, HMBC, TOCSY and ROESY spectral data, the structure of compound 1 is determined as shown. To confirm the structure and the sterochemistry, 1 was crystallized in acetone/n-hexane (3:1) to afford a crystal of the monoclinic space group $P2_12_12_1$, which was analyzed by X-ray crystallography (FIGS. 13-15). The configuration was determined by the measurement of the Flack parameter, which is calculated during the structural refinement. In our study, the final refinement of the crystal of 1 resulted in a Flack parameter of −0.1 (2), allowing an unambiguous assignment of the stereochemistry of the structure. Crystal data for compound 1 (from acetone/n-hexane 3:1) belong to the monoclinic spacnoclinic space group $P2_12_12_1$. The crystal data:

$C_{39}H_{67}N_7O_7$, M=745, a=32.990 (7), b=23.6494 (6), c=12.0008 (2) Å, α=β=γ=90°, V=9362.98 (4) Å$^3$, Z=4, d=1.07 g/cm$^3$.

Compound 2, $[α]_D^{20}$ −3.5° (c 0.23, MeOH); is obtained as a white powder with a molecular formula of $C_{39}H_{68}N_7O_8$ by positive HRESIMS ([M+H]$^+$ m/z 762.5077, calcd. 762.5124) and NMR studies (Tables 4 and 5, and FIGS. 3(A)-3(B) and FIGS. 4(A)-4(B)). In combination of analysis 2D NMR data including $^1$H-$^1$H COSY, HMQC, HMBC, TOCSY and ROESY spectral data, the structure of compound 2 is determined as shown.

Compound 3, $[α]_D^{20}$ +0.4° (c 0.12, MeOH); is obtained as a white powder with a molecular formula of $C_{38}H_{68}N_7O_7$ by positive HRESIMS ([M+H]$^+$ m/z 734.5127, calcd. 734.5175) and NMR studies (Tables 4 and 5, and FIGS. 5(A)-5(F) and FIGS. 6(A)-6(D)). In combination of analysis 2D NMR data including $^1$H-$^1$H COSY, HMQC, HMBC, TOCSY and ROESY spectral data, the structure of compound 3 is determined as shown.

TABLE 4

$^1$H NMR Spectral Data of Compounds 1-3 (500 MHz; J in Hz; CDCl$_3$)

| Position | 1 | 2 | 3 |
|---|---|---|---|
| | δ (ppm), multiplicity (coupling constant J in Hz) | | |
| Amino acid a | | | |
| H-a2 | 4.67 dd (8.8, 5.9) | 4.60 brdd (8.6, 5.7) | 4.68 brt (7.6) |
| H-a3 | 0.76 m | 0.84 m | 0.75 m |
| H-a4 | 0.25 sextet (5.5) | 0.23 sextet (5.3) | 0.30 br sextet (5.5) |
| H-a5 | 0.76 m | 0.78 sextet (5.5) | 0.75 m |
| CH$_3$-a6 | 0.92 d (5.9) | 0.93 d (5.9) | 0.87-0.98, overlap |
| CH$_3$-a7 | 1.06 d (5.5) | 1.03 d (5.9) | 1.07 d (5.9) |
| NH-n1 | 7.89 d (8.8) | 7.94 d (8.7) | 7.81 d (8.6) |
| Amino acid b | | | |
| H-b2 | 4.19 brdd (9.8, 4.7) | 4.11 brdd (11.1, 3.1) | 4.30 m |
| H-b3a | 2.05 ddd (13.4, 10.2, 5.3) | 2.35 ddd (13.6, 11.6, 6.3) | 2.01 ddd (13.4, 9.2, 5.3) |
| H-b3b | 1.16 ddd (13.5, 8.1, 4.8) | 1.13 ddd (13.7, 7.9, 3.5) | 1.19 ddd (13.5, 8.7, 5.6) |
| H-b4 | 1.43br nonet (6.5) | 1.54 br nonet (6.3) | 1.44 br nontet (6.5) |
| CH$_3$-b5 | 0.95 d (6.6) | 0.98 d (6.9) | 0.87-0.98, overlap |
| H-b6a | | 3.42 dd (11.3, 4.9) | |
| H-b6b | | 3.31 dd (11.2, 5.6) | |
| CH$_3$-b6 | 0.89 d (6.6) | | 0.87-0.98, overlap |
| n2-CH$_3$ | 2.89 s | 2.88 s | 2.86 s |
| Amino acid c | | | |
| H-c2 | 5.44 q (6.5) | 5.45 q (6.5) | 5.40 q (6.6) |
| H$_3$-c3 | 1.27 d (6.6) | 1.26 d (6.6) | 1.26 d (6.3) |
| n3-CH$_3$ | 3.06 s | 3.04 s | 3.07 s |
| Amino acid d | | | |
| H-d2 | 4.14 dd (10.3, 5.6) | 4.08 brdd (10.1, 5.2) | 4.77 m |
| H-d3 | 0.70 m | 0.72 m | |
| H-d3a | | | 1.58 m |
| H-d3b | | | 1.36 m |
| H-d4 | 0.54 sextet (5.5) | 0.56 sextet (5.5) | 1.73 m |
| H-d5 | 0.73 m | 0.72 m | |
| CH$_3$-d5 | | | 0.87-0.98, overlap |
| CH$_3$-d6 | 1.00 d (6.0) | 1.01 d (5.9) | 0.87-0.98, overlap |
| CH$_3$-d7 | 1.05 d (5.8) | 1.05 d (6.0) | |
| NH-n4 | 6.25 brs | 6.20 brd (4.7) | 6.24 brs |
| Amino acid e | | | |
| H-e2 | 4.47 brt (9.0) | 4.61 brt (10.0) | 4.24 m |
| H-e3a | 1.80 brt (10.1) | 1.76 brt (10.2) | 1.84 brt (10.3) |
| H-e3b | 1.64 m | 1.64 m | 1.66 m |
| H-e4 | 1.62 m | 1.62 m | 1.60 m |
| CH$_3$-e5 | 0.98 d (5.7) | 1.00 d (5.7) | 0.87-0.98, overlap |
| CH$_3$-e6 | 0.91 d (5.8) | 0.92 d (5.9) | 0.87-0.98, overlap |
| NH-n5 | 7.51 d (8.8) | 7.52 d (9.1) | 7.42 d (8.6) |
| Amino acid f | | | |
| H-f2 | 5.36 q (7.2) | 5.37 q (7.2) | 5.34 q (7.2) |
| CH$_3$-f3 | 1.32 d (7.2) | 1.33 d (7.2) | 1.32 d (7.2) |
| n6-CH$_3$ | 2.98 s | 2.97 s | 2.99 s |
| Amino acid g | | | |
| H-g2 | 4.89 q (7.3) | 4.92 q (7.4) | 4.86 q (7.3) |
| CH$_3$-g3 | 1.38 d (7.3) | 1.39 d (7.4) | 1.39 d (7.3) |
| n7-CH$_3$ | 3.16 s | 3.16 s | 3.16 s |

TABLE 5

$^{13}$C NMR and DEPT Spectral Data of Compounds 1-3 (125 MHz; CDCl$_3$)

| Position | 1 | 2 | 3 |
|---|---|---|---|
| | δ (ppm), multiplicity | | |
| Amino acid a | | | |
| C-a1 | 173.50 s | 173.45 s | 173.32 s |
| C-a2 | 47.97 d | 48.28 d | 48.33 d |
| C-a3 | 24.79 d | 24.44 d | 25.80 d |
| C-a4 | 18.41 d | 18.52 d | 18.64 d |
| C-a5 | 20.27 d | 20.30 d | 20.27 d |
| C-a6 | 18.56 q | 18.52 q | 18.56 q |
| C-a7 | 13.63 q | 13.60 q | 13.79 q |
| Amino acid b | | | |
| C-b1 | 168.08 s | 168.75 | 168.05 s |
| C-b2 | 58.53 d | 58.72 d | 58.51 d |
| C-b3 | 39.85 t | 33.93 t | 39.50 t |
| C-b4 | 24.74 d | 33.09 d | 24.64 d |
| C-b5 | 21.69 q | 18.04 q | 21.55 q |
| C-b6 | 23.55 q | 66.52 t | 23.39 q |
| CH$_3$-n2 | 29.44 q | 29.55 q | 29.29 q |
| Amino acid c | | | |
| C-c1 | 169.94 s | 169.68 | 170.24 s |
| C-c2 | 49.69 d | 49.99 d | 4 8.71 d |
| C-c3 | 14.90 q | 14.84 q | 15.21 d |
| CH$_3$-n3 | 29.94 q | 29.94 q | 29.69 q |
| Amino acid d | | | |
| C-d1 | 172.24 s | 172.39 s | 172.54 s |
| C-d2 | 50.49 d | 50.62 d | 48.71 d |
| C-d3 | 25.20 d | 25.08 d | 40.05 t |
| C-d4 | 19.54 d | 19.57 d | 24.64 d |
| C-d5 | 17.79 d | 17.73 d | 21.27 q |
| C-d6 | 18.08 q | 18.04 q | 23.35 q |
| C-d7 | 13.19 q | 13.22 q | |
| Amino acid e | | | |
| C-e1 | 172.38 s | 172.51 s | 172.54 s |
| C-e2 | 51.05 d | 50.83 d | 51.65 d |
| C-e3 | 42.56 t | 43.15 t | 41.97 t |
| C-e4 | 24.98 d | 24.79 d | 24.80 d |
| C-e5 | 22.76 q | 21.70 q | 22.76 q |
| C-e6 | 23.37 q | 23.39 q | 23.29 q |
| Amino acid f | | | |
| C-f1 | 169.94 s | 169.96 | 169.97 s |
| C-f2 | 51.78 d | 51.86 d | 51.68 d |
| C-f3 | 13.63 q | 13.71 q | 13.41 q |
| CH$_3$-n6 | 30.39 q | 30.42 q | 30.36 q |
| Amino acid g | | | |
| C-g1 | 174.70 s | 174.69 s | 174.85 s |
| C-g2 | 51.47 d | 51.47 d | 51.50 d |
| C-g3 | 13.63 q | 13.60 q | 13.68 q |
| CH$_3$-n7 | 31.09 q | 31.10 q | 31.25 q |

Further Embodiments of the Present Invention

The present invention provides a synthesis compound with potent anticancer and anti-obesity activity having a formula (IV):

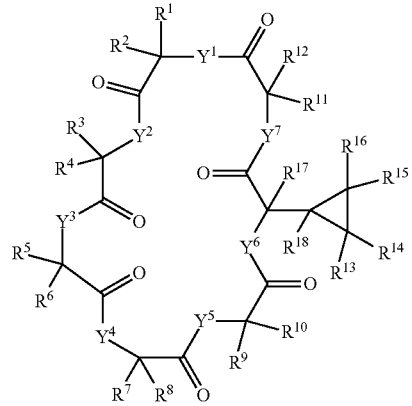

(IV)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are each independently selected from hydrogen, halogen and a moiety comprising 1 to 30 plural valence atoms selected from carbon, nitrogen, oxygen and sulphur;

while one of $R^1$ and $R^2$, $R^3$ and $R^4$, $R^5$ and $R^6$, $R^7$ and $R^8$, $R^9$ and $R^{10}$, $R^{11}$ and $R^{12}$, $R^{13}$ and $R^{14}$ or $R^{15}$ and $R^{16}$ is hydrogen, halogen, hydrocarbyl or alkoxy, the other one of $R^1$ and $R^2$, $R^3$ and $R^4$, $R^5$ and $R^6$, $R^7$ and $R^8$, $R^9$ and $R^{10}$, $R^{11}$ and $R^{12}$, $R^{13}$, $R^{14}$ or $R^{15}$ and $R^{16}$ is independently selected from $R^{19}$, —$OR^{19}$, —$C(O)R^{19}$ and —$C(O)OR^{19}$; or $R^{13}$, $R^{14}$, $R^{15}$ and $R^{16}$ forms one or more carboxyl groups (C=O) with a carbon atom to which they are attached to;

$R^{19}$ is independently selected from hydrogen, halogen, trifluoromethyl, cyano, nitro, hydrocarbyl optionally substituted with 1, 2, 3, 4 or 5 $R^{20}$, heterocyclyl optionally substituted with 1, 2, 3, 4 or 5 $R^{20}$, —$(CH_2)_k$-heterocyclyl optionally substituted with 1, 2, 3, 4 or 5 $R^{20}$, —$OR^{21}$, —$C(O)R^{22}$, —$C(O)N(R^{21})R^{22}$, —$C(O)OR^{21}$, —$OC(O)R^{21}$, —$S(O)_2R^{21}$, —$S(O)_2N(R^{21})R^{22}$, —$N(R^{21})R^{22}$, —$N(R^{21})N(R^{21})R^{22}$, —$N(R^{21})C(O)R^{22}$ and —$N(R^{21})S(O)_2R^{22}$;

$R^{20}$ is independently selected from halogen, trifluoromethyl, cyano, nitro, oxo, =$NR^{20}$, —$C(O)R^{22}$, —$C(O)N(R^{21})R^{22}$, —$C(O)OR^{21}$, —$OC(O)R^{21}$, —$S(O)_2R^{21}$, —$S(O)_2N(R^{21})R^{22}$, —$N(R^{21})R^{22}$, —$N(R^{21})N(R^{21})R^{22}$, —$N(R^{21})C(O)R^{22}$ and —$N(R^{21})S(O)_2R^{22}$ and heterocyclyl optionally substituted with 1, 2, 3, 4 or 5 substituents independently selected from halogen, cyano, amino, hydroxy, $C_{1-6}$ alkyl and $C_{1-6}$ alkoxy;

$R^{21}$ and $R^{22}$ are each independently hydrogen or selected from hydrocarbyl, heterocyclyl and —$(CH_2)_k$-heterocyclyl; each of the hydrocarbyl, heterocyclyl and —$(CH_2)_k$-heterocyclyl is optionally substituted with 1, 2, 3, 4 or 5 substituents independently selected from halogen, cyano, amino, hydroxy, $C_{1-6}$ alkyl and $C_{1-6}$ alkoxy; wherein k is an integer between 1 and 6;

$L^1$, $L^2$, $L^3$, $L^4$, $L^5$, $L^6$ and $L^7$ are each independently selected from $R^{19}$, —$C(O)R^{19}$ and —$C(O)OR^{19}$;

$R^1$, $R^2$, $R^3$, $R^4$, $R^5$, $R^6$, $R^7$, $R^8$, $R^9$, $R^{10}$, $R^{11}$, $R^{12}$, $L^1$, $L^2$, $L^3$, $L^4$, $L^5$, $L^6$ and $L^7$ forms one or more cyclic groups with a carbon atom and a nitrogen atom to which they are attached to, the one or more cyclic groups is optionally substituted with halogen or a moiety comprising 1 to 30 plural valence atoms selected from carbon, nitrogen, oxygen and sulphur;

$Y^1$, $Y^2$, $Y^3$, $Y^4$, $Y^5$, $Y^6$ and $Y^7$ are each independently selected from oxygen, sulfur, nitrogen with substitution of an $L^1$, $L^2$, $L^3$, $L^4$, $L^5$, $L^6$ or $L^7$ group, $C_{1-6}$ alkoxy, or $C_{1-6}$ alkyl optionally substituted with 1, 2, 3, 4 or 5 substituents independently selected from halogen, cyano, amino, hydroxy, $C_{1-6}$ alkyl and $C_{1-6}$ alkoxy; at least one of $Y^1$, $Y^2$, $Y^3$, $Y^4$, $Y^5$, $Y^6$ and $Y^7$ is nitrogen with substitution of an $L^1$, $L^2$, $L^3$, $L^4$, $L^5$, $L^6$ or $L^7$ group;

or an enantiomer thereof;

or a pharmaceutically acceptable salt or pro-drug thereof.

Further to the compound in formula (IV), the present invention further provides for an embodiment having the following formula (V), which is derived from the compound of formula (IV) with $Y^1=N-L^1$, $Y^2=N-L^2$, $Y^3=N-L^3$, $Y^4=N-L^4$, $Y^5=N-L^5$, $Y^6=N-L^6$, $Y^7=N-L^7$:

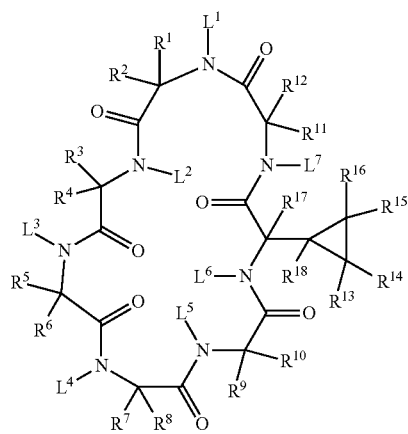

(V)

The present invention further provides four embodiments of compounds MV-A, MV-B, MV-C and MV-D with potent anticancer and anti-obesity activity and synthesis further to the compound of formula (V).

The compounds of the present invention are evaluated for their anticancer and anti-obesity activity, namely compounds MV-A, MV-B, MV-C and MV-D, wherein MV-A is one orientation of compound 1; MV-B is one orientation of compound 2; and MV-C is one orientation of compound 3. The chemical formulae of the compound of the present invention are as follows:

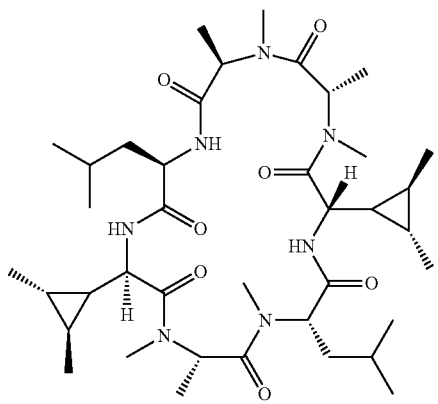

MV-A

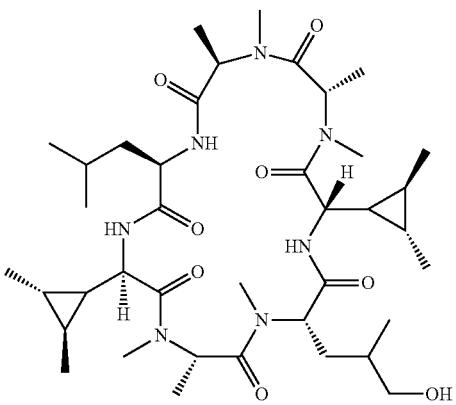

MV-B

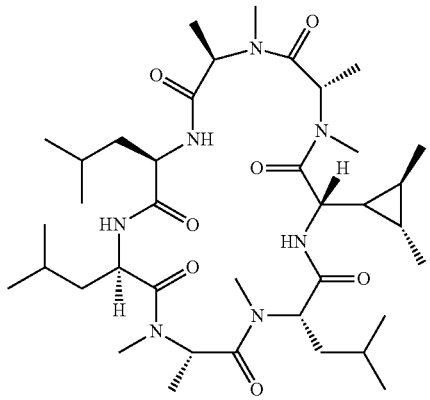

MV-C

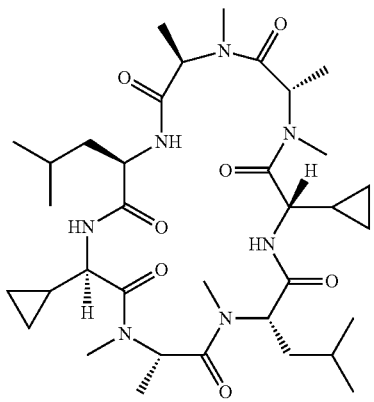

MV-D

Abbreviation of the Chemical Reagents in the Following Chemical Synthesis.

$Boc_2O$: di-tert-butyl dicarbonate; Boc protected amino acid [e.g. Boc-D-(NMe)Ala]; $Br_2$: bromine; $CH_2Cl_2$: dichloromethane; DIPEA: N,N-diisopropyl-ethylamine; DMF: dimethylformamide; $Et_3N$: triethylamine; HATU: 1-[Bis(dimethylamino)methylene]-1H-1,2,3-triazolo[4,5-b]pyridinium 3-oxid hexafluorophosphate (CAS #148893-10-1); HCl: hydrochloric acid; HSi-DES-PS: butyl diethylsilane polystyrene; $I_2$: iodine; KOAc: potassium acetate; LiOH: lithium hydroxide; MeI: methyl iodide; MeOH: methanol; $Me_2S.BH_3$: borane-methyl sulfide; $NaHCO_3$: sodium bicarbonate; NaOMe: sodium methoxide; NMP: N-methyl-2-pyrrolidone; $Pd_2(dba)_3.CHCl_3$: tris(dibenzylideneacetone)dipalladium(O)-chloroform adduct; PyBOP: benzotriazol-1-yl-oxytripyrrolidinophosphonium hexafluorophosphate (CAS #128626-52-5); TFA: trifluoroacetic acid; THF: tetrahydrofuran.

Synthesis of Novel Cyclopeptide Derivatives.

By using the synthetic methods depicted in SCHEMEs 1, MV-D, MV-A and MV-C are synthesized.

Preparation of Amino Acid Resin.

Figure 16:
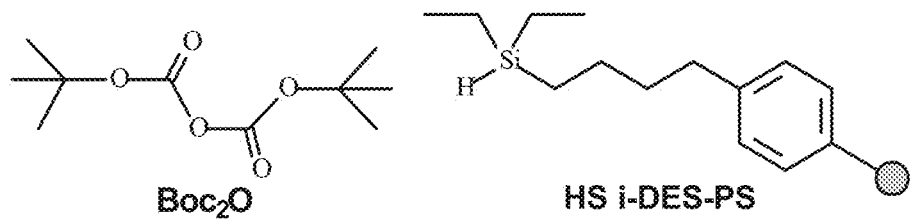
FIG. 16 shows the chemical structures of Boc$_2$O (di-tert-butyl dicarbonate) and HSi-DES-PS (butyl diethylsilane polystyrene).

The amino acid resin is prepared based on the methods depicted in SCHEME 1, and the general experimental procedures are described as following. To a solution of 1 (M.W. 343, 686 mg, 2 mmol) in NMP (N-methylpyrrolidinone) (20 mL) is added HSi-DES-PS (1 g, 1.45 mmol/g) (FIG. 16) and KOAc (300 mg, 0.3 mmol). The reaction mixture is deaerated by bubbling by passing a slow stream of argon through it for 15 min. After the addition of $Pd_2(dba)_3 \cdot CHCl_3$ (M. W. 1035, 110 mg, 0.1 mmol), the reaction flask and reflux condenser are wrapped with aluminum foil, and the mixture is stirred at 110° C. for 24 hours to afford the resin 2. After being cooled to room temperature and washed with $CH_2Cl_2$, DMF, 1N HCl/THF (1:7, 30 min), MeOH, and $CH_2Cl_2$, an aliquot of the resin (2, 200 mg) is treated with a solution of $Br_2$ (15 μL) in $CH_2Cl_2$ (10 mL) for 20 min. The cleavage solution is filtered, and the resin is rinsed with $CH_2Cl_2$ (5 mL). Concentration of the combined filtrates gives 7.5 mg of bromo-1, which indicates that the loading level is 0.1 mmol/g.

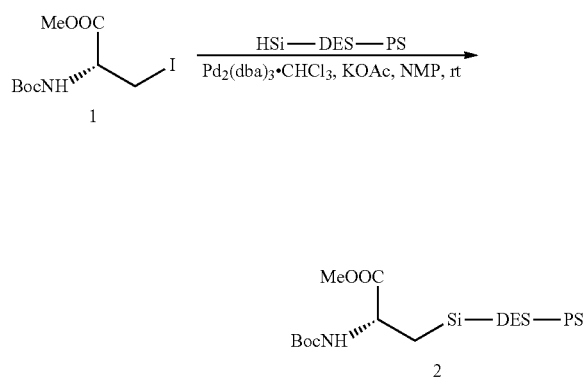

SCHEME 1

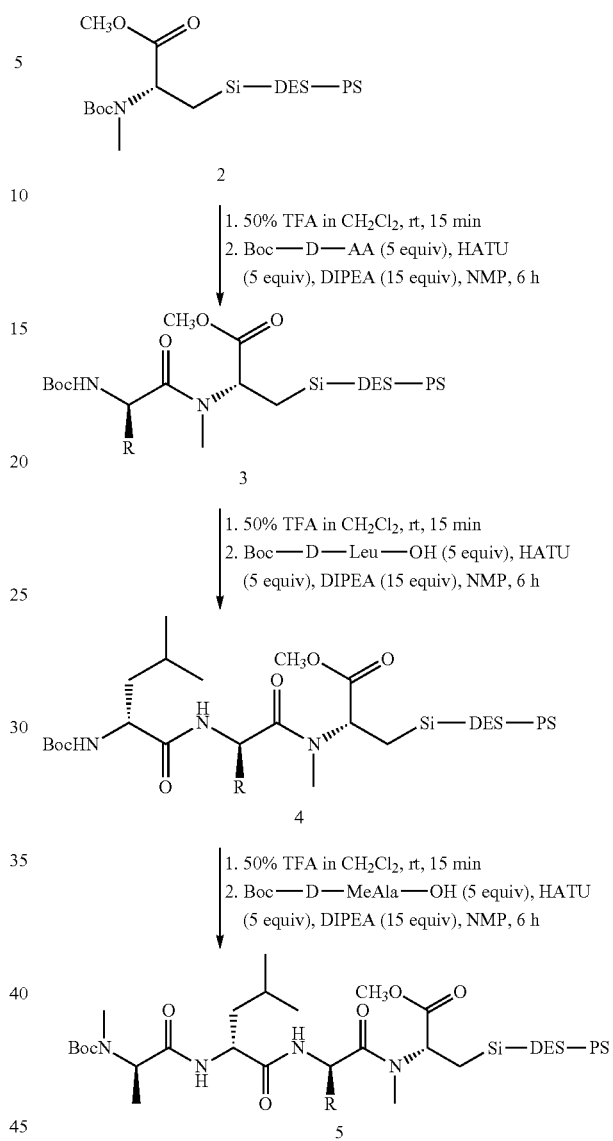

SCHEME 2

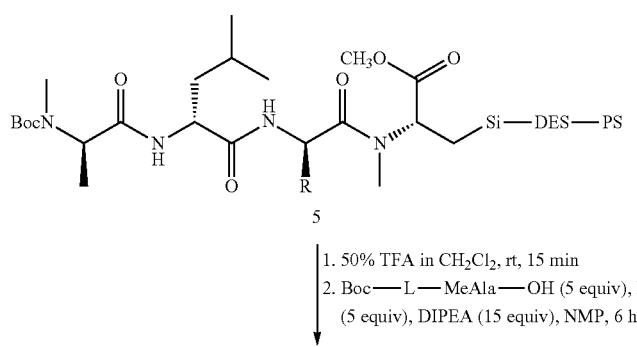

SCHEME 3

-continued
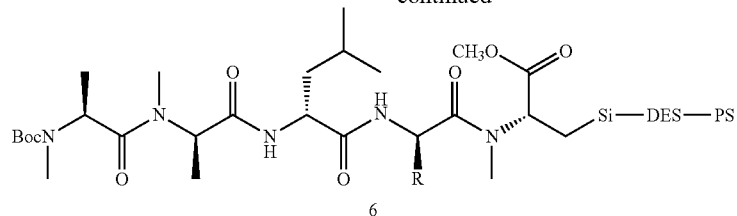
6
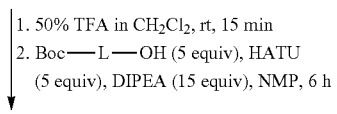
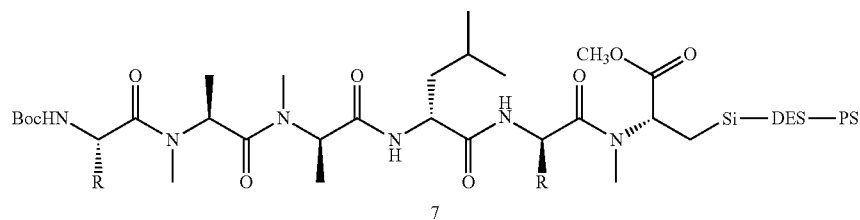
7
SCHEME 4
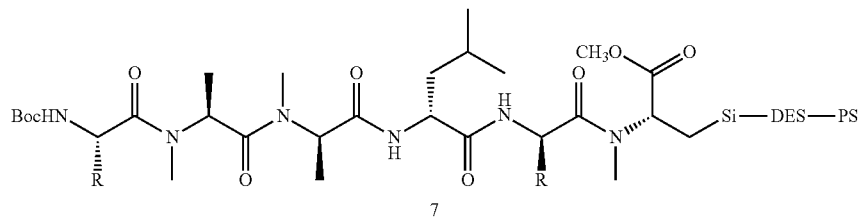
7
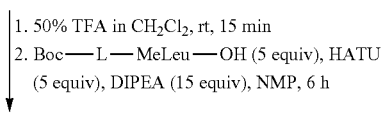
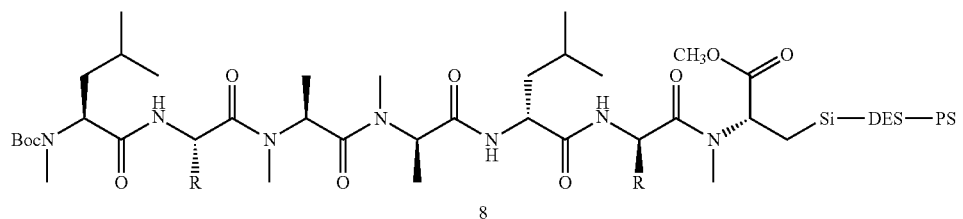
8
1. LiOH (5 equiv), THF/H₂O (7:1)
2. 50% TFA in CH₂Cl₂, rt, 15 min
3. PyBOP (5 equiv), DIPEA (15 equiv), NMP, 24 h

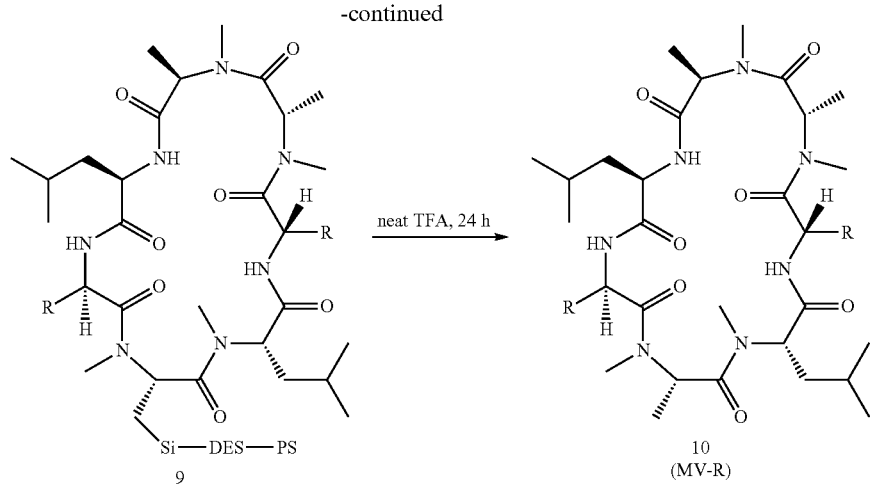

9
(MV-R) 10

General Method for Preparation of Cycloheptapeptide Derivatives.

Figure 17:
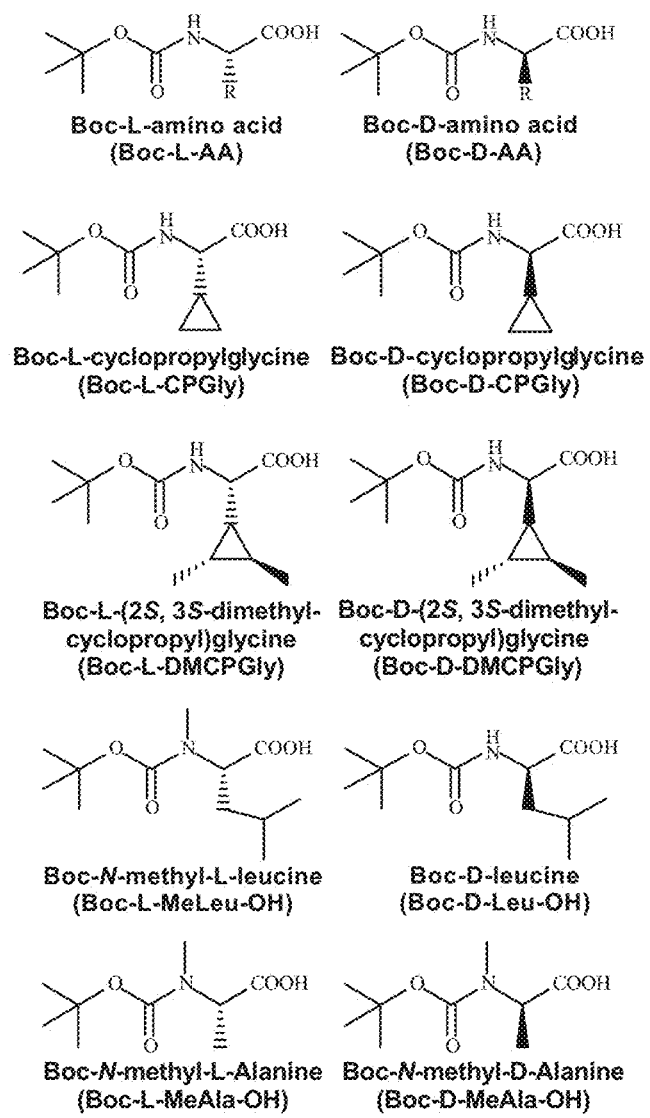
FIG. 17 shows the chemical structures of Boc-protected amino acids).
Figure 18:
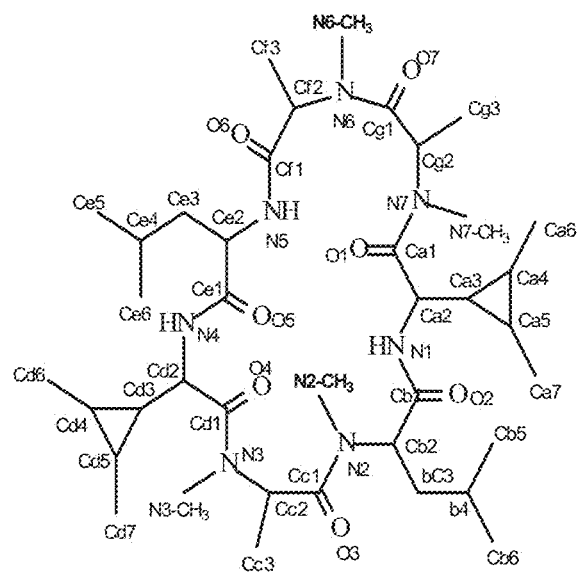
FIG. 18 shows label of the atoms of the structure of MV-A for X-ray crystallography.
Figure 19:
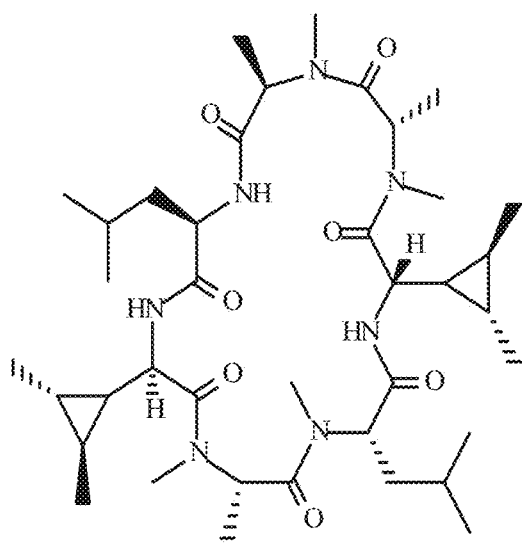
FIG. 19 shows stereochemistry of the structure of MV-A determined by X-ray crystallography.
Figure 20:
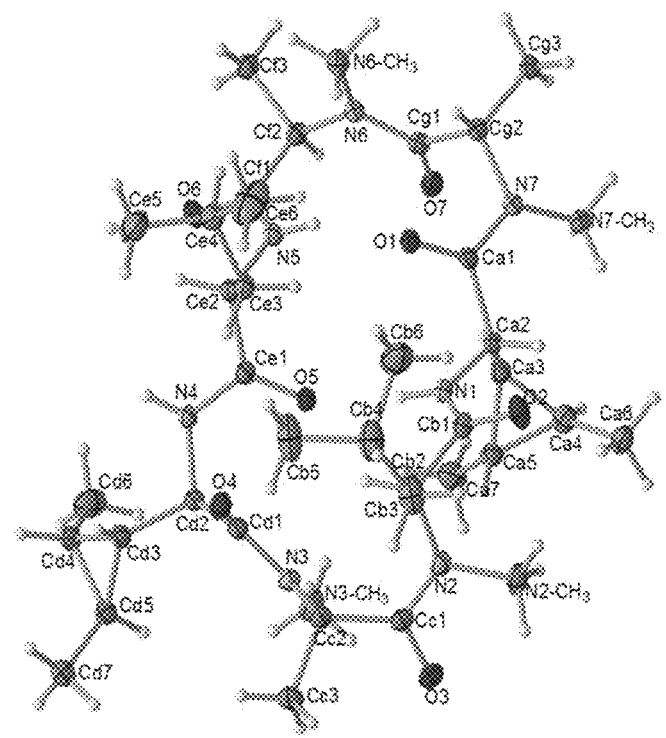
FIG. 20 shows the single-crystal X-ray structures of MV-A.

All cycloheptapeptides are synthesized based on the methods depicted in SCHEMEs 2-4, and the general experimental procedures are described as following. A suspension of resin 2 (1 g, 0.1 mmol/g) is treated with 50% TFA in $CH_2Cl_2$ (20 mL) for 15 min, then washed with $CH_2Cl_2$, 0.1 N HCl/THF, MeOH, and DMF. The washed resin is suspended in NMP (20 mL), treated with Boc-D-AA (5 eq) (FIG. 17), HATU (5 eq), and DIPEA (15 eq) for 6 h. After being washed with DMF, 0.1 N HCl/THF, MeOH, and DMF, the resin is cycled through the same set of conditions for deprotection, washing, coupling, and washing as above using Boc-D-Leu-OH (5 eq), Boc-D-MeAla-OH (5 eq), Boc-L-MeAla-OH (5 eq), Boc-L-AA (5 eq), and Boc-L-MeLeu-OH (5 eq) successively in the peptide elongation. After being washed with DMF, 0.1 N HCl/THF, MeOH, and DMF, the diprotected linear peptide bound to the resin (8) is shaken with LiOH (5 eq) in $THF/H_2O$ (7:1, 20 mL) at room temperature for 12 h. After being washed with DMF, 0.1 N HCl/THF, MeOH, and DMF, the resin is treated with 50% TFA in $CH_2Cl_2$ (20 mL) for 15 min, then washed with $CH_2Cl_2$, 0.1 N HCl/THF, MeOH, and DMF. Cyclization to prepare 9 is carried out by treatment of the resin in NMP (20 mL) with PyBOP (5 eq), and DIPEA (15 eq) for 24 hours followed by washing with DMF, 0.1 N HCl/THF, MeOH, and $CH_2Cl_2$. The resin is then treated with neat TFA for 24 hours at room temperature to release the cyclic peptide. The cleavage solution is filtered, and the resin is rinsed with $CH_2Cl_2$ (20 mL). Concentration of the combined filtrates gives the crude product, which is filtered through a short silica gel plug with ethyl acetate to afford the desired compound 10.

In the reactions depicted in SCHEMEs 2-4, when Boc-D-AA and Boc-L-AA are selected as Boc-D-DMCPGly and Boc-D-DMCPGly respectively (FIG. 17), the compound MV-A is produced.

In the reactions depicted in SCHEMEs 2-4, when Boc-D-AA and Boc-L-AA are selected as Boc-D-Leu-OH and Boc-D-DMCPGly respectively (FIG. 17), the compound MV-C is produced.

In the reactions depicted in SCHEMEs 2-4, when Boc-D-AA and Boc-L-AA are selected as Boc-D-CPGly and Boc-L-CPGly (FIG. 17) respectively, the compound MV-D is produced.

MV-A is obtained as a white powder with a molecular formula of $C_{39}H_{67}N_7O_7$ determined by positive HRESIMS and NMR studies $^1$H NMR (400 MHz, $CDCl_3$, J in Hz) δ (in ppm with reference to the signal of $CDCl_3$ at δ 7.24 ppm) amino acid a [7.90 (1H, d, J=8.9, NH-n1), 4.67 (1H, dd, J=8.6, 5.8, H-a2), 1.06 (3H, d, J=5.9, $CH_3$-a7), 0.92 (3H, d, J=6.0, $CH_3$-a6), 0.76 (2H, m, H-a3 and H-a5), 0.25 (1H, sextet, J=5.3, H-a4)], amino acid b [4.18 (1H, dd, J=10.1, 4.7, H-b2), 2.89 (3H, s, n2-$CH_3$), 2.05 (1H, ddd, J=13.5, 10.3, 5.2, H-b3a), 1.44 (1H, m, H-b4), 1.16 (1H, ddd, J=13.2, 8.2, 4.9, H-b3b), 0.95 (3H, d, J=6.5, $CH_3$-b5), 0.89 (3H, d, J=6.6, $CH_3$-b6)], amino acid c [5.44 (1H, q, J=6.3, H-c2), 3.05 (3H, s, n3-$CH_3$), 1.27 (3H, d, J=6.5, $CH_3$-c3)], amino acid d [6.27 (1H, brd, J=5.3, NH-n4), 4.13 (1H, dd, J=10.0, 5.5, H-d2), 1.05 (3H, d, J=5.7, $CH_3$-d7), 1.00 (3H, d, J=5.9, $CH_3$-d6), 0.73 (1H, m, H-d5), 0.70 (1H, m, H-d3), 0.54 (1H, sextet, J=5.1, H-d4)], amino acid e [7.51 (1H, brd, J=9.0, NH-n5), 4.47 (1H, brt, J=8.8, H-e2), 1.80 (1H, brt, J=10.2, H-e3a), 1.60-1.66 (2H, m, H-e3b and H-e4), 0.98 (3H, d, J=5.8, $CH_3$-e5), 0.91 (3H, d, J=6.2, $CH_3$-e6)], amino acid f [5.36 (1H, q, J=7.2, H-f2), 2.98 (3H, s, n6-$CH_3$), 1.32 (3H, d, J=7.2, $CH_3$-f3)], amino acid g [4.89 (1H, brq, J=7.4, H-g2), 3.16 (3H, s, n7-$CH_3$), 1.38 (3H, d, J=7.4, $CH_3$-g3)]. HRTOF positive ESIMS m/s calcd for $C_{39}H_{68}N_7O_7$: 746.5180 $[M+1]^+$, found: 746.5182 $[M+1]^+$. To confirm the structure and the stereochemistry, MV-A was crystallized in acetone/n-hexane (3:1) to afford a crystal of the monoclinic space group $P2_12_12$ which was analyzed by X-ray crystallography (FIGS. 18-20). The configuration was determined by the measurement of the Flack parameter, which is calculated during the structural refinement. In our study, the final refinement of the crystal of 1 resulted in a Flack parameter of 0, allowing an unambiguous assignment of the stereochemistry of the structure. Crystal data for MV-A (from acetone/n-hexane 3:1) belong to the monoclinic spacnoclinic space group $P2_12_12$. The crystal data: $C_{39}H_{67}N_7O_7$, M=745.51, a=32.9901 (7) Å, b=23.6494 (6) Å, c=12.0008 (2) Å, α=90.00°, β=90.00°, γ=90.00°, V=9362.98 Å$^3$, Z=4.

MV-B was obtained from the decaying wood of *Maytenus variabilis*. To obtain MV-B from the decaying wood of wood of *Maytenus variabilis*, the inventor first collected the stem barks of the decayed woods of *Maytenus variabilis*. Then a chloroform extract and a methanol extract were prepared from the collected stem barks immediately after the collection. These extracts are herein identified as the chloroform extract (MVSB-CLE) and the methanol extract (MVSB-MTE), respectively. These extracts were stored in a −20° C. freezer for later analysis and study against the chloroform extract and the methanol extract taken from the stem barks after further treatment. The inventor then processed the remaining part of the collected stem barks was soaked into water for 24 hours at room temperature. The soaked stem barks were then taken out of the water and placed on the floor. The stem barks were kept moistened by spraying with water from time to time. The stems were kept in the wet status at room temperature for 60 days, after which time all the stem barks were rotten. The stem barks were then put in an oven at 40° C. for 3 days. The stem barks were then milled and extracted with methanol to afford an extract, which was defatted with n-hexane and then partitioned with chloroform to afford a chloroform extract. Subsequent separation of the chloroform extract led to the isolation of the inventor's target compounds (e.g. MV-B). The inventor has analyzed the various extracts to determine if the further treatment of the stem barks lead to the production of new compounds. Notably, compound MV-B is not present in MVSB-CLE and MVSB-MTE, the extractions taken after collection of the stem barks and before further laboratory treatment. MV-B is obtained as a white powder with a molecular formula of $C_{39}H_{67}N_7O_8$ determined by positive HRESIMS and NMR studies $^1$H NMR (400 MHz, CDCl$_3$, J in Hz) δ (in ppm with reference to the signal of CDCl$_3$ at δ 7.24 ppm) amino acid a [7.93 (1H, d, J=8.6, NH-n1), 4.60 (1H, dd, J=8.5, 5.9, H-a2), 1.04 (3H, d, J=6.0, CH$_3$-a7), 0.92 (3H, d, J=5.8, CH$_3$-a6), 0.85 (1H, m, H-a3), 0.78 (1H, sextet, J=5.8, H-a5), 0.24 (1H, sextet, J=5.3, H-a4)], amino acid b [4.11 (1H, brdd, J=11.0, 3.0, H-b2), 3.42 (1H, dd, J=11.4, 5.0, H-b6a), 3.31 (1H, brdd, J=11.1, 5.4, H-b6b), 2.88 (3H, s, n2-CH$_3$), 2.36 (1H, ddd, J=13.7, 11.4, 6.2, H-b3a), 1.54 (1H, brnonet, J=6.4, H-b4), 1.14 (1H, ddd, J=13.5, 6.4, 3.5, H-b3b), 0.98 (3H, d, J=6.9, CH$_3$-b5)], amino acid c [5.45 (1H, q, J=6.6, H-c2), 3.04 (3H, s, n3-CH$_3$), 1.26 (3H, d, J=6.5, CH$_3$-c3)], amino acid d [6.15 (1H, brd, J=4.6, NH-n4), 4.08 (1H, brdd, J=10.2, 5.1, H-d2), 1.05 (3H, d, J=5.9, CH$_3$-d7), 1.01 (3H, d, J=5.9, CH$_3$-d6), 0.69-5.75 (2H, m, 0.73 (1H, m, H-d3 and H-d5), 0.56 (1H, sextet, J=5.2, H-d4)], amino acid e [7.52 (1H, brd, J=9.0, NH-n5), 4.61 (1H, overlap, H-e2), 1.76 (1H, brt, J=10.3, H-e3a), 1.60-1.67 (2H, m, H-e3b and H-e4), 1.00 (3H, d, J=5.6, CH$_3$-e5), 0.92 (3H, d, J=5.8, CH$_3$-e6)], amino acid f [5.37 (1H, q, J=7.0, H-f2), 2.97 (3H, s, n6-CH$_3$), 1.33 (3H, d, J=7.2, CH$_3$-f3)], amino acid g [4.92 (1H, brq, J=7.3, H-g2), 3.16 (3H, s, n7-CH$_3$), 1.39 (3H, d, J=7.4, CH$_3$-g3)]. HRTOF positive ESIMS m/s calcd for $C_{39}H_{68}N_7O_8$: 762.5129 [M+1]$^+$, found: 762.5133 [M+1]$^+$.

MV-C is obtained as a white powder with a molecular formula of $C_{38}H_{67}N_7O_7$ determined by positive HRESIMS and NMR studies $^1$H NMR (400 MHz, CDCl$_3$, J in Hz) δ (in ppm with reference to the signal of CDCl$_3$ at δ 7.24 ppm) amino acid a [7.84 (1H, d, J=8.8, NH-n1), 4.68 (1H, m, H-a2), 1.06 (3H, d, J=6.0, CH3-a7), 0.86-0.98 (3H, overlap, CH$_3$-a6), 0.75 (2H, m, H-a3 and H-a5)], amino acid b [4.34 (1H, m, H-b2), 2.86 (3H, s, n2-CH$_3$), 2.00 (1H, dm, H-b3a), 1.45 (1H, nontet, J=6.7, H-b4), 1.19 (1H, m, H-b3b), 0.86-0.98 (6H, overlap, CH$_3$-b5 and CH$_3$-b6)], amino acid c [5.39 (1H, q, J=6.4, H-c2), 3.07 (3H, s, n3-CH$_3$), 1.26 (3H, d, J=6.4, CH$_3$-c3)], amino acid d [6.46 (1H, brs, NH-n4), 4.78 (1H, m, H-d2), 1.73 (1H, m, H-d4), 1.58 (1H, m, H-d3a), 1.36 (1H, m, H-d3b), 0.86-0.98 (6H, overlap, CH$_3$-d5 and CH$_3$-d6)], amino acid e [7.45 (1H, brd, J=8.5, NH-n5), 4.24 (1H, m, H-e2), 1.84 (1H, brt, J=9.7, H-e3a), 1.65 (1H, m, H-e3b), 1.59 (1H, m, H-e4), 0.86-0.98 (6H, overlap, CH$_3$-e5 and CH$_3$-e6)], amino acid f [5.33 (1H, q, J=7.3, H-f2), 2.99 (3H, s, n6-CH$_3$), 1.32 (3H, d, J=7.2, CH$_3$43)], amino acid g [4.86 (1H, brq, J=7.5, H-g2), 3.16 (3H, s, n7-CH$_3$), 1.39 (3H, d, J=7.1, CH$_3$-g3)]. HRTOF positive ESIMS m/s calcd for $C_{38}H_{68}N_7O_7$: 734.5180 [M+1]$^+$, found: 734.5176 [M+1]$^+$.

MV-D is obtained as a white powder with a molecular formula of $C_{35}H_{59}N_7O_7$ determined by positive HRESIMS and NMR studies $^1$H NMR (400 MHz, CDCl$_3$, J in Hz) δ (in ppm with reference to the signal of CDCl$_3$ at δ 7.24 ppm) amino acid a [8.10 (1H, d, J=8.1, NH-n1), 4.91 (1H, brt, J=7.5, H-a2), 0.25-0.66 (5H, m, H-a3, H$_2$-a4 and H$_2$-a5)], amino acid b [4.03 (1H, m, H-b2), 2.89 (3H, s, n2-CH$_3$), 1.77-1.95 (1H, m, H-b3a), 1.55-1.75 (1H, m, H-b4), 1.13-1.23 (1H, m, H-b3b), 0.87-0.97 (6H, m, CH$_3$-b5 and CH$_3$-b6)], amino acid c [5.38 (1H, brq, J=6.9, H-c2), 3.13 (3H, s, n3-CH$_3$), 1.35 (3H, d, J=7.0, CH$_3$-c3)], amino acid d [6.93 (1H, brs, NH-n4), 4.41 (1H, brt, J=7.6, H-d2), 0.25-0.66 (5H, m, H-d3, H$_2$-d4 and H$_2$-d5)], amino acid e [7.37 (1H, brd, J=7.9, NH-n5), 4.65 (1H, brt, J=8.0, H-e2), 1.77-1.95 (1H, m, H-e3a), 1.55-1.75 (2H, m, H-e3b and H-e4), 0.87-0.97 (6H, m, CH$_3$-e5 and CH$_3$-e6)], amino acid f [5.26 (1H, q, J=7.2, H-f2), 3.03 (3H, s, n6-CH$_3$), 1.33 (3H, d, J=7.3, CH$_3$-f3)], amino acid g [4.83 (1H, brq, J=7.7, H-g2), 3.24 (3H, s, n7-CH$_3$), 1.42 (3H, d, J=7.3, CH$_3$-g3)]. HRTOF positive ESIMS m/s calcd for $C_{35}H_{60}N_7O_7$: 690.4554 [M+1]$^+$, found: 690.4555 [M+1]$^+$.

These cycloheptapeptide compounds (MV-A, MV-B, MV-C and MV-D) have been evaluated for their anticancer activity in both in vitro and in vivo studies.

The cycloheptapeptide compounds have been tested against a panel of cancer cell lines comprising KB, HCT116, LNCaP, A549, MCF7, HL60, Hela and A375 in vitro. MV-A demonstrates cell killing activity with IC$_{50}$ values ranging from 0.05-1.5 nM. MV-B demonstrates cell killing activity with IC$_{50}$ values ranging from 0.7-9.1 nM. MV-C demonstrates cell killing activity with IC$_{50}$ values ranging from 12-60 nM. MV-D demonstrates no inhibition activity against the cancer cells at 2 μM.

MV-A is evaluated in the murine hollow fiber tumor animal model, which demonstrates MV-A has potent anticancer activity against lung, colon and breast cancers (Table 6). The experiments reveal that i.p. (intraperitoneal), i.v. (intravenous), or oral administration of MV-A at the doses of 0.05 and 0.1 mg/kg of MV-A result in 18.2% and 56.6% inhibition of cell growth of a lung cancer cell line (A549) implanted at the i.p. compartments relative to the control, respectively. At the doses of 0.1, 0.2 and 0.8 mg/kg, MV-A inhibits the growth of a colon cancer cell line (HCT116) by 33.1%, 53.3% and 65.0% at the i.p. sites, respectively. At the doses of 0.05, 0.1, 0.2 and 0.4 mg/kg, MV-A inhibits the growth of a breast cancer cell line (MCF7) by 76.8%, 68.3% and 66.7% at the i.p. sites, respectively. At a dose of 0.4 mg/kg, MV-A also inhibits the growth of the breast cancer cell line by 56.0% at the s.c. (subcutaneous) sites. At the doses of 0.2 and 0.4 mg/kg, MV-A inhibits the growth of a melanoma cancer cell line (A375) by 35.3% and 67.4% at the i.p. sites, respectively. MV-A inhibits the growth of a cervical cancer cell line (Hela) by 45.8% and 82.7% at the i.p. sites, respectively. At a dose of 0.4 mg/kg, MV-A also inhibits the growth of the cervical cancer cell line by 52.8% at the s.c. sites.

TABLE 6

Hollow fiber in vivo data of MV-A

| Compound | Cell line | Dose (mg/kg) | Inhibition (%) | P |
|---|---|---|---|---|
| MV-A | A549-IP | 0.05 | 18.2 | 0.6 |
| | A549-SC | 0.05 | 0 | — |
| | A549-IP | 0.1 | 56.6 | 0.04 |
| | A549-SC | 0.1 | 36.4 | 0.1 |
| | HCT116-IP | 0.1 | 33.1 | 0.007 |
| | HCT116-SC | 0.1 | 0 | — |
| | HCT116-IP | 0.2 | 53.3 | 0.03 |
| | HCT116-SC | 0.2 | 15.1 | 0.4 |
| | HCT116-IP | 0.8 | 65.0 | 0.01 |
| | HCT116-SC | 0.8 | 12.7 | 0.5 |
| | MCF7-IP | 0.05 | 65.9 | 0.02 |
| | MCF7-SC | 0.05 | 0 | — |
| | MCF7-IP | 0.1 | 76.8 | 0.01 |
| | MCF7-SC | 0.1 | 0 | — |
| | MCF7-IP | 0.2 | 68.3 | 0.02 |
| | MCF7-SC | 0.2 | 13.9 | — |
| | MCF7-IP | 0.4 | 66.7 | 0.05 |
| | MCF7-SC | 0.4 | 56.0 | 0.2 |
| | A375-IP | 0.2 | 35.3 | 0.03 |
| | A375-SC | 0.2 | 17.2 | — |
| | A375-IP | 0.4 | 67.4 | 0.01 |
| | A375-SC | 0.4 | 27.8 | — |
| | Hela-IP | 0.2 | 45.8 | 0.03 |
| | Hela-SC | 0.2 | 23.2 | — |
| | Hela-IP | 0.4 | 82.7 | 0.001 |
| | Hela-SC | 0.4 | 52.8 | 0.02 |
| Paclitaxel | A549-IP | 2.0 | 39.8 | 0.1 |
| | A549-SC | 2.0 | 0 | — |
| | HCT116-IP | 2.0 | 60.4 | 0.006 |
| | HCT116-SC | 2.0 | 0 | — |
| | MCF7-IP | 2.0 | 70.7 | 0.01 |
| | MCF7-SC | 2.0 | 0 | — |
| | A375-IP | 2.0 | 38.1 | 0.1 |
| | A375-SC | 2.0 | 7.8 | — |
| | Hela-IP | 2.0 | 69.5 | 0.01 |
| | Hela-SC | 2.0 | 11.1 | — |

In the conversion calculation from the tested animal doses to human clinical doses is based on the "Guidance for Industry Estimating the Maximum Safe Starting Dose in Initial Clinical Trials for Therapeutics in Adult Healthy Volunteers", which was published by U.S. Department of Health and Human Services, Food and Drug Administration, Center for Drug Evaluation and Research, July 2005; Page 7: Table 1: Human equivalent dosage (mg/kg)=animal dosage (mg/kg)×(animal Km/human Km), wherein mouse Km is 3 and human Km is 37. Thus, 0.05 mg/kg per mouse body weight corresponds to 0.0041 mg/kg per patient body weight in humans. Correspondingly, 0.1 mg/kg per mouse body weight corresponds to 0.0081 mg/kg per patient weight (weight in humans); 0.2 mg/kg per mouse body weight corresponds to 0.0162 mg/kg per patient weight (weight in humans); 0.4 mg/kg per mouse body weight corresponds to 0.0324 mg/kg per patient weight (weight in humans); and 0.8 mg/kg per mouse body weight corresponds to 0.0649 mg/kg per patient weight (weight in humans).

MV-A is further evaluated for its anticancer activity in HCT116 and MCF7 xenograft mouse models.

Figure 21:
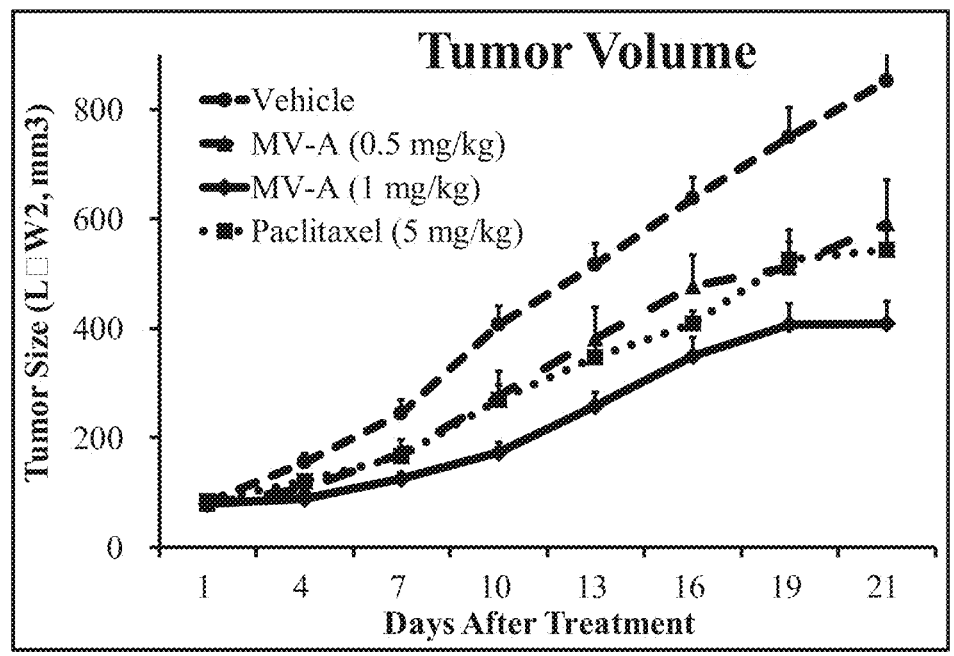
FIG. 21(A) shows inhibition of HCT116-tumor xenograft growth by MV-A. Tumor growth curve.
FIG. 21(B) shows inhibition of HCT116-tumor xenograft growth by MV-A. Excised tumor weights at the end point; P versus control (% inhibition): MV-A high dose=0.0000078 (52.8%), MV-A low dose=0.0031 (31.1%), and paclitaxel=0.00045 (37.6%).
Figure 21:
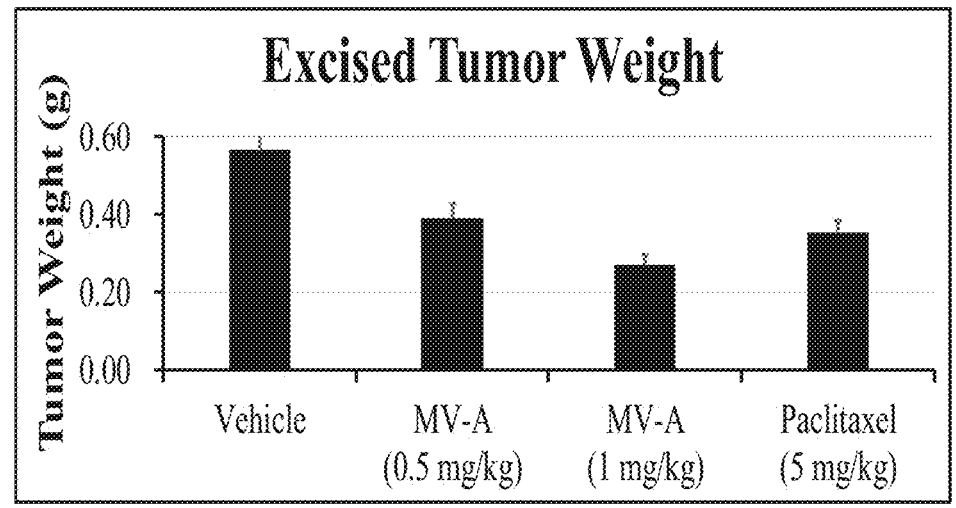

The treatment started on the 6$^{th}$ day when the HCT116-tumor reached approximately 100 mm$^3$ (L×W×W). Two doses of MV-A (0.5 and 1.0 mg/kg), paclitaxel (5 mg/kg), maytansine (0.1 mg/kg) and vehicle were administered via i.p. (intraperitoneal), i.v. (intravenous), or oral, respectively, to the tumor-bearing mice every other day for 21 days (10 mice/group). All mice died for the maytansine group after the first two treatments. The HCT 116 xenograft experiment showed that MV-A inhibits tumor growth by 31.1% and 52.8% at the doses of 0.5 and 1.0 mg/kg, respectively (FIGS. 21(A)-21(B)). A weight loss of 1-2 g is observed for the MV-A groups after the first two treatments, but the weights of the mice are kept relatively stable after the first two treatments. All mice died for the maytansine group after the initial two treatments at the dose of 0.1 mg/kg, indicating the highly toxicity of maytansine. The antitumor response by MV-A at the dose of 1.0 mg/kg is apparently superior to that of paclitaxel at the dose of 5.0 mg/kg (37.6% inhibition).

In the conversion calculation from the tested animal doses to human clinical doses is based on the "Guidance for Industry Estimating the Maximum Safe Starting Dose in Initial Clinical Trials for Therapeutics in Adult Healthy Volunteers", which was published by U.S. Department of Health and Human Services, Food and Drug Administration, Center for Drug Evaluation and Research, July 2005; Page 7: Table 1: Human equivalent dosage (mg/kg)=animal dosage (mg/kg)×(animal Km/human Km), wherein mouse Km is 3 and human Km is 37. Thus, 0.5 mg/kg per mouse body weight corresponds to 0.0405 mg/kg per patient weight (weight in humans); and 1.0 mg/kg per mouse body weight corresponds to 0.0811 mg/kg per patient weight (weight in humans).

Figure 22:
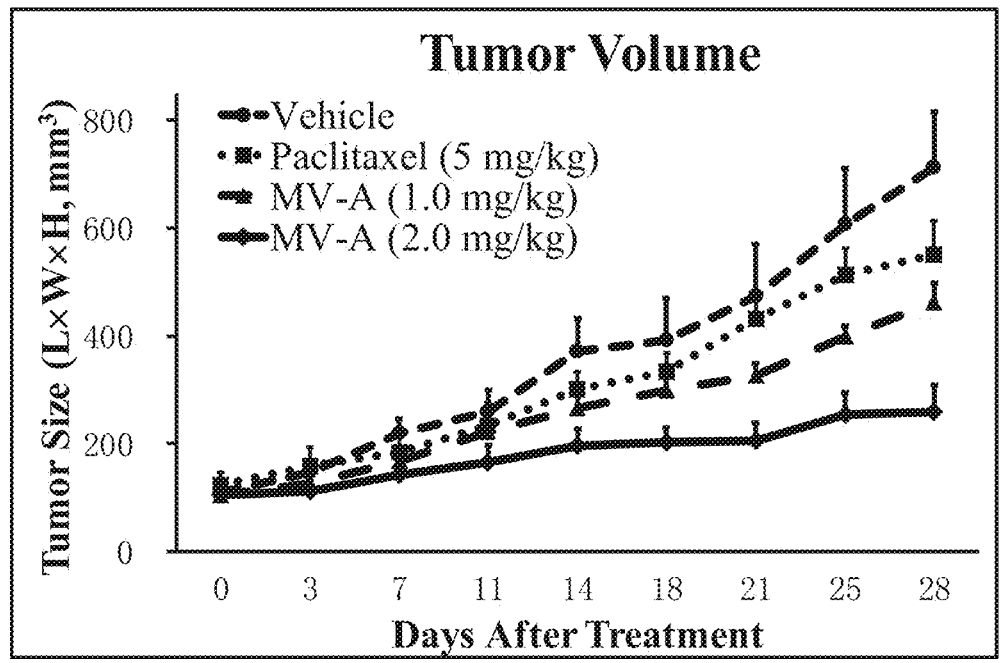
FIG. 22(A) shows inhibition of MCF7-tumor xenograft growth by MV-A. Tumor growth curve.
FIG. 22(B) shows inhibition of MCF7-tumor xenograft growth by MV-A. Excised tumor weights at the end point; P versus control (% inhibition): MV-A high dose=0.0005 (72.6%), MV-A low dose=0.0006 (48.1%), and paclitaxel=0.08 (28.2%); C) Body growth weights of mice.
Figure 22:
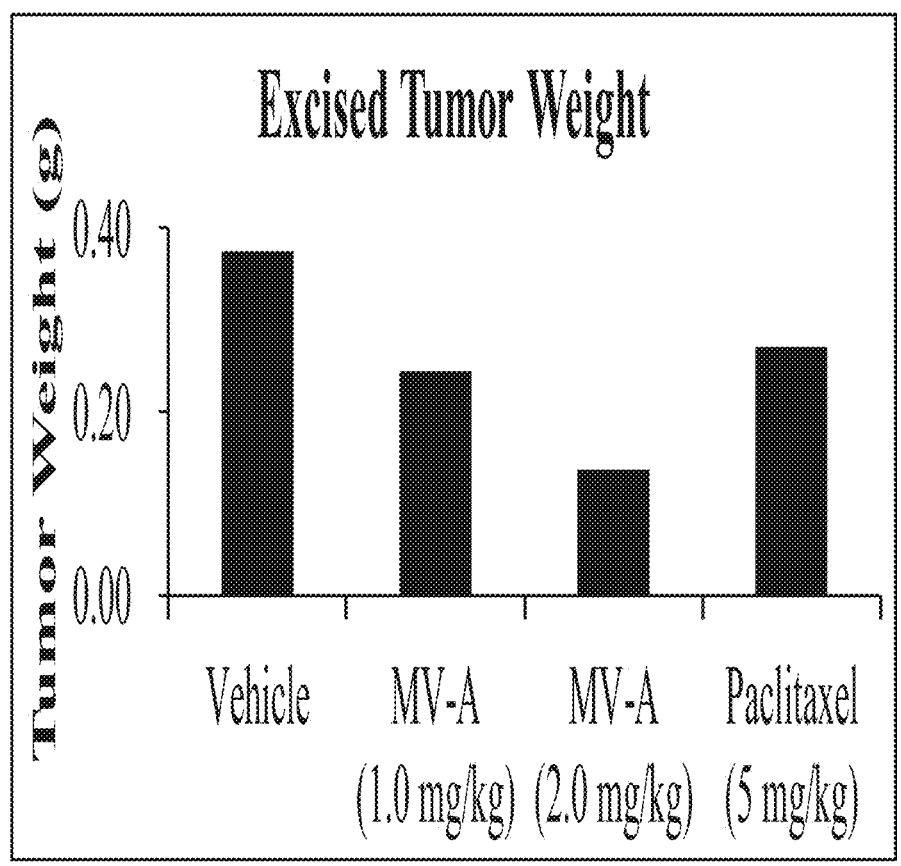

The treatment started on the 12$^{th}$ day when the MCF7-tumor size reached approximately 100 mm$^3$ (L×W×H). Two doses of MV-A (1.0 and 2.0 mg/kg), paclitaxel (5 mg/kg), and vehicle were administered via i.p. (intraperitoneal), i.v. (intravenous), or oral respectively, to the tumor-bearing mice twice a week for 3 weeks (8 mice/group). The MCF7 xenograft experiment showed that MV-A inhibited tumor growth by 48.1% and 72.6% at the doses of 1.0 and 2.0 mg/kg, respectively (FIGS. 22(A)-22(B)). A weight loss of 1-2 g is observed for the MV-A groups after the first two treatments, but the weights of the mice are kept relatively stable after the first two treatments. The antitumor response by MV-A at the two doses is apparently superior to that of paclitaxel at the dose of 5.0 mg/kg (28.2% inhibition).

In the conversion calculation from the tested animal doses to human clinical doses is based on the Guidance for Industry Estimating the Maximum Safe Starting Dose in Initial Clinical Trials for Therapeutics in Adult Healthy Volunteers, which was published by U.S. Department of Health and Human Services, Food and Drug Administration, Center for Drug Evaluation and Research, July 2005; Page 7: Table 1: Human equivalent dosage (mg/kg)=animal dosage (mg/kg)×(animal Km/human Km), wherein mouse Km is 3 and human Km is 37. Thus, 1.0 mg/kg per mouse body weight corresponds to 0.0811 mg/kg per patient weight (weight in humans); and 2.0 mg/kg per mouse body weight corresponds to 0.162 mg/kg per patient weight (weight in humans).

MV-A, MV-B, MV-C and MV-D are evaluated for their anti-obesity effects in 3T3-L1 murine adipocytes. 3T3-L1 cells are cultured in the presence of insulin to induce adipocyte differentiation. With treatment of the differentiation cells by different concentrations of the compounds, triglyceride levels as indication of fat accumulation in the differentiation cells are measured to determine the anti-obesity effects of MV-A, MV-B, MV-C and MV-D. MV-A demonstrates the anti-obesity activity with an EC$_{50}$ value of 0.3 nM (the cell viability with an IC$_{50}$ value of 12.9 nM. MV-B demonstrates the anti-obesity activity with an EC$_{50}$ value of 2.6 nM (the cell viability with an IC$_{50}$ value of 83.7 nM. MV-C demonstrates the anti-obesity activity with an EC$_{50}$ value of 38.9 nM (the cell viability with an IC$_{50}$ value of 689.4 nM). MV-D demonstrates the anti-obesity activity with an EC$_{50}$ value of 13.3 nM (the cell viability with an IC$_{50}$ value of more than 5.0 µM). MV-D shows potent anti-obesity activity with low toxicity. In the animal studies, the inventor demonstrates that the body weights of mice are significantly decreased after drug treatment of MV-A. The average weight of mice (10 mice) drops 1-2 g after the first two treatments (intravenous, intraperitoneal or oral administration) with MV-A at the doses of 1 mg/kg and 2 mg/kg, respectively, but the weight of the mice is kept relatively stable after the first two treatments. No mice die during the treatments, and the average weight of mice gains back after the treatment stopped, which showed that the effects of compound MV-A on the mice are reversible. No sign of toxicity is observed from dissection of the mice.

In the conversion calculation from the tested animal doses to human clinical doses is based on the Guidance for Industry Estimating the Maximum Safe Starting Dose in Initial Clinical Trials for Therapeutics in Adult Healthy Volunteers, which was published by U.S. Department of Health and Human Services, Food and Drug Administration, Center for Drug Evaluation and Research, July 2005; Page 7: Table 1: Human equivalent dosage (mg/kg)=animal dosage (mg/kg)×(animal Km/human Km), wherein mouse Km is 3 and human Km is 37. Thus, 1.0 mg/kg per mouse body weight corresponds to 0.0811 mg/kg per patient weight (weight in humans); and 2.0 mg/kg per mouse body weight corresponds to 0.162 mg/kg per patient weight (weight in humans).

Since the low toxicity of MV-D, the compound is evaluated for its antiviral activity against HIV (human immunodeficiency virus). It displays anti-HIV potential with an $IC_{50}$ value of 1.24 µM.

The inventor has discovered the anticancer, anti-obesity and anti-HIV compounds in in vitro and in vivo studies.

Cell Culture Panel Bioassays.

Pure compounds are evaluated against the human cancer cell lines comprising our cytotoxicity screening panel. Cytotoxicity assays involving oral epidermoid (KB), colon (HCT116), prostate (LNCaP), breast (MCF7), Hela (cervical), leukemia (HL-60) melanoma (A375) and lung (A549) carcinoma cell lines, are performed using sulforhodamine B according to established protocols (Zhang et al., Journal of Medicinal Chemistry 2006; 49: 693-708; and Jutiviboonsuk A et al., Phytochemistry 2005; 66: 2745-2751.). KB and A375 cells are maintained in DMEM (Dulbecco's modified Eagle medium) medium. LNCaP and HL60 cells are maintained in RPMI1640 medium with hormone-free 10% heat-activated FBS (fetal bovine serum) supplemented with 0.1 nM testosterone. MCF7 and Hela cells are maintained and assayed in MEME (Minimum Essential Medium Eagle) medium containing 10 mg/L of insulin. HCT116 cells are maintained in McCoy's 5A medium supplemented with 10% fetal bovine serum. A549 cells are maintained in RPMI-1640 medium supplemented with 10% FCS. Serial dilutions of the compounds are prepared using 10% aqueous DMSO as solvent. The 190 µL cell suspension ($3×10^4$ cells in 1 ml media) is incubated with 10 µL sample solutions, in triplicate, in 96-well tissue culture plate at 37° C. in a humidified atmosphere of 5% $CO_2$ in air for 72 hours. 10 µL 10% aqueous DMSO is used as control group. Then the cells are fixed to plastic substratum by the addition of 100 µL cold 20% aqueous trichloroacetic acid and washing with water after incubation at 4° C. for 30 min. After staining cells with 100 µL of 0.4% sulforhodamine B in 1% aqueous AcOH for 30 min, unbound dye is removed by rinsing with 1% aqueous AcOH. The bound dye is solubilized with 200 µL 10 mM unbuffered Tris base, pH 10, and the optical density is measured at 515 nm using an ELISA plate reader. The average data are expressed as a percentage, relative to the control. The $IC_{50}$ values, the dose that inhibit cell growth by 50%, are calculated using nonlinear regression analysis (percent survival versus concentration).

3T3-L1 Cell Culture Bioassay.

Pure compounds are evaluated against 3T3-L1 cell line for their potential anti-obesity activity. The preadipocyte murine cell line 3T3-L1 is cultured in normal DMEM medium counting with 10% FCS and 90 U/mL penicillin-streptomycin at 37° C. in a humidified atmosphere of 5% $CO_2$ in air for 72 hours. After the cells reach 100% confluence, the culture medium is changed to a differentiation DMEM medium containing 10% FCS, 1 mM dexamethasone, 0.5 mM 3-isobutyl-1-methylxanthine (IBMX), 90 U/mL penicillin, 90 mg/mL streptomycin and 10 µg/mL insulin for induction of the adipocyte form of the 3T3-L1 cells. After 2 days, the differentiation medium is changed back to the normal DMEM medium and refreshed with the normal medium every 2 days. After incubation of additional 7 days, the cells are seeded in two sets of 96-well plates (about 10,000 cells per well). The test compounds in different concentrations are then added to the wells with 0.5% aqueous DMSO as control group. After incubation of 7 days, the differentiated 3T3-L1 adipocytes are treated with 2% Triton-X 100 (10 mL/well) for 30 min at room temperature followed by sonication for 1 min. Fat accumulation is determined by measuring the liberated triglyceride using a Wato Triglyceride E-test Kit with the absorbance at 630/690 nm. The fat-accumulation rate is calculated as a percentage of the DMSO control. The $EC_{50}$ values, the dose that inhibit fat accumulation by 50%, are calculated using nonlinear regression analysis (percent survival versus concentration). The cell viability of the differentiated 3T3-L1 adipocytes in another 96-well plate is treated with a Wako Cell Counting Kit-8 Test and measured with the absorbance at 450 nm. The cell viability is calculated as a percentage of the control. The $IC_{50}$ values, the dose that inhibit cell growth by 50%, are calculated using nonlinear regression analysis (percent survival versus concentration).

Hollow Fiber Animal Study.

All animal studies are approved and performed according to Animal Care and Use Guidelines of the Animal Ethics Committee at Hong Kong Baptist University and performed following Animal Care and Use guidelines set by NIH (National Institute of Health, USA). Hollow fiber tests are well known in the art for providing preliminary indications of therapeutic efficacy (Mi et al. J. Nat. Prod. 2002, 65: 842-850). In hollow fiber tests, human tumor cell lines currently employed in cell cultures are grown inside semi-permeable hollow fibers to form heterogeneous solid tumor models. The hollow fibers containing the human tumor cells are implanted in the intraperitoneal or subcutaneous compartments of host mice, and the mice treated with the test compound of interest administered via i.p. (intraperitoneal), i.v. (intravenous), or oral, respectively (Hollingshead et al., Life Sciences 1995, 57: 131-141). By evaluating the test compound's inhibition of tumor cell growth versus the toxic response in the host, a preliminary estimate of therapeutic efficacy is provided in a cost- and time effective manner.

Antitumor animal study. All animal studies were approved and performed according to Animal Care and Use Guidelines of the Animal Ethics Committee at Hong Kong Baptist University and performed following Animal Care and Use guidelines set by NIH (National Institute of Health, USA). BALB/c nude mice, SPF class, male or female, 5-6 weeks old, were purchased from Charles River Laboratories. Before the experiment, it is one week of acclimatization to SPF class laboratory conditions. MV-A is tested for its anticancer activity against HCT116 and MCF7 cancer cells using a number of nude mice (Balc/nu/nu, female) in comparison of paclitaxel and maytansine. HCT116 or MCF7 cancer cells are subcutaneously implanted with 5×10$^6$ cells in the rear flank of each mouse. Female mice receiving MCF-7 cells are implanted with an s.c. pellet of 17β-estradiol (0.72 mg/pellet) a few days prior to injection to induce tumors. After 10 days, solid tumors with average size of about 80-100 mm$^3$ appear at the implanted sites. The mice are divided into 5 groups for HCT116 cancer cells: one high dose (1.0 mg/kg: 10 mice) group of MV-A, one low dose (0.5 mg/kg: 10 mice) group of MV-A, one dose (5.0 mg/kg: 10 mice) of paclitaxel, one dose of maytansine (0.1 mg/kg) and one dose of vehicle (negative control: 10 mice). The mice are then divided into 4 groups for MCF7 cancer cells: one high dose (2.0 mg/kg: 10 mice) group of MV-A, one low dose (1.0 mg/kg: 10 mice) group of MV-A, one dose (5.0 mg/kg: 10 mice) of paclitaxel, and one dose of vehicle (negative control: 10 mice). Every other day administration via i.p. (intraperitoneal), i.v. (intravenous), or oral, respectively are scheduled for 21 days for the HCT116 groups. Twice a week injections administered via i.p. (intraperitoneal), i.v. (intravenous), or oral, respectively are scheduled for 28 days for the MCF7 groups. Weights of mice and tumor diameters are measured twice a week until the end of the experiment. The tumor size in mm$^3$ was calculated by the formula: tumor size=length×width×height (L×W×H).

Inhibitory HIV Activity Assay.

Pure compounds are evaluated for their anti-HIV activity according to established protocols (Li et al., International Journal of Molecular Sciences 2015; 16: 27978-27987.). HIV/VSV-G are produced by co-transfecting 3 g of VSV-G envelope expression plasmid with 21 g of a replication-defective HIV vector (pNL4-3-Luc-RE) [34,35] into Human embryonic kidney 293T cells (90% confluent) in 10-cm plates with PEI (Invitrogen). Eight hours post-transfection, all media is replaced with fresh, complete DMEM. Forty-eight hours post-transfection, the supernatants are collected and filtered through a 0.45-μm-pore size filter (Millipore) and the pseudovirions are directly used for infection. Target A549 cells are seeded at 104 cells per well (96-well plate) in complete DMEM. Ten microliter compound for serial concentrations (20, 10, 5, 2.5, 1.25, 0.625 and 0.3125 μg/mL) and 190 μL of the pseudovirus are incubated with target cells. Forty-eight hours post-infection, cells are lysed and prepared for luciferase assay (Promega).

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and sub-combinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and sub-ranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional cells, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

INDUSTRIAL APPLICABILITY

This invention is in the field of pharmaceuticals and chemical industries. In particular, this invention relates to new anticancer and anti-obesity agents based on the cyclic peptide natural products. The invention also includes its preparation and application method for treating cancer and obesity diseases.

If desired, the different functions discussed herein may be performed in a different order and/or concurrently with each other. Furthermore, if desired, one or more of the above-described functions may be optional or may be combined.

The embodiments disclosed herein may be implemented using general-purpose or specialized computing platforms, computing devices, computer processors, or electronic circuitries including but not limited to digital signal processors (DSP), application specific integrated circuits (ASIC), field programmable gate arrays (FPGA), and other programmable logic devices configured or programmed according to the teachings of the present disclosure. Computer instructions or software codes running in the general-purpose or specialized computing platforms, computing devices, computer processors, or programmable logic devices can readily be prepared by practitioners skilled in the software or electronic art based on the teachings of the present disclosure.

In some embodiments, the present invention includes computer storage media having computer instructions or software codes stored therein which can be used to program computers or microprocessors to perform any of the processes of the present invention. The storage media can include, but are not limited to, floppy disks, optical discs, Blu-ray Disc, DVD, CD-ROMs, and magneto-optical disks, ROMs, RAMs, flash memory devices, or any type of media or devices suitable for storing instructions, codes, and/or data.

While the foregoing invention has been described with respect to various embodiments and illustrative working examples, it is understood that other embodiments are within the scope of the present invention as expressed in the following claims and their equivalents. Moreover, the above specific examples are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

What is claimed is:

1. A method for use in the treatment or delay of progression of cancer or obesity in a subject in needs thereof by administering an effective dosage of a composition comprising a compound according to formula (II):

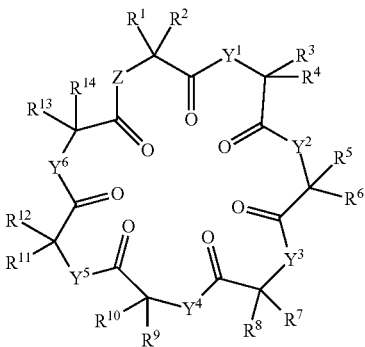

(II)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are each independently selected from hydrogen, halogen and a moiety comprising 1 to 30 plural valence atoms selected from carbon, nitrogen, oxygen and sulphur;

at least one of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is a cyclic group;

while one of $R^1$ and $R^2$, $R^3$ and $R^4$, $R^5$ and $R^6$, $R^7$ and $R^8$, $R^9$ and $R^{10}$, $R^{11}$ and $R^{12}$ or $R^{13}$ and $R^{14}$ is hydrogen, halogen, hydrocarbyl, alkoxy or cyclic group, the other one of $R^1$ and $R^2$, $R^3$ and $R^4$, $R^5$ and $R^6$, $R^7$ and $R^8$, $R^9$ and $R^{10}$, $R^{11}$ and $R^{12}$ or $R^{13}$ and $R^{14}$ is independently selected from $R^{15}$;

$R^{15}$ is independently selected from hydrogen, and hydrocarbyl optionally substituted with 1, 2, 3, 4 or 5 $R^{16}$, —$(CH_2)_k$-heterocyclyl optionally substituted with 1, 2, 3, 4 or 5 $R^{16}$, —$OR^{17}$, —$C(O)R^{18}$, —$C(O)N(R^{17})R^{18}$, —$C(O)OR^{17}$, —$OC(O)R^{17}$, —$S(O)_2R^{17}$, —$S(O)_2N(R^{17})R^{18}$, —$N(R^{17})R^{18}$, —$N(R^{17})N(R^{17})R^{18}$, —$N(R^{17})C(O)R^{18}$ and —$N(R^{17})S(O)_2R^{18}$;

$R^{16}$ is independently selected from halogen, —$OR^{17}$, —$C(O)R^{18}$, —$C(O)N(R^{17})R^{18}$, —$C(O)OR^{17}$, —$OC(O)R^{18}$, —$N(R^{17})R^{18}$ and —$N(R^{17})C(O)R^{18}$;

$R^{17}$ and $R^{18}$ are each independently hydrogen or selected from hydrocarbyl;

$Y^1$, $Y^2$, $Y^3$, $Y^4$, $Y^5$ and $Y^6$ are each independently selected from nitrogen with substitution of an $L^1$, $L^2$, $L^3$, $L^4$, $L^5$ or $L^6$ group, wherein $L^1$, $L^2$, $L^3$, $L^4$, $L^5$ and $L^6$ are each independently selected from $R^{15}$, —$C(O)R^{15}$ or —$C(O)OR^{15}$;

Z is selected from oxygen, nitrogen with substitution of an $L^7$ group, hydrocarbyl, or alkoxy;

$L^1$, $L^2$, $L^3$, $L^4$, $L^5$, $L^6$ and $L^7$ are each independently selected from $R^{15}$, —$C(O)R^{15}$ or —$C(O)OR^{15}$;

or an enantiomer thereof;

or a pharmaceutically acceptable salt or pro-drug thereof, wherein said cancer comprising colon cancer, breast cancer, prostate cancer, lung cancer, melanoma, leukemia, cervical and oral epidermoid cancer.

2. The method according to claim 1, wherein said composition comprising a compound having formula (I):

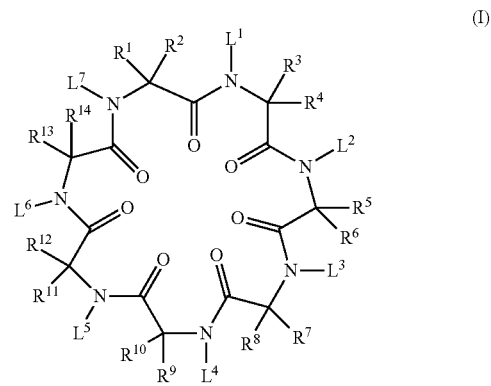

(I)

wherein $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are each independently selected from hydrogen, halogen and a moiety comprising 1 to 30 plural valence atoms selected from carbon, nitrogen, oxygen and sulphur;

at least one of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is a cyclic group;

while one of $R^1$ and $R^2$, $R^3$ and $R^4$, $R^5$ and $R^6$, $R^7$ and $R^8$, $R^9$ and $R^{10}$, $R^{11}$ and $R^{12}$ or $R^{13}$ and $R^{14}$ is hydrogen, halogen, hydrocarbyl, alkoxy or cyclic group, the other one of $R^1$ and $R^2$, $R^3$ and $R^4$, $R^5$ and $R^6$, $R^7$ and $R^8$, $R^9$ and $R^{10}$, $R^{11}$ and $R^{12}$ or $R^{13}$ and $R^{14}$ is independently selected from $R^{15}$;

$R^{15}$ is independently selected from hydrogen, and hydrocarbyl optionally substituted with 1, 2, 3, 4 or 5 $R^{16}$, —(CH$_2$)$_k$-heterocyclyl optionally substituted with 1, 2, 3, 4 or 5 R$^{16}$, —OR$^{17}$, —C(O)R$^{18}$, —C(O)N(R$^{17}$)R$^{18}$, —C(O)OR$^{17}$, —OC(O)R$^{17}$, —S(O)$_2$R$^{17}$, —S(O)$_2$N(R$^{17}$)R$^{18}$, —N(R$^{17}$)R$^{18}$, —N(R$^{17}$)N(R$^{17}$)R$^{18}$, —N(R$^{17}$)C(O)R$^{18}$ and —N(R$^{17}$)S(O)$_2$R$^{18}$;

R$^{16}$ is independently selected from halogen, —OR$^{17}$, —C(O)R$^{18}$, —C(O)N(R$^{17}$)R$^{18}$, —C(O)OR$^{17}$, —OC(O)R$^{18}$, —N(R$^{17}$)R$^{18}$ and —N(R$^{17}$)C(O)R$^{18}$;

R$^{17}$ and R$^{18}$ are each independently hydrogen or selected from hydrocarbyl;

L$^1$, L$^2$, L$^3$, L$^4$, L$^5$, L$^6$ and L$^7$ are each independently selected from R$^{15}$, —C(O)R$^{15}$ or —C(O)OR$^{15}$;

or an enantiomer thereof;

or a pharmaceutically acceptable salt or pro-drug thereof.

3. The method of claim 1, wherein said compound is an optically pure stereoisomer.

4. The method of claim 1, wherein said compound is an enantiomer.

5. The method of claim 1, wherein said compound is a racemate.

6. The method of claim 1, wherein said compound is a diastereomer.

7. The method of claim 1, wherein said compound is a tautomer.

8. The method according to claim 2 is selected from compound MV-A, compound MV-B, compound MV-C or compound MV-D:

MV-A

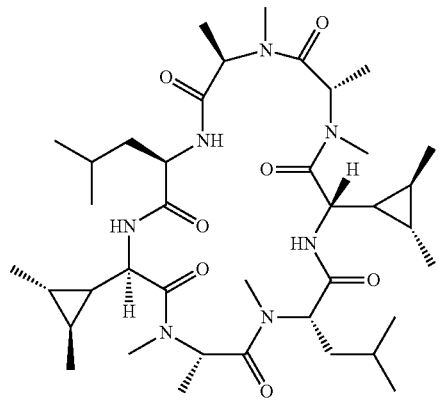

MV-B

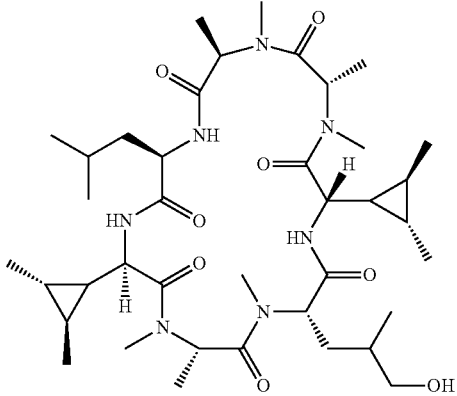

MV-C

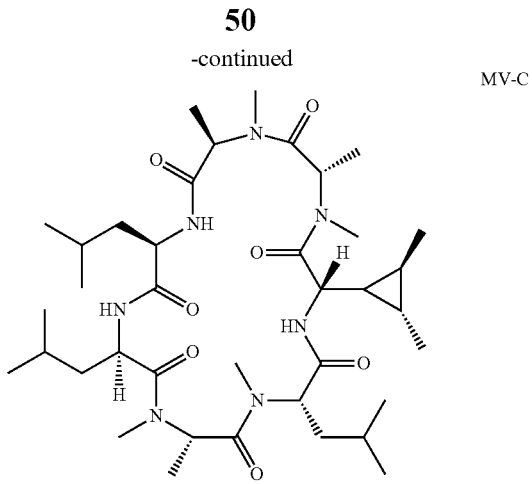

MV-D

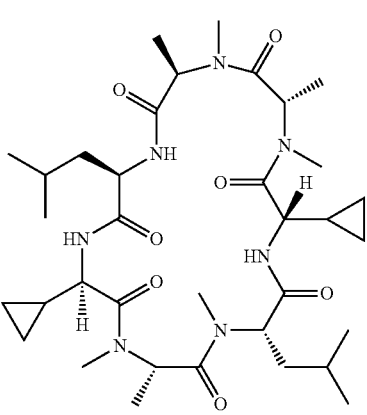

or a pharmaceutically acceptable salt or prodrug thereof.

9. The method of claim 1, wherein said subject is a human.

10. The method according to claim 1, wherein the effective dosage is at least 0.0041 mg/kg per patient body weight.

11. The method according to claim 1, wherein the effective dosage is at least 0.0081 mg/kg per patient body weight.

12. The method according to claim 1, wherein the effective dosage is at least 0.0162 mg/kg per patient body weight.

13. The method according to claim 1, wherein the effective dosage is at least 0.0324 mg/kg per patient body weight.

14. The method according to claim 1, wherein the effective dosage is at least 0.0649 mg/kg per patient body weight.

15. The method according to claim 1, wherein the effective dosage is at least 0.0405 mg/kg per patient body weight.

16. The method according to claim 1, wherein the effective dosage is at least 0.0811 mg/kg per patient body weight.

17. The method according to claim 1, wherein the effective dosage is at least 0.162 mg/kg per patient body weight.

* * * * *